(12) United States Patent
Cuny et al.

(10) Patent No.: US 7,491,743 B2
(45) Date of Patent: Feb. 17, 2009

(54) INHIBITORS OF CELLULAR NECROSIS

(75) Inventors: Gregory D. Cuny, Somerville, MA (US); Junying Yuan, Newton, MA (US); Prakash Jagtap, Beverly, MA (US); Alexei Degterev, Brookline, MA (US)

(73) Assignees: President and Fellows of Harvard College, Cambridge, MA (US); The Brigham and Women's Hospital, Inc., Boston, MA (US)

( * ) Notice: Subject to any disclaimer, the term of this patent is extended or adjusted under 35 U.S.C. 154(b) by 276 days.

(21) Appl. No.: 10/930,690

(22) Filed: Aug. 30, 2004

(65) Prior Publication Data

US 2005/0119260 A1 Jun. 2, 2005

Related U.S. Application Data

(60) Provisional application No. 60/498,882, filed on Aug. 29, 2003.

(51) Int. Cl.
*A61K 31/415* (2006.01)
*C07D 403/02* (2006.01)

(52) U.S. Cl. .................. 514/397; 514/398; 548/312.1
(58) Field of Classification Search .............. 548/312.1; 514/397, 398
See application file for complete search history.

(56) References Cited

U.S. PATENT DOCUMENTS

| 4,110,536 | A | 8/1978 | Havera et al. |
|---|---|---|---|
| 4,332,952 | A | 6/1982 | Schnur |
| 4,837,165 | A | 6/1989 | Hawke |
| 5,693,643 | A | 12/1997 | Gilbert et al. |
| 6,756,394 | B1 * | 6/2004 | Yuan et al. ............... 514/389 |
| 6,797,708 | B2 * | 9/2004 | McKew et al. ........... 514/228.2 |

FOREIGN PATENT DOCUMENTS

| EP | 0343643 B1 | 3/1994 |
|---|---|---|
| EP | 1275646 | 1/2003 |
| GB | 2080803 | 2/1982 |
| JP | 02019363 A2 | 1/1990 |
| WO | WO 92/04045 | 3/1992 |
| WO | WO 96/30393 | 10/1996 |
| WO | WO 98/39303 | 9/1998 |
| WO | WO 01/28493 | 4/2001 |
| WO | WO 01/85718 | 11/2001 |
| WO | WO 04/070050 | 8/2004 |

OTHER PUBLICATIONS

Havera et al., 1979, CAS: 90: 121596.*
Horwell et al., 1992, CAS: 117:84251.*
Becker et al., 1996, CAS : 125 :327717.*
Borner et al., "Apoptosis Without Caspases: An Inefficient Molecular Guillotine?" *Cell Death Differ.* 6:497-507 (1999).
Buyukbingol et al., "Studies on the Synthesis and Structure-Activity Relationships of 5-(3'-indolal)-2-Thiohydantoin Derivatives as Aldose Reductase Enzyme Inhibitors," *Farmaco* 49:443-447 (1994).
Chi et al., "Oncogenic Ras Triggers Cell Suicide Through the Activation of a Caspase- Independent Cell Death Program in Human Cancer Cells," *Oncogene* 18: 2281-2290 (1999).
Cryns et al., "Proteases to Die For," *Genes & Develop.* 12:1551-1570 (1978).
Degterev et al., "Chemical Inhibitor of Nonapoptotic Cell Death With Therapeutic Potential for Ischemic Brain Injury," *Nat. Chem. Biol.* 1:112-119 (2005).
Edman, "Method for Determination of the Amino Acid Sequence in Peptides," *Acta Chem. Scand.* 4:283-293 (1950).
Eldadah et al., "Caspase Pathways, Neuronal Apoptosis, and CNS Injury," *J. Neurotrauma* 17:811-829 (2000).
Fiers et al., "More Than One Way to Die: Apoptosis, Necrosis and Reactive Oxygen Damage," *Oncogene* 18:7719-7730 (1999).
Fujiwara et al., "$^{13}$C Nuclear Magnetic Resonance Studies on the Conformation of Substituted Hydantoins," *J. Chemical Soc. Perkin* 2:1573-1577 (1980).
Hara et al., "Inhibition of Interleukin 1beta Converting Enzyme Family Proteases Reduces Ischemic and Excitotoxic Neuronal Damage," *Proc Natl Acad Sci U.S.A.* 94:2007-2012 (1997).
Herceg et al., "Failure of Poly(ADP-ribose) Polymerase Cleavage by Caspases Leads to Induction of Necrosis and Enhanced Apoptosis," *Mol Cell Biol.* 19:5124-5133 (1999).
Hirsch et al., "The Apoptosis-Necrosis Paradox, Apoptogenic Proteases Activated After Mitochondrial Permeability Transition Determine the Mode of Cell Death," *Oncogene* 15:1573-1581 (1997).
Holler et al., "Fas Triggers an Alternative, Caspase-8-Independent Cell Death Pathway Using the Kinase RIP as Effector Molecule," *Nature Immunol.* 1:489-495 (2000).
Inglis et al., "The identification of tryptophan residues in proteins as oxidised derivatives during amino acid sequence determinations," *FEBS Letters* 104:115-118 (1979).
Janin et al., "Methyl Orthocarboxylates as Methylating Agents of Heterocycles," *Eur. J. Org. Chem.* 1763-1769 (2002).
Kaul et al., "Pathways to Neuronal Injury and Apoptosis in HIV-Associated Dementia," *Nature* 410:988-994 (2001).
Kawahara et al., "Caspase-Independent Cell Killing by Fas-Associated Protein With Death Domain," *J. Cell Biol.* 143:1353-1360 (1998).
Khwaja et al., "Resistance to the Cytotoxic Effects of Tumor Necrosis Factor Alpha can be Overcome by Inhibition of a FADD/Caspase-Dependent Signaling Pathway," *J. Biol. Chem.* 274:36817-36823 (1999).
Kitanaka et al., "Caspase-Independent Programmed Cell Death With Necrotic Morphology," *Cell Death Differ.* 6:508-515 (1999).
Leist et al., "Inhibition of Mitochondrial ATP Generation by Nitric Oxide Switches Apoptosis to Necrosis," *Exp. Cell Res.* 249:396-403 (1999).

(Continued)

*Primary Examiner*—Rei-tsang Shiao
(74) *Attorney, Agent, or Firm*—Clark & Elbing LLP; Kristina Bieker-Brady

(57) ABSTRACT

The present invention relates to compounds and pharmaceutical preparations and their use in therapy for preventing or treating trauma, ischemia, stroke and degenerative diseases associated with cell death. Methods and compositions of the invention are particularly useful for treating neurological disorders associated with cellular necrosis.

25 Claims, 12 Drawing Sheets

OTHER PUBLICATIONS

Lewis et al., "Tryptophan-Derived NK1 Antagonists: Conformationally Constrained Heterocyclic Bioisosteres of the Ester Linkage," *J. Med. Chem.* 38:923-933 (1995).

Li et al., "Induction of Necrotic-Like Cell Death by Tumor Necrosis Factor Alpha and Caspase Inhibitors: Novel Mechanism for Killing Virus-Infected Cells," *J. Virol.* 74:7470-7477 (2000).

Luschen et al., "Sensitization to Death Receptor Cytotoxicity by Inhibition of Fas-Associated Death Domain Protein (FADD)/Caspase Signaling. Requirement of Cell Cycle Progression," *J. Biol. Chem.* 275:24670-24678 (2000).

Martin et al., "Neurodegeneration in Excitotoxicity, Global Cerebral Ischemia, And Target Deprivation: A Perspective on the Contributions of Apoptosis and Necrosis," *Brain Res. Bull.* 46:281-309 (1998).

Matsumura et al., "Necrotic Death Pathway in Fas Receptor Signaling," *J. Cell Biol.* 151:1247-1255 (2000).

McCarthy et al., "Inhibition of Ced-3/ICE-Related Proteases Does Not Prevent Cell Death Induced by Oncogenes, DNA Damage, or the Bcl-2 Homologue Bak," *J. Cell Biol.* 136:215-227 (1997).

McMurray, "Huntington's Disease: New Hope for Therapeutics," *Trends Neurosci.* 24:S32-S38 (2001).

Molina et al., "A Simple and General Entry to Aplysinopsine-Type Alkaloids by Tandem Aza-Wittig/Heterocumulene-Mediated Annelation," *Tet Lett.* 33:4491-4494 (1992).

Nicotera et al., "Apoptosis and Necrosis: Different Execution of the Same Death," *Biochem. Soc. Symp.* 66:69-73 (1999).

Park et al., "Diastereoselective Synthesis of Hydantoin- and Isoxazoline-Substituted Dispirocyclobutanoids," *J. Org. Chem.* 65:3520-3524 (2000).

Polverino et al., "Selective Activation of Capases During Apoptotic Induction in HL-60 Cells," *J. Biol. Chem.* 272:7013-7021 (1997).

Raghupathi et al., "Apoptosis After Traumatic Brain Injury," *J. Neurotrauma* 17:927-938 (2000).

Sané et al., "Caspase Inhibition in Camptothecin-Treated U-937 Cells is Coupled With a Shift from Apoptosis to Transient G1 Arrest Followed by Necrotic Cell Death," *Cancer Res.* 59:3565-3569 (1999).

Selkoe, "Translating Cell Biology Into Therapeutic Advances in Alzheimer's Disease," *Nature* 399:A23-A31 (1999).

Syntichaki et al., "Death by Necrosis. Uncontrollable Catastrophe, Or is There Order Behind the Chaos?" *EMBO Rep.* 3:604-609 (2002).

Takahashi et al., "Antimutagenic Properties of 3, 5-Disubstituted 2-Thiohydantoins," *J. Agric. Food Chem.* 46:5037-5042 (1998).

Talanian et al., "Caspases as Targets for Anti-Inflammatory and Anti-Apoptotic Drug Discovery," *J. Med. Chem.* 43:3351-3371 (2000).

Teng et al., "Structure-Activity Relationship Study of Novel Necroptosis Inhibitors," *Bioorg. Med. Chem. Lett.* 15:5039-5044 (2005).

Vercammen et al., "Dual Signaling of the Fas Receptor: Initiation of Both Apoptotic and Necrotic Cell Death Pathways," *J. Exp. Med.* 188:919-930 (1998).

Vercammen et al., "Inhibition of Caspases Increases the Sensitivity of L929 Cells to Necrosis Mediated by Tumor Necrosis Factor," *J. Exp. Med.* 187:1477-1485 (1998).

Vila et al., "Engineered modeling and the secrets of Parkinson's disease," *Trends Neurosci.* 24:S49-S55 (2001).

Waterfield et al., "Amino Acid Sequence Analysis with Methyl Isothiocyanate Resolution of the Methylthiohydantoins by Gas- Liquid Partition Chromatography," *Biochemistry* 9:832-839 (1970).

Woo, "Gas-Chromatographic Determination of Methylthiohydantoin Amino Acid as N(O)-Butyldimethylsilyl Derivatives in Amino Acid Sequencing with Methylisothiocyanate," *J. Korean Agric. Chem. Soc.* 35:132-138 (1992).

Wyllie et al., "Cell Death: The Significance of Apoptosis," *Int. Rev. Cytol.* 68:251-306 (1980).

Yuan et al., "Apoptosis in the Nervous System," *Nature* 407:802-809 (2000).

International Search Report dated Apr. 5, 2001 (PCT/US00/28475).

International Search Report dated Jan. 18, 2006 (PCT/US04/028270).

International Preliminary Report of Patentability dated Feb. 28, 2006 (PCT/US04/028270).

European Patent Office Communication dated Mar. 3, 2008 (European Application No. 04821344.1).

Gulati et al., "A New Synthesis of 5-bromoaplysinopsin, 6-bromoaplysinopsin and 3'-demethylaplysinopsin and Their Biological Activities," *Indian J Chem.* 33B (1):10-16 (1994).

Jakse et al., "New Synthetic Routes to Thiooxoaplysinopsines and Their Derivatives," *Zbornik Referatov s Postvetovanja Slovenski Kemijski Dnevi*, Maribor, Solvenia (Sep. 28-29, 2000), Meeting Date 2000, Issue Pt. 1, 141-146 (Abstract in English on p. 146).

Jakse et al., "New Synthetic Routes to Thiooxoaplysinopsines and Their Derivatives," *Zbornik Referatov s Postvetovanja Slovenski Kemijski Dnevi*, Maribor, Solvenia (Sep. 28-29, 2000), Meeting Date 2000, Issue Pt. 1, 141-146 (Abstract only).

Khodair, "A Convenient Synthesis of Glycosylated hydantoins as Potential Antiviral Agents," *Phosphorus Sulfur Silicon Relat Elem.* 122:9-26 (1997).

Nowak, "Application of Allyl Isothiocyanate in Synthesis of 3/allyl-2-thiohydantoins from Amino Acids and in Degradation of Proteins," *Roczniki Chemii.* 47(12):2377-2378 (1973).

Nowak, "Allyl Isothiocyanate in Synthesis of 3/allyl-2-thiohydantoins from Amino Acids and in Degradation of Proteins," *Roczniki Chemii.* 47(12):2377-2378 (1973) (Abstract only).

Rahman et al., "Synthesis and Biological Studies of Thiohydantoins," *Bandladesh J Bio Sci.* 5(1):28-30 (1976).

Selič et al., "A Simple Stereoselective Synthesis of Aplysinopsin Analogs," *Helv Chim Acta.* 83(10):2802-2811 (2000).

* cited by examiner

■ 893-54
▲ 893-10

INHIBITORS OF CELLULAR NECROSIS

PRIORITY INFORMATION

This application claims the benefit under 35 U.S.C. § 119 (e) of the filing date of U.S. Provisional Application No. 60/498,882 filed Aug. 29, 2003, herein incorporated by reference.

FEDERALLY SPONSORED RESEARCH

This invention was made with Government support under National Institute of Health Grant No. GM-64703. The Government may have certain rights to this invention.

FIELD OF INVENTION

The invention relates to compositions and methods for preventing and treating diseases involving cell death. In particular, the invention relates to therapeutic compounds and methods for treating neurological diseases involving cell death.

BACKGROUND OF INVENTION

Acute and chronic neurological diseases can be caused by a number of different factors. However, many of these diseases are characterized by cell death in specific regions of the central nervous system.

Neurological diseases are a group of maladies that afflict a significant portion of the human population. The medical and socioeconomic impacts of these diseases are significant. Although the etiology of each acute and chronic neurological disease is likely different, one common feature that many share is rapid or progressive irreversible cell death in specific regions of the central nervous system (Standaert, D. G.; Young, A. B. In *Goodman & Gilman's The Pharmacological Basis of Therapeutics, Tenth Edition*; Hardman, J. G.; Limbird, L. E., Eds.; McGraw-Hill: New York, 2001; Chapter 22, pp 549-568; Mattson, M. P. *Nature Rev. Mol. Cell. Biol.* 2000, 1, 120-129). Compelling evidence is emerging that neuron cell death occurs in acute neurological diseases, such as stroke and trauma (Raghupathi, R.; Graham, D. I.; McIntosh, T. K. *J. Neurotrauma* 2000, 17(10), 927-38) and in neurodegenerative diseases, such as Parkinson's disease—PD (Vila, M.; Wu, D. C.; Przedborski, S. *Trends in Neuroscience* 2001, 24(11), S49-S55), Huntington's disease—HD (McMurry, C. T. *Trends in Neuroscience* 2001, 24(11), S32-S38), amyotrophic lateral sclerosis—ALS (Beckman, J. S.; Estéves, A. G.; Crow, J. P. *Trends in Neuroscience* 2001, 24(11), S15-S20), and human immunodeficiency virus associated dementia—HAD (Kaul, M.; Garden, G. W.; Lipton, S. A. *Nature* 2001, 410, 988-994). Studies have also suggested that cell death occurs in Alzheimer's disease—AD (Eldadah, B. A.; Faden, A. I. *J. Neurotrauma* 2000, 17(10), 811-829). Albeit, neurons present in AD may be chronically dysfunctional without necessarily undergoing active cell death (Selkoe, D. J. *Nature* 1999, 399 (Suppl), A23-A30).

Most current approaches to developing treatments for neurological diseases, such as stroke, Parkinson's disease (PD), Alzheimer's disease (AD), amyotrophic lateral sclerosis (ALS), Huntington's disease (HD), and HIV-associated dementia (HAD) target mechanisms that are hypothesized to be involved in the initiation-phase of the disease. For example, current approaches involve using compounds that attempt to inhibit the initiation of toxicity caused by aggregation of α-synuclein in PD, or aggregation of β-amyloid, tau, and/or ApoE in AD, or aggregation of huntingtin protein in HD, or oxidative stress from reactive oxygen species in ALS, or excessive extracellular excitotoxins, such as glutamate, in stroke or trauma. An alternative approach is to target basic cell death machinery that may be activated as a result of a cellular insult. Current approaches are directed towards a specific death process called apoptosis involving cysteine proteases called caspases. However, a number of recent studies establish that many cell death paradigms, especially those associated with neurodegeneration, involve non-apoptotic/caspase-independent mechanisms.

Therefore, there is a need in the art for compositions and methods to prevent or treat cellular necrosis including cellular necrosis associated with neurodegeneration.

SUMMARY OF INVENTION

The present invention provides compounds and pharmaceutical preparations that are useful for treating disorders associated with cellular necrosis.

According to one aspect the invention, the compound has the formula:

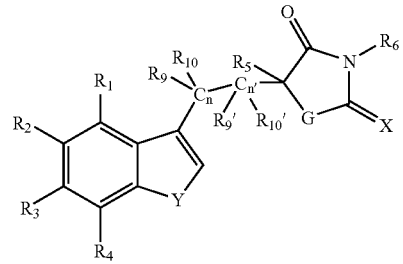

a stereoisomeric form thereof, a pharmaceutically acceptable acid or base addition salt thereof, wherein X represents O; Y represents S; G represents O or $NR_7$; $R_1$, $R_2$, and $R_3$ represent independently H, OH, $OR_8$, F, Cl, Br, I, $N(R_8)_2$, COOH, $CO_2R_8$, $NO_2$, $NHC(O)R_8$, lower alkyl, substituted lower alkyl, aryl, substituted aryl, heteroaryl, or substituted heteroaryl; $R_4$ represents independently H, OH, $OR_8$, F, Cl, Br, I, $N(R_8)_2$, COOH, $CO_2R_8$, $NO_2$, $NHC(O)R_8$, methyl, methoxyl, lower alkyl, substituted lower alkyl, aryl, substituted aryl, heteroaryl, or substituted heteroaryl, amine, piperizine; $R_5$, $R_6$, and $R_7$ represent independently H or lower alkyl; $R_8$ represents lower alkyl, substituted lower alkyl, aryl, substituted aryl, arylalkyl, alkenyl, alkynyl, heteroaryl, or substituted heteroaryl; $R_9$, $R_{10}$, $R_9'$, $R_{10}'$, represent independently H, F, Cl, Br, I, lower alkyl, substituted lower alkyl, or a three to six membered cycloalkyl or substituted cycloalkyl that includes $C_n$ and/or $C_{n'}$; n and n' equals an integer from zero to five.

In another aspect the compound has the formula:

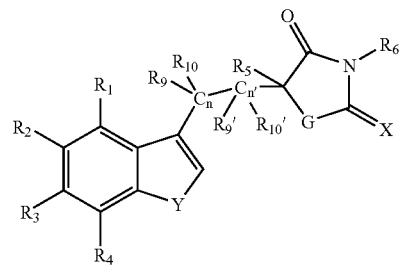

a stereoisomeric form thereof, a pharmaceutically acceptable acid or base addition salt thereof, wherein X represents O; Y represents $NR_8$; G represents O or $NR_7$; $R_1$, $R_2$, and $R_3$ represent independently H, OH, $OR_8$, F, Cl, Br, I, $N(R_8)_2$, COOH, $CO_2R_8$, $NO_2$, $NHC(O)R_8$, lower alkyl, substituted lower alkyl, aryl, substituted aryl, heteroaryl, or substituted heteroaryl; $R_4$ represents independently H, OH, $OR_8$, F, Cl, Br, I, $N(R_8)_2$, COOH, $CO_2R_8$, $NO_2$, $NHC(O)R_8$, methyl, methoxyl, lower alkyl, substituted lower alkyl, aryl, substituted aryl, heteroaryl, or substituted heteroaryl, amine, piperizine; $R_5$, $R_6$, and $R_7$ represent independently H or lower alkyl; $R_8$ represents lower alkyl, substituted lower alkyl, aryl, substituted aryl, arylalkyl, alkenyl, alkynyl, heteroaryl, or substituted heteroaryl; $R_9$, $R_{10}$, $R_9'$, $R_{10}'$, represent independently H, F, Cl, Br, I, lower alkyl, substituted lower alkyl, or a three to six membered cycloalkyl or substituted cycloalkyl that includes $C_n$ and/or $C_n'$; n and n' equals an integer from zero to five.

In another aspect of the invention the compound has the formula:

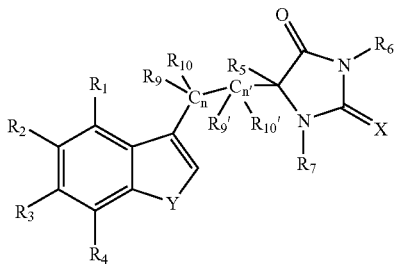

a stereoisomeric form thereof, a pharmaceutically acceptable acid or base addition salt thereof, wherein X represents O; Y represents NH; $R_1$, $R_2$, and $R_3$ represent independently H, $OR_8$, F, Cl, Br, I, $N(R_8)_2$, $CO_2R_8$, $NO_2$, $NHC(O)R_8$, lower alkyl, substituted lower alkyl, aryl, substituted aryl, heteroaryl, or substituted heteroaryl; $R_4$ represents independently H, $OR_8$, F, Cl, Br, I, $N(R_8)_2$, $CO_2R_8$, $NO_2$, $NHC(O)R_8$, methyl, methoxyl, lower alkyl, substituted lower alkyl, aryl, substituted aryl, heteroaryl, or substituted heteroaryl, amine, piperizine; $R_5$, $R_6$ and $R_7$ represent independently H or lower alkyl, except $R_6$ can not be methyl, ethyl, propyl, isopropyl or t-butyl when $R_1$, $R_2$, $R_3$, $R_4$, $R_5$ and $R_7$ are H; $R_8$ represents H, lower alkyl, substituted lower alkyl, aryl, substituted aryl, arylalkyl, alkenyl, alkynyl, heteroaryl, or substituted heteroaryl; $R_9$, $R_{10}$, $R_9'$, $R_{10}'$, represent independently H, F, Cl, Br, I, lower alkyl, substituted lower alkyl, or a three to six membered cycloalkyl or substituted cycloalkyl that includes $C_n$ and/or $C_n'$; n and n' equals an integer from zero to five.

In another aspect the compound has the formula:

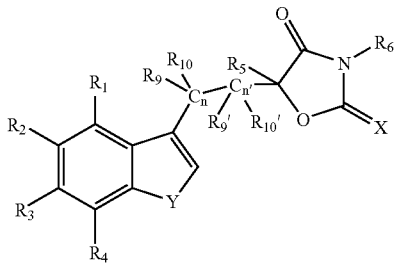

a stereoisomeric form thereof, a pharmaceutically acceptable acid or base addition salt thereof, wherein X represents O; Y represents NH; $R_1$, $R_2$, and $R_3$ represent independently H, OH, $OR_8$, F, Cl, Br, I, $N(R_8)_2$, COOH, $CO_2R_8$, $NO_2$, $NHC(O)R_8$, lower alkyl, substituted lower alkyl, aryl, substituted aryl, heteroaryl, or substituted heteroaryl; $R_4$ represents independently H, OH, $OR_8$, F, Cl, Br, I, $N(R_8)_2$, COOH, $CO_2R_8$, $NO_2$, $NHC(O)R_8$, methyl, methoxyl, lower alkyl, substituted lower alkyl, aryl, substituted aryl, heteroaryl, or substituted heteroaryl, amine, piperizine; $R_5$, $R_6$, and $R_7$ represent independently H or lower alkyl; $R_8$ represents lower alkyl, substituted lower alkyl, aryl, substituted aryl, arylalkyl, alkenyl, alkynyl, heteroaryl, or substituted heteroaryl; $R_9$, $R_{10}$, $R_9'$, $R_{10}'$, represent independently H, F, Cl, Br, I, lower alkyl, substituted lower alkyl, or a three to six membered cycloalkyl or substituted cycloalkyl that includes $C_n$ and/or $C_n'$; n and n' equals an integer from zero to five.

In another aspect the compound has the formula:

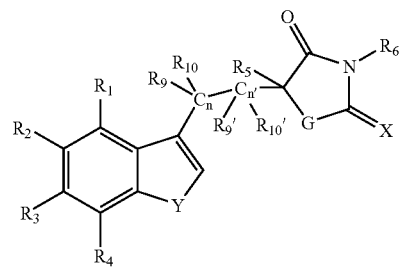

a stereoisomeric form thereof, a pharmaceutically acceptable acid or base addition salt thereof, wherein X represents S; Y represents S; G represents O or $NR_7$; $R_1$, $R_2$, and $R_3$ represent independently H, OH, $OR_8$, F, Cl, Br, I, $N(R_8)_2$, COOH, $CO_2R_8$, $NO_2$, $NHC(O)R_8$, lower alkyl, substituted lower alkyl, aryl, substituted aryl, heteroaryl, or substituted heteroaryl; $R_4$ represents independently H, OH, $OR_8$, F, Cl, Br, I, $N(R_8)_2$, COOH, $CO_2R_8$, $NO_2$, $NHC(O)R_8$, methyl, methoxyl, lower alkyl, substituted lower alkyl, aryl, substituted aryl, heteroaryl, or substituted heteroaryl, amine, piperizine; $R_5$, $R_6$, and $R_7$ represent independently H or lower alkyl; $R_8$ represents lower alkyl, substituted lower alkyl, aryl, substituted aryl, arylalkyl, alkenyl, alkynyl, heteroaryl, or substituted heteroaryl; $R_9$, $R_{10}$, $R_9'$, $R_{10}'$, represent independently H, F, Cl, Br, I, lower alkyl, substituted lower alkyl, or a three to six membered cycloalkyl or substituted cycloalkyl that includes $C_n$ and/or $C_n'$; n and n' equals an integer from zero to five.

In another aspect of the invention the compound has the formula:

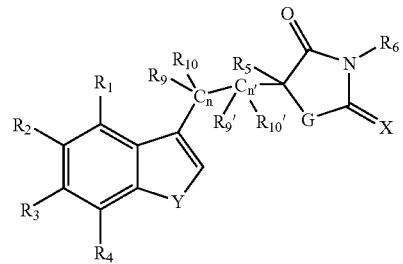

a stereoisomeric form thereof, a pharmaceutically acceptable acid or base addition salt thereof, wherein X represents S; Y represents $NR_8$; G represents O or $NR_7$; $R_1$, $R_2$, and $R_3$ represent independently H, OH, $OR_8$, F, Cl, Br, I, $N(R_8)_2$, COOH, $CO_2R_8$, $NO_2$, $NHC(O)R_8$, lower alkyl, substituted lower alkyl, aryl, substituted aryl, heteroaryl, or substituted heteroaryl; $R_4$ represents independently H, OH, $OR_8$, F, Cl, Br, I, $N(R_8)_2$, COOH, $CO_2R_8$, $NO_2$, $NHC(O)R_8$, methyl, methoxyl, lower alkyl, substituted lower alkyl, aryl, substituted aryl, heteroaryl, or substituted heteroaryl, amine, piperizine; $R_5$, $R_6$, and $R_7$ represent independently H or lower alkyl; $R_8$ represents lower alkyl, substituted lower alkyl, aryl, substituted aryl, arylalkyl, alkenyl, alkynyl, heteroaryl, or substituted heteroaryl; $R_9$, $R_{10}$, $R_9'$, $R_{10}'$, represent independently H, F, Cl, Br, I, lower alkyl, substituted lower alkyl, or a three to six membered cycloalkyl or substituted cycloalkyl that includes $C_n$ and/or $C_n'$; n and n' equals an integer from zero to five.

In another aspect of the invention the compound has the formula:

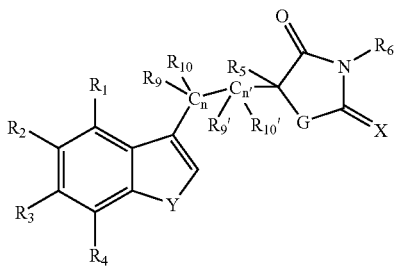

a stereoisomeric form thereof, a pharmaceutically acceptable acid or base addition salt thereof, wherein X represents S; Y represents NH; G represents O or $NR_7$; $R_1$, $R_2$, and $R_3$ represent independently H, $OR_8$, F, Cl, Br, I, $N(R_8)_2$, $CO_2R_8$, $NO_2$, $NHC(O)R_8$, lower alkyl, substituted lower alkyl, aryl, substituted aryl, heteroaryl, or substituted heteroaryl; $R_4$ represents independently H, $OR_8$, F, Cl, Br, I, $N(R_8)_2$, $CO_2R_8$, $NO_2$, $NHC(O)R_8$, aryl, substituted aryl, heteroaryl, or substituted heteroaryl, amine, piperizine, lower alkyl and substituted lower alkyl except for methyl and methoxyl; $R_5$, $R_6$ and $R_7$ represent independently H or lower alkyl, except $R_6$ can not be methyl when $R_1$, $R_2$, $R_3$, $R_4$, $R_5$ and $R_7$ are H; $R_8$ represents H, lower alkyl, substituted lower alkyl, aryl, substituted aryl, arylalkyl, alkenyl, alkynyl, heteroaryl, or substituted heteroaryl; $R_9$, $R_{10}$, $R_9'$, $R_{10}'$, represent independently H, F, Cl, Br, I, lower alkyl, substituted lower alkyl, or a three to six membered cycloalkyl or substituted cycloalkyl that includes $C_n$ and/or $C_n'$; n and n' equals an integer from zero to five.

In another aspect of the invention the compound has the formula:

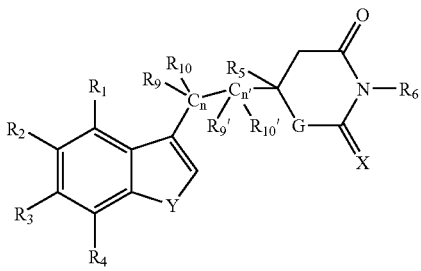

a stereoisomeric form thereof, a pharmaceutically acceptable acid or base addition salt thereof, wherein X represents S or O; Y represents S, NH or $NR_8$; G represents O or $NR_7$; $R_1$, $R_2$, and $R_3$ represent independently H, $OR_8$, F, Cl, Br, I, $N(R_8)_2$, $CO_2R_8$, $NO_2$, $NHC(O)R_8$, lower alkyl, substituted lower alkyl, aryl, substituted aryl, heteroaryl, or substituted heteroaryl; $R_4$ represents independently H, $OR_8$, F, Cl, Br, I, $N(R_8)_2$, $CO_2R_8$, $NO_2$, $NHC(O)R_8$, aryl, substituted aryl, heteroaryl, or substituted heteroaryl, amine, piperizine, lower alkyl and substituted lower alkyl; $R_5$, $R_6$ and $R_7$ represent independently H or lower alkyl; $R_8$ represents H, lower alkyl, substituted lower alkyl, aryl, substituted aryl, arylalkyl, alkenyl, alkynyl, heteroaryl, or substituted heteroaryl; $R_9$, $R_{10}$, $R_9'$, $R_{10}'$, represent independently H, F, Cl, Br, I, lower alkyl, substituted lower alkyl, or a three to six membered cycloalkyl or substituted cycloalkyl that includes $C_n$ and/or $C_n'$; n and n' equals an integer from zero to five.

Another aspect of the invention relates to pharmaceutical preparations comprising the above compounds and a pharmaceutically acceptable carrier. In preferred embodiments of the invention the pharmaceutically acceptable carrier is chosen from a diluent, a solid filler, and a solvent encapsulating material.

An additional aspect of the invention relates to the use of the above compounds for treating necrotic cell diseases including trauma, ischemia, stroke, cardiac infarction, infection and sepsis. In preferred embodiment the necrotic cell disease is a neurodegenerative disease such as Parkinson's disease, Alzheimer's disease, amyotrophic lateral sclerosis, Huntington's disease, and HIV-associated dementia.

An additional aspect of the invention relates to the use of a combination of two or more compounds that inhibit cellular necrosis (e.g., heterocylcic thiohydantoin, hydantoin, oxazolidinone, thioxo-oxazolidinone, pyrimidinone, oxazinanone compounds, or combinations thereof) according to a treatment method of the invention.

An additional aspect of the invention relates to the use of one or more of the aforementioned compounds in combination with one or more additional compounds or agents such as those described herein. In preferred embodiments of the invention the additional compound(s) is (are) selected from apoptosis inhibitors, PARP inhibitors, Src inhibitors, agents for treating cardiovascular disorders and anti-microbial agents.

An additional aspect of the invention relates to processes for producing one or more heterocyclic compounds comprising a thiohydantoin, hydantoin, oxazolidinone, thioxo-oxazolidinone, pyrimidinone, or oxazinanone moiety.

A further aspect of the present invention relates to the synthesis of combinatorial libraries of the heterocyclic compounds comprising a thiohydantoin, hydantoin, oxazolidinone, thioxo-oxazolidinone, pyrimidinone, or oxazinanone moiety, and the screening of those libraries for biological activity, e.g. in assays based on cell death (apoptosis, necrosis, or a combination of both) and in animal models of disease including trauma, ischemia (e.g. stroke, myocardial infraction and the like), and neurodegenerative diseases such as Parkinson's disease (PD), Alzheimer's disease (AD), amyotrophic lateral sclerosis (ALS), Huntington's disease (HD), infectious encephalopathies, dementia, HIV-associated dementia (HAD), etc.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

Figure 1:
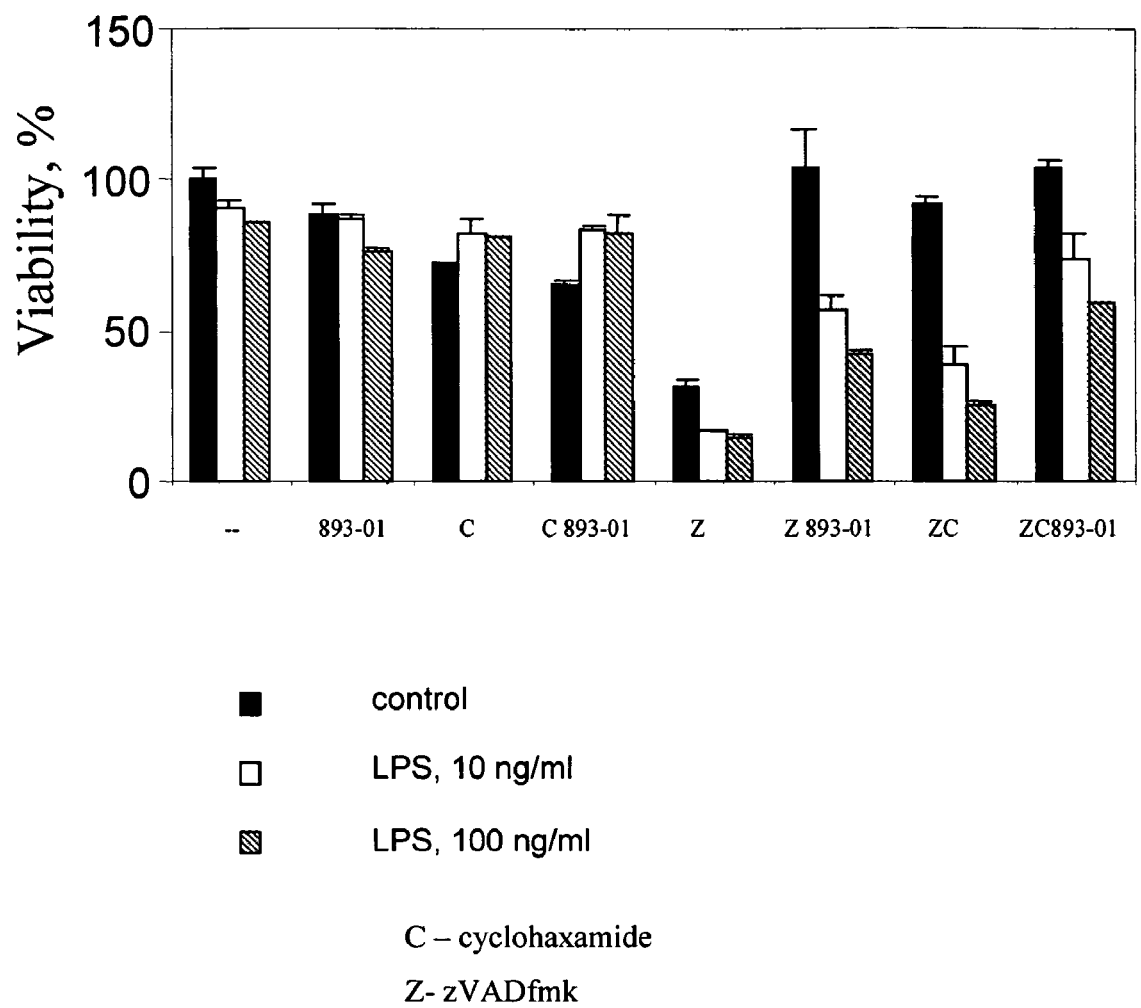
FIG. 1 is a graph bar that shows the effects of anti-necrotic compound 893-01.

The invention provides compounds that prevent cell death and are useful as therapeutic agents for treating subjects afflicted with necrotic cell disease, such as trauma, ischemic and neurological diseases, and particularly neurodegenerative diseases. Compounds of the invention are also useful for understanding the patho-physiology of these diseases.

Compounds of the invention are low molecular weight molecules of the formula:

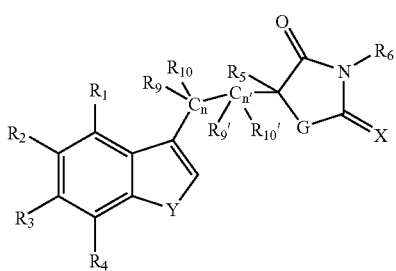

a stereoisomeric form thereof, a pharmaceutically acceptable acid or base addition salt thereof, wherein X represents O or S;

Y represents S, NH, or $NR_8$;

G represents O or $NR_7$;

$R_1$, $R_2$, and $R_3$ represent independently H, OH, $OR_8$, F, Cl, Br, I, $N(R_8)_2$, COOH, $CO_2R_8$, $NO_2$, $NHC(O)R_8$, lower alkyl, substituted lower alkyl, aryl, substituted aryl, heteroaryl, or substituted heteroaryl;

$R_4$ represents independently H, OH, $OR_8$, F, Cl, Br, I, $N(R_8)_2$, COOH, $CO_2R_8$, $NO_2$, $NHC(O)R_8$, methyl, methoxyl, lower alkyl, substituted lower alkyl, aryl, substituted aryl, heteroaryl, substituted heteroaryl, amine, or piperizine, but preferably Cl, F or methoxyl;

$R_5$, $R_6$, and $R_7$ represent independently H or lower alkyl;

$R_8$ represents lower alkyl, substituted lower alkyl, aryl, substituted aryl, arylalkyl, alkenyl, alkynyl, heteroaryl, or substituted heteroaryl;

$R_9$, $R_{10}$, $R_9'$, $R_{10}'$, represent independently H, F, Cl, Br, I, lower alkyl, substituted lower alkyl, or a three to six membered cycloalkyl or substituted cycloalkyl the includes $C_n$ and/or $C_{n'}$;

n and n' equals an integer from zero to five;

with restrictions on the following alternative embodiments:

i) when X represents O, Y represents NH and G represents $NR_7$, $R_6$ can not be a methyl, ethyl, propyl, isopropyl or t-butyl when $R_1$, $R_2$, $R_3$, $R_4$, $R_5$ and $R_7$ represent H;

ii) when X represents S, Y represents NH and G represents $NR_7$, $R_6$ can not be a methyl when $R_1$, $R_2$, $R_3$, $R_4$, $R_5$ and $R_7$ represent H;

iii) and when X represents S, Y represents NH and G represents $NR_7$, $R_4$ can not be a methyl or methoxyl.

In another aspect of the invention compounds of the invention are low molecular weight molecules of the formula:

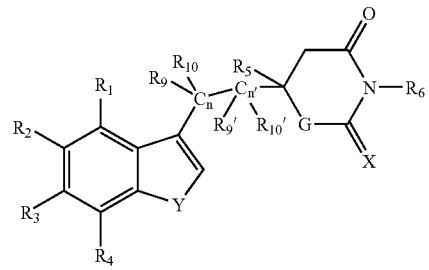

a stereoisomeric form thereof, a pharmaceutically acceptable acid or base addition salt thereof, wherein X represents O or S;

Y represents S, NH, or $NR_8$;

G represents O or $NR_7$;

$R_1$, $R_2$, and $R_3$ represent independently H, OH, $OR_8$, F, Cl, Br, I, $N(R_8)_2$, COOH, $CO_2R_8$, $NO_2$, $NHC(O)R_8$, lower alkyl, substituted lower alkyl, aryl, substituted aryl, heteroaryl, or substituted heteroaryl;

$R_4$ represents independently H, OH, $OR_8$, F, Cl, Br, I, $N(R_8)_2$, COOH, $CO_2R_8$, $NO_2$, $NHC(O)R_8$, methyl, methoxyl, lower alkyl, substituted lower alkyl, aryl, substituted aryl, heteroaryl, substituted heteroaryl, amine, or piperizine, but preferably Cl or F;

$R_5$, $R_6$, and $R_7$ represent independently H or lower alkyl;

$R_8$ represents lower alkyl, substituted lower alkyl, aryl, substituted aryl, arylalkyl, alkenyl, alkynyl, heteroaryl, or substituted heteroaryl;

$R_9$, $R_{10}$, $R_9'$, $R_{10}'$, represent independently H, F, Cl, Br, I, lower alkyl, substituted lower alkyl, or a three to six membered cycloalkyl or substituted cycloalkyl the includes $C_n$ and/or $C_{n'}$; and wherein n and n' equals an integer from zero to five.

In one aspect, compounds of the invention inhibit necrotic cell death by inhibiting caspase-independent mechanisms that are activated after a cell-death initiating event. According to the invention, the inhibition of caspase-independent cell-death mechanisms provides several advantages, including a high therapeutic efficacy and a broad utility against many diseases, including but not limited to trauma, ischemia and neurological diseases. In addition, compounds of the invention can be used in assays for novel molecular targets that are associated with caspase-independent induced cell death.

Cells die in two morphologically distinct ways (Wyllie, A. H.; Kerr, J. F. R.; Currie, A. R. *Int. Rev. Cytol.* 1980, 68, 251-306). One of these processes, called apoptosis, is characterized by a number of conserved and highly regulated steps including concurrent nucleus and cytoplasm condensation (although cytoplasmic organelles initially remain intact), DNA degradation, membrane blebbing and caspase-mediated cleavage of various cellular factors. Apoptosis culminates in cellular fragmentation into apoptotic bodies, which are phagocytosed by adjacent cells, including macrophages. Therefore, this process does not lead to an inflammatory response. Apoptosis is a genetically regulated process (Yuan, J.; Yankner, B. A. *Nature* 2000, 407, 802-809; Cryns, V.; Yuan, J. *Genes & Develop.* 1998, 12, 1551-1570) necessary during both development and for maintaining an organism's homeostasis. However, in certain pathological conditions this process, which would normally be suppressed, is initiated leading to cell death and dysfunction. Many key cellular targets in this cascade have been identified and some serve as potential targets for therapeutic intervention. For example, one family of enzymes discovered to play an integral role in this process is caspases, which are cysteine proteases (Talanian, R. V.; Brady, K. D.; Cryns, V. L. *J. Med. Chem.* 2000, 43(18), 3351-3371).

A second, morphologically distinct way that cells die, called necrosis (Syntichaki, P.; Tavernarakis, N. *EMBO Rep.* 2002, 3(7), 604-609), is characterized by cell membrane and organelle disruption, cell swelling, mitochondria impairment, followed by cell lyses (Martin, L. J., Al-Abdulla, N. A.; Brambrink, A. M.; Kirsch, J. R.; Sieber, F. E.; Portera-Cailliau, C. *Brain Res. Bull.* 1998, 46(4), 281-309). Condensation of chromatin occurs, but only with diffuse irregular shaped masses being formed. Also, cell lyses typically are accompanied by an inflammatory response. Although the underlying biochemical events in this process are not well understood, necrotic cell death is known to play a very prominent role in many pathological conditions, especially during neurodegeneration (Nicotera, P., Leist, M.; Ferrando-May E. *Biochem. Soc. Symp.* 1999, 66, 69-73). It is thought that inhibition of apoptosis often does not completely block cell death, but rather results in a cell switching from an apoptotic to a necrotic mechanism. Therefore, identifying and preparing low molecular weight molecules that prevent necrotic cell death can assist in the basic understanding of this process and provide useful compounds for therapeutic intervention. Compounds of the invention target important aspects of neurodegeneration not addressed by current strategies.

According to the invention, necrosis can be associated with a condition including, but not limited to, an infection, a toxin, a poison, radiation, physical trauma, inflammation, a lack of nutrient or oxygen supply, a chemical imbalance, an interruption of blood supply, other conditions leading to cell or tissue death, or a combination of two or more of the above. For example, cell or tissue necrosis can be associated with any one or more of the following conditions: an abscess, ague, anemia, ankylosis, anoxia, apnea, arthritis, asphyxiation, asthma, ataxia, atrophy, backache, bleeding, blennorhea, cachexia, caries, colic, constipation, convulsion, coughing, cyanosis, diarrhea, dizziness, dropsy, dry gangrene, dysentery, dyspepsia, dyspnea, edema, emaciation, fainting, fatigue, fever, fibrillation, gas gangrene, genetic diseases, high blood pressure, hydrops, hypertension, hypotension, icterus, indigestion, inflammation, insomnia, itching, jaundice, low blood pressure, lumbago, marasmus, moist gangrene, noma, pain, paralysis, pruritus, rash, rheum, sclerosis, seizure, shock, skin eruption, sore, spasm, sphacelation, tabes, tachycardia, tooth decay, tumor, upset stomach, vertigo, vomiting, or wasting.

Accordingly, necrosis can be localized to a group of living cells or can be spread over one or more larger tissue areas. In some embodiments, necrosis can be associated with gangrene, sphacelus, ischemic necrosis, avascular necrosis (e.g., of the bone), meningitis, and other conditions including but not limited to those described herein.

The term "necrotic cell disease" refers to acute diseases including but not limited to trauma, ischemia, stroke, cardiac infarction, anthrax lethal toxin induced septic shock, sepsis, cell death induced by LPS, and HIV induced T-cell death leading to immunodeficiency. The term "necrotic cell disease" also includes but is not limited to chronic neurodegenerative diseases, such as Parkinson's disease, Huntington's disease, amyotrophic lateral sclerosis, Alzheimer's disease, infectious encelopathies, dementia such as HIV associated dementia.

The invention is based, in part, on the discovery that a series of compounds including, but not limited to, the following:

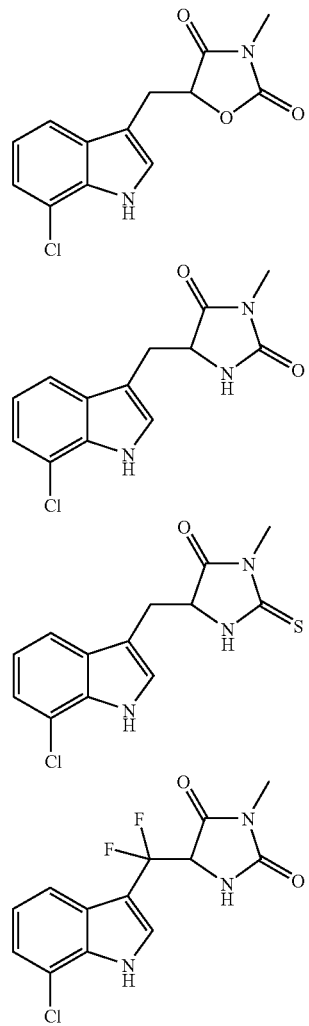

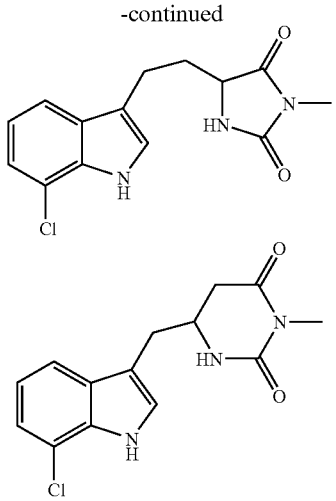

act as inhibitors of cellular necrosis. According to the invention, these compounds, and certain derivatives thereof, are useful to treat diseases such as trauma, ischemia (e.g. stroke, myocardial infarction and the like), and neurodegenerative diseases. Useful thiohydantoin, hydantoin, oxazolidinone, thioxo-oxazolidinone, pyrimidinone, or oxazinanone compound derivatives preferably have small substituents at the 7 position of the indole ring such as halogen, methyl, and methoxyl and groups such as methyl and other lower alkyl groups at the (thio)hydantoin imide nitrogen.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 12 or fewer carbon atoms in its backbone (e.g., $C_1$-$C_{12}$ for straight chain, $C_3$-$C_{12}$ for branched chain), and more preferably 6 or fewer, and even more preferably 4 or fewer. Likewise, preferred cycloalkyls have from 3-10 carbon atoms in their ring structure, and more preferably have 5, 6 or 7 carbons in the ring structure.

Unless the number of carbons is otherwise specified, "lower alkyl" as used herein means an alkyl group, as defined above, but having from one to ten carbons, more preferably from one to six carbon atoms in its backbone structure, and even more preferably from one to four carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

As used herein, the term "halogen" designates —F, —Cl, —Br or —I; the term "sulfhydryl" means —SH; and the term "hydroxyl" means —OH.

The term "methyl" refers to the monovalent radical —CH$_3$, and the term "methoxyl" refers to the monovalent radical —CH$_2$OH.

The term "aralkyl" or "arylalkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms ortho, meta and para apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" or "heteroaryl" refer to 3- to 10-membered ring structures, more preferably 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, heterocyclyl, aromatic or heteroaromatic moiety, —CF$_3$, —CN, or the like.

As used herein, the definition of each expression, e.g. alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, heterocyclyl, aromatic or heteroaromatic moiety, —$CF_3$, —CN, or the like. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention. In certain embodiments, the present invention relates to a compound represented by any of the structures outlined herein, wherein the compound is a single stereoisomer.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as inhibitors of cellular necrosis), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants, which are in themselves known, but are not mentioned here.

For purposes of this invention, the chemical elements are identified in accordance with the Periodic Table of the Elements, CAS version, Handbook of Chemistry and Physics, 67th Ed., 1986-87, inside cover.

Accordingly, in certain embodiments, the invention provides a compound of the formula:

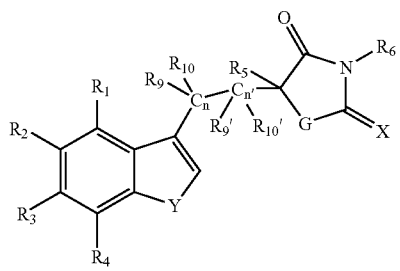

a stereoisomeric form thereof, a pharmaceutically acceptable acid or base addition salt thereof, wherein X represents O; Y represents S; G represents O or $NR_7$; $R_1$, $R_2$, and $R_3$ represent independently H, OH, $OR_8$, F, Cl, Br, I, $N(R_8)_2$, COOH, $CO_2R_8$, $NO_2$, $NHC(O)R_8$, lower alkyl, substituted lower alkyl, aryl, substituted aryl, heteroaryl, or substituted heteroaryl; $R_4$ represents independently H, OH, $OR_8$, F, Cl, Br, I, $N(R_8)_2$, COOH, $CO_2R_8$, $NO_2$, $NHC(O)R_8$, methyl, methoxyl, lower alkyl, substituted lower alkyl, aryl, substituted aryl, heteroaryl, or substituted heteroaryl, amine, piperizine; $R_5$, $R_6$, and $R_7$ represent independently H or lower alkyl; $R_8$ represents lower alkyl, substituted lower alkyl, aryl, substituted aryl, arylalkyl, alkenyl, alkynyl, heteroaryl, or substituted heteroaryl; $R_9$, $R_{10}$, $R_9'$, $R_{10}'$, represent independently H, F, Cl, Br, I, lower alkyl, substituted lower alkyl, or a three to six membered cycloalkyl or substituted cycloalkyl that includes $C_n$ and/or $C_{n'}$; n and n' equals an integer from zero to five.

In certain embodiments the invention provides a compound of the formula:

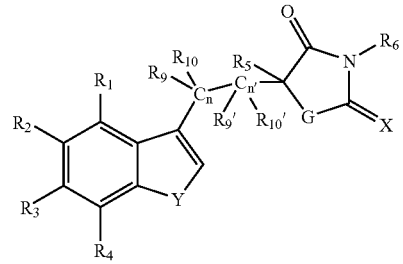

a stereoisomeric form thereof, a pharmaceutically acceptable acid or base addition salt thereof, wherein X represents O; Y represents $NR_8$; G represents O or $NR_7$; $R_1$, $R_2$, and $R_3$ represent independently H, OH, $OR_8$, F, Cl, Br, I, $N(R_8)_2$, COOH, $CO_2R_8$, $NO_2$, $NHC(O)R_8$, lower alkyl, substituted lower alkyl, aryl, substituted aryl, heteroaryl, or substituted heteroaryl; $R_4$ represents independently H, OH, $OR_8$, F, Cl, Br, I, $N(R_8)_2$, COOH, $CO_2R_8$, $NO_2$, $NHC(O)R_8$, methyl, methoxyl, lower alkyl, substituted lower alkyl, aryl, substituted aryl, heteroaryl, or substituted heteroaryl, amine, piperizine; $R_5$, $R_6$, and $R_7$ represent independently H or lower alkyl; $R_8$ represents lower alkyl, substituted lower alkyl, aryl, substituted aryl, arylalkyl, alkenyl, alkynyl, heteroaryl, or substituted heteroaryl; $R_9$, $R_{10}$, $R_9'$, $R_{10}'$, represent independently H, F, Cl, Br, I, lower alkyl, substituted lower alkyl, or a three to six membered cycloalkyl or substituted cycloalkyl that includes $C_n$ and/or $C_{n'}$; n and n' equals an integer from zero to five.

In certain embodiments the invention provides a compound of the formula:

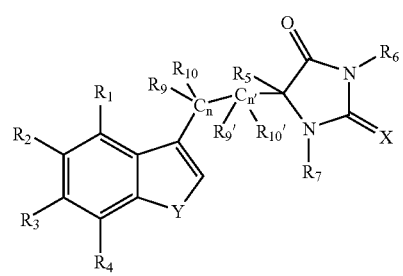

a stereoisomeric form thereof, a pharmaceutically acceptable acid or base addition salt thereof, wherein X represents O; Y represents NH; $R_1$, $R_2$, and $R_3$ represent independently H, $OR_8$, F, Cl, Br, I, $N(R_8)_2$, $CO_2R_8$, $NO_2$, $NHC(O)R_8$, lower alkyl, substituted lower alkyl, aryl, substituted aryl, heteroaryl, or substituted heteroaryl; $R_4$ represents independently H, $OR_8$, F, Cl, Br, I, $N(R_8)_2$, $CO_2R_8$, $NO_2$, $NHC(O)R_8$, methyl, methoxyl, lower alkyl, substituted lower alkyl, aryl, substituted aryl, heteroaryl, or substituted heteroaryl, amine, piperizine; $R_5$, $R_6$ and $R_7$ represent independently H or lower alkyl, except $R_6$ can not be methyl, ethyl, propyl, isopropyl or t-butyl when $R_1$, $R_2$, $R_3$, $R_4$, $R_5$ and $R_7$ are H; $R_8$ represents H, lower alkyl, substituted lower alkyl, aryl, substituted aryl, arylalkyl, alkenyl, alkynyl, heteroaryl, or substituted heteroaryl; $R_9$, $R_{10}$, $R_9'$, $R_{10}'$, represent independently H, F, Cl, Br, I, lower alkyl, substituted lower alkyl, or a three to six membered cycloalkyl or substituted cycloalkyl that includes $C_n$ and/or $C_{n'}$; n and n' equals an integer from zero to five.

In certain embodiments the invention provides a compound of the formula:

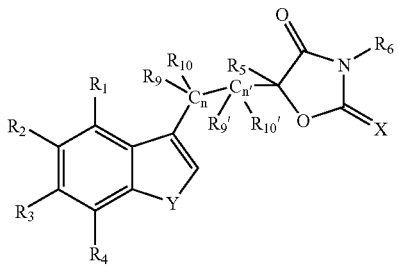

a stereoisomeric form thereof, a pharmaceutically acceptable acid or base addition salt thereof, wherein X represents O; Y represents NH; $R_1$, $R_2$, and $R_3$ represent independently H, OH, $OR_8$, F, Cl, Br, I, $N(R_8)_2$, COOH, $CO_2R_8$, $NO_2$, $NHC(O)R_8$, lower alkyl, substituted lower alkyl, aryl, substituted aryl, heteroaryl, or substituted heteroaryl; $R_4$ represents independently H, OH, $OR_8$, F, Cl, Br, I, $N(R_8)_2$, COOH, $CO_2R_8$, $NO_2$, $NHC(O)R_8$, methyl, methoxyl, lower alkyl, substituted lower alkyl, aryl, substituted aryl, heteroaryl, or substituted heteroaryl, amine, piperizine; $R_5$, $R_6$, and $R_7$ represent independently H or lower alkyl; $R_8$ represents lower alkyl, substituted lower alkyl, aryl, substituted aryl, arylalkyl, alkenyl, alkynyl, heteroaryl, or substituted heteroaryl; $R_9$, $R_{10}$, $R_9'$, $R_{10}'$, represent independently H, F, Cl, Br, I, lower alkyl, substituted lower alkyl, or a three to six membered cycloalkyl or substituted cycloalkyl that includes $C_n$ and/or $C_{n'}$; n and n' equals an integer from zero to five.

In certain embodiments the invention provides a compound of the formula:

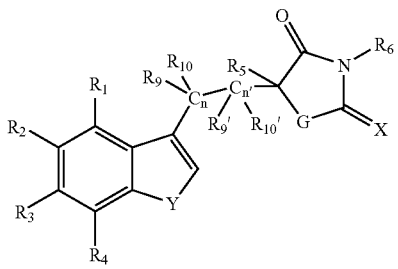

a stereoisomeric form thereof, a pharmaceutically acceptable acid or base addition salt thereof, wherein X represents S; Y represents S; G represents O or $NR_7$; $R_1$, $R_2$, and $R_3$ represent independently H, OH, $OR_8$, F, Cl, Br, I, $N(R_8)_2$, COOH, $CO_2R_8$, $NO_2$, $NHC(O)R_8$, lower alkyl, substituted lower alkyl, aryl, substituted aryl, heteroaryl, or substituted heteroaryl; $R_4$ represents independently H, OH, $OR_8$, F, Cl, Br, I, $N(R_8)_2$, COOH, $CO_2R_8$, $NO_2$, $NHC(O)R_8$, methyl, methoxyl, lower alkyl, substituted lower alkyl, aryl, substituted aryl, heteroaryl, or substituted heteroaryl, amine, piperizine; $R_5$, $R_6$, and $R_7$ represent independently H or lower alkyl; $R_8$ represents lower alkyl, substituted lower alkyl, aryl, substituted aryl, arylalkyl, alkenyl, alkynyl, heteroaryl, or substituted heteroaryl; $R_9$, $R_{10}$, $R_9'$, $R_{10}'$, represent independently H, F, Cl, Br, I, lower alkyl, substituted lower alkyl, or a three to six membered cycloalkyl or substituted cycloalkyl that includes $C_n$ and/or $C_{n'}$; n and n' equals an integer from zero to five.

In certain embodiments the invention provides a compound of the formula:

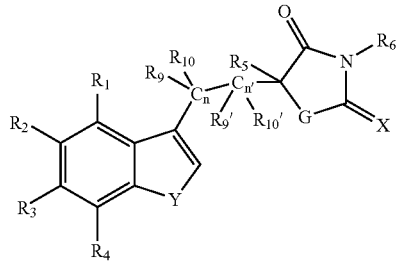

a stereoisomeric form thereof, a pharmaceutically acceptable acid or base addition salt thereof, wherein X represents S; Y represents $NR_8$; G represents O or $NR_7$; $R_1$, $R_2$, and $R_3$ represent independently H, OH, $OR_8$, F, Cl, Br, I, $N(R_8)_2$, COOH, $CO_2R_8$, $NO_2$, $NHC(O)R_8$, lower alkyl, substituted lower alkyl, aryl, substituted aryl, heteroaryl, or substituted heteroaryl; $R_4$ represents independently H, OH, $OR_8$, F, Cl, Br, I, $N(R_8)_2$, COOH, $CO_2R_8$, $NO_2$, $NHC(O)R_8$, methyl, methoxyl, lower alkyl, substituted lower alkyl, aryl, substituted aryl, heteroaryl, or substituted heteroaryl, amine, piperizine; $R_5$, $R_6$, and $R_7$ represent independently H or lower alkyl; $R_8$ represents lower alkyl, substituted lower alkyl, aryl, substituted aryl, arylalkyl, alkenyl, alkynyl, heteroaryl, or substituted heteroaryl; $R_9$, $R_{10}$, $R_9'$, $R_{10}'$, represent independently H, F, Cl, Br, I, lower alkyl, substituted lower alkyl, or a three to six membered cycloalkyl or substituted cycloalkyl that includes $C_n$ and/or $C_{n'}$; n and n' equals an integer from zero to five.

In certain embodiments the invention provides a compound of the formula:

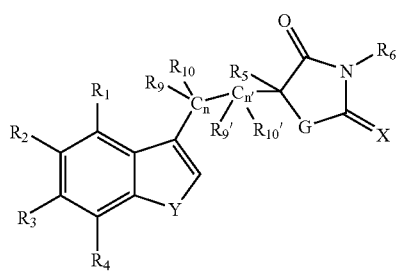

a stereoisomeric form thereof, a pharmaceutically acceptable acid or base addition salt thereof, wherein X represents S; Y represents NH; G represents O or $NR_7$; $R_1$, $R_2$, and $R_3$ represent independently H, $OR_8$, F, Cl, Br, I, $N(R_8)_2$, $CO_2R_8$, $NO_2$, $NHC(O)R_8$, lower alkyl, substituted lower alkyl, aryl, substituted aryl, heteroaryl, or substituted heteroaryl; $R_4$ represents independently H, $OR_8$, F, Cl, Br, I, $N(R_8)_2$, $CO_2R_8$, $NO_2$, $NHC(O)R_8$, aryl, substituted aryl, heteroaryl, or substituted heteroaryl, amine, piperizine, lower alkyl and substituted lower alkyl except for methyl and methoxyl; $R_5$, $R_6$ and $R_7$ represent independently H or lower alkyl, except $R_6$ can not be methyl when $R_1$, $R_2$, $R_3$, $R_4$, $R_5$ and $R_7$ are H; $R_8$ represents H, lower alkyl, substituted lower alkyl, aryl, substituted aryl, arylalkyl, alkenyl, alkynyl, heteroaryl, or substituted heteroaryl; $R_9$, $R_{10}$, $R_9'$, $R_{10}'$, represent independently H, F, Cl, Br, I, lower alkyl, substituted lower alkyl, or a three to six membered cycloalkyl or substituted cycloalkyl that includes $C_n$ and/or $C_n'$; n and n' equals an integer from zero to five.

In certain embodiments the invention provides a compound of the formula:

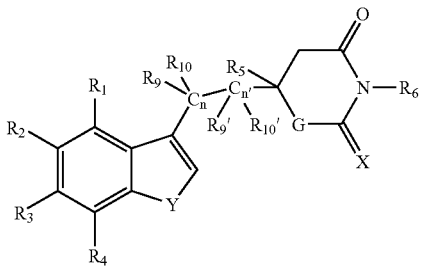

a stereoisomeric form thereof, a pharmaceutically acceptable acid or base addition salt thereof, wherein X represents S or O; Y represents S, NH, or $NR_8$; G represents O or $NR_7$; $R_1$, $R_2$, and $R_3$ represent independently H, $OR_8$, F, Cl, Br, I, $N(R_8)_2$, $CO_2R_8$, $NO_2$, $NHC(O)R_8$, lower alkyl, substituted lower alkyl, aryl, substituted aryl, heteroaryl, or substituted heteroaryl; $R_4$ represents independently H, $OR_8$, F, Cl, Br, I, $N(R_8)_2$, $CO_2R_8$, $NO_2$, $NHC(O)R_8$, aryl, substituted aryl, heteroaryl, or substituted heteroaryl, amine, piperizine, lower alkyl and substituted lower alkyl except for methyl and methoxyl; $R_5$, $R_6$ and $R_7$ represent independently H or lower alkyl; $R_8$ represents H, lower alkyl, substituted lower alkyl, aryl, substituted aryl, arylalkyl, alkenyl, alkynyl, heteroaryl, or substituted heteroaryl; $R_9$, $R_{10}$, $R_9'$, $R_{10}'$, represent independently H, F, Cl, Br, I, lower alkyl, substituted lower alkyl, or a three to six membered cycloalkyl or substituted cycloalkyl that includes $C_n$ and/or $C_n'$; n and n' equals an integer from zero to five.

In another aspect, the present invention provides pharmaceutically acceptable compositions, which comprise a therapeutically effective amount of one or more of the compounds described herein, formulated together with one or more pharmaceutically acceptable carriers (additives) and/or diluents. As described in detail, the pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Examples of such formulations include, but are not limited to DMSO, 10 mM DMSO, 8% hydroxypropyl-beta-cyclodextrin in PBS, propylene glycol, etc.

For example, in a certain embodiment the compounds of the invention, such as 893-54 can be used as 4 mM solution in 8% hydroxypropyl-beta-cyclodextrin in PBS for parenteral administration. In another embodiment 893-54 (0.40 mg/mL) was formulated as follows: 5.975 mg of 893-54 was weighed into a pre-cleaned 20 mL glass vial, 1.49 mL of propylene glycol was added to the vial followed by vortexing and sonication for 15 minutes, and 13.41 mL of sterile normal saline was added for a total volume of 14.9 mL followed by vortexing.

As set out herein, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19.)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenyl sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions, which are compatible with body tissue.

In another aspect, the present invention relates to a method of treating a disease associated with cellular necrosis. In particular, the invention provides methods for preventing or treating a disorder associated with cellular necrosis in a mammal, comprising the step of administering to said mammal a therapeutically effective amount of a compound or therapeutic preparation of the present invention. In certain embodiments, the disorder associated with cellular necrosis is a neurological disorder such as trauma, ischemia or stroke. In other embodiments, the neurological disorder is a neurodegenerative disease, such as Parkinson's disease (PD), Alzheimer's disease (AD), amyotrophic lateral sclerosis (ALS), Huntington's disease (HD), and HIV-associated dementia (HAD). In other embodiments the disorder is an ischemic disease of organs including but not limited to brain, heart, kidney, and liver. In certain embodiments, the mammal is a primate, canine or feline subject. In other embodiments, the mammal is a human subject.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. A therapeutically effective amount for treating a neurological disorder is an amount sufficient to inhibit necrosis in at least a subset of cells that were exposed to a cell-death initiating event. Accordingly, a therapeutically effective amount prevents or minimizes disease progression associated with cellular necrosis. Disease progression can be monitored relative to an expected disease progression that is based on population studies, controlled observations in individuals, or a combination of both.

In certain embodiments, a compound or pharmaceutical preparation is administered orally. In other embodiments, the compound or pharmaceutical preparation is administered intravenously. Alternative routes of administration include sublingual, intramuscular, and transdermal administrations.

In certain embodiments, the present invention relates to ligands for inhibiting cell death, wherein the ligands are represented by any of the structures outlined above, and any sets of definitions associated with one of those structures. In certain embodiments, the ligands of the present invention are inhibitors of cell death. In any event, the ligands of the present invention preferably exert their effect on inhibiting cell death at a concentration less than about 50 micromolar, more preferably at a concentration less than about 10 micromolar, and most preferably at a concentration less than 1 micromolar.

The compounds of the invention can be tested in standard animal models of stroke and standard protocols such as described by Hara, H., et al. Proc Natl Acad Sci U S A, 1997. 94(5): 2007-12.

When the compounds of the present invention are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts. A daily, weekly, or monthly dosage (or other time interval) can be used.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In general, a suitable daily dose of a compound of the invention will be that amount of the compound that is the lowest dose effective to produce a therapeutic effect. Such an effective dose will generally depend upon the factors described above. Generally doses of the compounds of this invention for a patient, when used for the indicated effects, will range from about 0.0001 to about 100 mg per kg of body weight per day. Preferably the daily dosage will range from 0.001 to 50 mg of compound per kg of body weight, and even more preferably from 0.01 to 10 mg of compound per kg of body weight.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: oral administration, for example, drenches (aqueous or non-aqueous solutions or suspensions), tablets, boluses, powders, granules, pastes for application to the tongue; parenteral administration, for example, by subcutaneous, intramuscular or intravenous injection as, for example, a sterile solution or suspension; topical application, for example, as a cream, ointment or spray applied to the skin, lungs, or oral cavity; or intravaginally or intravectally, for example, as a pessary, cream or foam; sublingually; ocularly; transdermally; nasally; pulmonary or to other mucosal surfaces.

The compounds according to the invention may be formulated for administration in any convenient way for use in human or veterinary medicine, by analogy with other pharmaceuticals.

The term "treatment" is intended to encompass also prophylaxis, therapy and cure. The patient receiving this treatment is any animal in need of such treatment, including primates, in particular humans, and other mammals such as equines, cattle, swine and sheep; and poultry and pets in general.

In another aspect of the invention the compounds can be administered in combination with compounds that are apoptosis inhibitors. The term "apoptosis inhibitor" refers to compounds that inhibit apoptosis, including but not limited to reversible and irreversible caspase inhibitors. An example of an apoptosis inhibitor includes zVAD (N-benzyloxycarbonyl-Val-Ala-Asp-(OMe) fluoromethyl ketone), IETD (N-acetyl-Ile-Glu-Thr-Asp-al), YVAD (N-benzyloxycarbonyl-Tyr-Val-Ala-Asp-(OMe) fluoromethyl ketone), DEVD (N-[2-(6-hydroxy-3-oxo-3H-xanthen-9-yl)benzoyl]-L-α-aspartyl-L-α-glutamyl-N-[(1S)-1-(carboxymethyl)-3-fluoro-2-oxopropyl]-L-Valinamide), and LEHD (N-acetyl-Leu-Glu-His-Asp-al).

In some preferred embodiments the compounds of the invention are administered in combination with PARP poly (ADP-ribose) polymerase inhibitors. Non-limiting examples of PARP inhibitors include 6(5H)-Phenanthridinone, 4-Amino-1,8-naphthalimide, 1,5-Isoquinolinediol, and 3-Aminobenzamide.

In yet other preferred embodiments the compounds of the invention are administered in combination with Src inhibitors. Src proteins are mammalian cytoplasmic tyrosine kinases that play an extensive role in signal transduction. Examples of Src inhibitors include but are not limited to: PP1(1-(1,1-dimethylethyl)-1-(4-methylphenyl)-1H-pyrazolo[3,4-d]pyrimidin-4-amine), PP2 (3-(4-chlorophenyl)-1-(1,1-dimethylethyl)-1H-pyrazolo[3,4-d]pyrimidin-4-amine), damnacanthal (3-hydroxy-1-methoxy-2-anthraquinonecarboxaldehyde), and SU-5565.

The term "trauma" as used herein refers to any physical damage to the body caused by violence, accident, fracture etc. The term "ischemia" refers to a cardiovascular disorder characterized by a low oxygen state usually due to the obstruction of the arterial blood supply or inadequate blood flow leading to hypoxia in the tissue. The term "stroke" refers to cardiovascular disorders caused by a blood clot or bleeding in the brain, most commonly caused by an interruption in the flow of blood in the brain as from clot blocking a blood vessel, and in certain embodiments of the invention the term stroke refers to ischemic stroke or hemorrhagic stroke. The term "myocardial infarction" refers to a cardiovascular disorder characterized by localized necrosis resulting from obstruction of the blood supply.

The methods of the invention involve, in some aspects, combinations of compounds that are inhibitors of cellular necrosis (e.g., heterocyclic thiohydantoin, hydantoin, oxazolidinone, thioxo-oxazolidinone, pyrimidinone, or oxazinanone compounds, or combinations thereof) with agents for the treatment of cardiovascular disorders. The term "agents for treating cardiovascular disorders" include compounds selected from the group consisting of anti-inflammatory agents, anti-thrombotic agents, anti-platelet agents, fibrinolytic agents, lipid reducing agents, direct thrombin inhibitors, glycoprotein IIb/IIIa receptor inhibitors, agents that bind to cellular adhesion molecules and inhibit the ability of white blood cells to attach to such molecules (e.g. anti-cellular adhesion molecule antibodies), calcium channel blockers, beta-adrenergic receptor blockers, cyclooxygenase-2 inhibitors, angiotensin system inhibitors, and/or any combinations thereof.

One preferred agent is aspirin.

"Anti-inflammatory" agents include Alclofenac; Alclometasone Dipropionate; Algestone Acetonide; Alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Deflazacort; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Methylprednisolone Suleptanate; Mornifumate; Nabumetone; Naproxen; Naproxen Sodium; Naproxol; Nimazone; Olsalazine Sodium; Orgotein; Orpanoxin; Oxaprozin; Oxyphenbutazone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Salycilates; Sanguinarium Chloride; Seclazone; Sermetacin; Sudoxicam; Sulindac; Suprofen; Talmetacin; Talniflumate; Talosalate; Tebufelone; Tenidap; Tenidap Sodium; Tenoxicam; Tesicam; Tesimide; Tetrydamine; Tiopinac; Tixocortol Pivalate; Tolmetin; Tolmetin Sodium; Triclonide; Triflumidate; Zidometacin; Glucocorticoids; Zomepirac Sodium.

"Anti-thrombotic" and/or "fibrinolytic" agents include Plasminogen (to plasmin via interactions of prekallikrein, kininogens, Factors XII, XIIIa, plasminogen proactivator, and tissue plasminogen activator[TPA]) Streptokinase; Urokinase: Anisoylated Plasminogen-Streptokinase Activator Complex; Pro-Urokinase; (Pro-UK); rTPA (alteplase or activase; r denotes recombinant); rPro-UK; Abbokinase; Eminase; Sreptase Anagrelide Hydrochloride; Bivalirudin; Dalteparin Sodium; Danaparoid Sodium; Dazoxiben Hydrochloride; Efegatran Sulfate; Enoxaparin Sodium; Ifetroban; Ifetroban Sodium; Tinzaparin Sodium; retaplase; Trifenagrel; Warfarin; Dextrans.

"Anti-platelet" agents include Clopridogrel; Sulfinpyrazone; Aspirin; Dipyridamole; Clofibrate; Pyridinol Carbamate; PGE; Glucagon; Antiserotonin drugs; Caffeine; Theophyllin Pentoxifyllin; Ticlopidine; Anagrelide.

"Lipid reducing" agents include gemfibrozil, cholystyramine, colestipol, nicotinic acid, probucol lovastatin, fluvastatin, simvastatin, atorvastatin, pravastatin, cirivastatin.

"Direct thrombin inhibitors" include hirudin, hirugen, hirulog, agatroban, PPACK, thrombin aptamers.

"Glycoprotein IIb/IIIa receptor inhibitors" are both antibodies and non-antibodies, and include but are not limited to ReoPro (abcixamab), lamifiban, tirofiban.

"Calcium channel blockers" are a chemically diverse class of compounds having important therapeutic value in the control of a variety of diseases including several cardiovascular disorders, such as hypertension, angina, and cardiac arrhythmias (Fleckenstein, *Cir. Res.* v. 52, (suppl. 1), p. 13-16 (1983); Fleckenstein, *Experimental Facts and Therapeutic Prospects*, John Wiley, New York (1983); McCall, D., *Curr Pract Cardiol*, v. 10, p. 1-11 (1985)). Calcium channel blockers are a heterogenous group of drugs that prevent or slow the entry of calcium into cells by regulating cellular calcium channels. (Remington, *The Science and Practice of pharmacy*, Nineteenth Edition, Mack Publishing Company, Eaton, Pa., p. 963 (1995)). Most of the currently available calcium channel blockers, and useful according to the present invention, belong to one of three major chemical groups of drugs, the dihydropyridines, such as nifedipine, the phenyl alkyl amines, such as verapamil, and the benzothiazepines, such as diltiazem. Other calcium channel blockers useful according to the invention, include, but are not limited to, amrinone, amlodipine, bencyclane, felodipine, fendiline, flunarizine, isradipine, nicardipine, nimodipine, perhexylene, gallopamil, tiapamil and tiapamil analogues (such as 1993RO-11-2933), phenyloin, barbiturates, and the peptides dynorphin, omega-conotoxin, and omega-agatoxin, and the like and/or pharmaceutically acceptable salts thereof.

"Beta-adrenergic receptor blocking agents" are a class of drugs that antagonize the cardiovascular effects of catecholamines in angina pectoris, hypertension, and cardiac arrhythmias. Beta-adrenergic receptor blockers include, but are not limited to, atenolol, acebutolol, alprenolol, befunolol, betaxolol, bunitrolol, carteolol, celiprolol, hedroxalol, indenolol, labetalol, levobunolol, mepindolol, methypranol, metindol, metoprolol, metrizoranolol, oxprenolol, pindolol, propranolol, practolol, practolol, sotalolnadolol, tiprenolol, tomalolol, timolol, bupranolol, penbutolol, trimepranol, 2-(3-(1,1-dimethylethyl)-amino-2-hydroxypropoxy)-3-pyridenecarbonitrilHCl, 1-butylamino-3-(2,5-dichlorophenoxy)-2-propanol, 1-isopropylamino-3-(4-(2-cyclopropylmethoxyethyl)phenoxy)-2-propanol, 3-isopropylamino-1-(7-methylindan-4-yloxy)-2-butanol, 2-(3-t-butylamino-2-hydroxy-propylthio)-4-(5-carbamoyl-2-thienyl)thiazol,7-(2-hydroxy-3-t-butylaminpropoxy)phthalide. The above-identified compounds can be used as isomeric mixtures, or in their respective levorotating or dextrorotating form.

Cyclooxygenase-2 (COX-2) is a recently identified new form of a cyclooxygenase. "Cyclooxygenase" is an enzyme complex present in most tissues that produces various prostaglandins and thromboxanes from arachidonic acid. Nonsteroidal, anti-inflammatory drugs exert most of their anti-inflammatory, analgesic and antipyretic activity and inhibit hormone-induced uterine contractions and certain types of cancer growth through inhibition of the cyclooxygenase (also known as prostaglandin G/H synthase and/or prostaglandin-endoperoxide synthase). Initially, only one form of cyclooxygenase was known, the "constitutive enzyme" or cyclooxygenase-1 (COX-1). It and was originally identified in bovine seminal vesicles.

Cyclooxygenase-2 (COX-2) has been cloned, sequenced and characterized initially from chicken, murine and human sources (See, e.g., U.S. Pat. No. 5,543,297, issued Aug. 6, 1996 to Cromlish, et al., and assigned to Merck Frosst Canada, Inc., Kirkland, Calif., entitled: "Human cyclooxygenase-2 cDNA and assays for evaluating cyclooxygenase-2 activity"). This enzyme is distinct from the COX-1. COX-2, is rapidly and readily inducible by a number of agents including mitogens, endotoxin, hormones, cytokines and growth factors. As prostaglandins have both physiological and pathological roles, it is believed that the constitutive enzyme, COX-1, is responsible, in large part, for endogenous basal release of prostaglandins and hence is important in their physiological functions such as the maintenance of gastrointestinal integrity and renal blood flow. By contrast, it is believed that the inducible form, COX-2, is mainly responsible for the pathological effects of prostaglandins where rapid induction of the enzyme would occur in response to such agents as inflammatory agents, hormones, growth factors, and cytokines. Therefore, it is believed that a selective inhibitor of COX-2 has similar anti-inflammatory, antipyretic and analgesic properties to a conventional non-steroidal anti-inflammatory drug, and in addition inhibits hormone-induced uterine contractions and also has potential anti-cancer effects, but with reduced side effects. In particular, such COX-2 inhibitors are believed to have a reduced potential for gastrointestinal toxicity, a reduced potential for renal side effects, a reduced effect on bleeding times and possibly a decreased potential to induce asthma attacks in aspirin-sensitive asthmatic subjects, and are therefore useful according to the present invention.

A number of selective "COX-2 inhibitors" are known in the art. These include, but are not limited to, COX-2 inhibitors described in U.S. Pat. No. 5,474,995 "Phenyl heterocycles as cox-2 inhibitors"; U.S. Pat. No. 5,521,213 "Diaryl bicyclic heterocycles as inhibitors of cyclooxygenase-2"; U.S. Pat. No. 5,536,752 "Phenyl heterocycles as COX-2 inhibitors"; U.S. Pat. No. 5,550,142 "Phenyl heterocycles as COX-2 inhibitors"; U.S. Pat. No. 5,552,422 "Aryl substituted 5,5 fused aromatic nitrogen compounds as anti-inflammatory agents"; U.S. Pat. No. 5,604,253 "N-benzylindol-3-yl propanoic acid derivatives as cyclooxygenase inhibitors"; U.S. Pat. No. 5,604,260 "5-methanesulfonamido-1-indanones as an inhibitor of cyclooxygenase-2"; U.S. Pat. No. 5,639,780 N-benzyl indol-3-yl butanoic acid derivatives as cyclooxygenase inhibitors"; U.S. Pat. No. 5,677,318 Diphenyl-1,2-3-thiadiazoles as anti-inflammatory agents"; U.S. Pat. No. 5,691,374 "Diaryl-5-oxygenated-2-(5H)-furanones as COX-2 inhibitors"; U.S. Pat. No. 5,698,584 "3,4-diaryl-2-hydroxy-2,5-dihydrofurans as prodrugs to COX-2 inhibitors"; U.S. Pat. No. 5,710,140 "Phenyl heterocycles as COX-2 inhibitors"; U.S. Pat. No. 5,733,909 "Diphenyl stilbenes as prodrugs to COX-2 inhibitors"; U.S. Pat. No. 5,789,413 "Alkylated styrenes as prodrugs to COX-2 inhibitors"; U.S. Pat. No. 5,817,700 "Bisaryl cyclobutenes derivatives as cyclooxygenase inhibitors"; U.S. Pat. No. 5,849,943 "Stilbene derivatives useful as cyclooxygenase-2 inhibitors"; U.S. Pat. No. 5,861,419 "Substituted pyridines as selective cyclooxygenase-2 inhibitors"; U.S. Pat. No. 5,922,742 "Pyridinyl-2-cyclopenten-1-ones as selective cyclooxygenase-2 inhibitors"; U.S. Pat. No. 5,925,631 "Alkylated styrenes as prodrugs to COX-2 inhibitors"; all of which are commonly assigned to Merck Frosst Canada, Inc. (Kirkland, Calif.). Additional COX-2 inhibitors are also described in U.S. Pat. No. 5,643,933, assigned to G. D. Searle & Co. (Skokie, Ill.), entitled: "Substituted sulfonylphenylheterocycles as cyclooxygenase-2 and 5-lipoxygenase inhibitors."

A number of the above-identified COX-2 inhibitors are prodrugs of selective COX-2 inhibitors, and exert their action by conversion in vivo to the active and selective COX-2 inhibitors. The active and selective COX-2 inhibitors formed from the above-identified COX-2 inhibitor prodrugs are described in detail in WO 95/00501, published Jan. 5, 1995, WO 95/18799, published Jul. 13, 1995 and U.S. Pat. No. 5,474,995, issued Dec. 12, 1995. Given the teachings of U.S. Pat. No. 5,543,297, entitled: "Human cyclooxygenase-2 cDNA and assays for evaluating cyclooxygenase-2 activity," a person of ordinary skill in the art would be able to determine whether an agent is a selective COX-2 inhibitor or a precursor of a COX-2 inhibitor, and therefore part of the present invention.

An "angiotensin system inhibitor" is an agent that interferes with the function, synthesis or catabolism of angiotensin II. These agents include, but are not limited to, angiotensin-converting enzyme (ACE) inhibitors, angiotensin II antagonists, angiotensin II receptor antagonists, agents that activate the catabolism of angiotensin II, and agents that prevent the synthesis of angiotensin I from which angiotensin II is ultimately derived. The renin-angiotensin system is involved in the regulation of hemodynamics and water and electrolyte balance. Factors that lower blood volume, renal perfusion pressure, or the concentration of $Na^+$ in plasma tend to activate the system, while factors that increase these parameters tend to suppress its function.

Angiotensin I and angiotensin II are synthesized by the enzymatic renin-angiotensin pathway. The synthetic process is initiated when the enzyme renin acts on angiotensinogen, pseudoglobulin in blood plasma, to produce the decapeptide angiotensin I. Angiotensin I is converted by angiotensin converting enzyme (ACE) to angiotensin II (angiotensin-[1-8] octapeptide). The latter is an active pressor substance which has been implicated as a causative agent in several forms of hypertension in various mammalian species, e.g., humans.

Angiotensin (renin-angiotensin) system inhibitors are compounds that act to interfere with the production of angiotensin II from angiotensinogen or angiotensin I or interfere with the activity of angiotensin II. Such inhibitors are well known to those of ordinary skill in the art and include compounds that act to inhibit the enzymes involved in the ultimate production of angiotensin II, including renin and ACE. They also include compounds that interfere with the activity of angiotensin II, once produced. Examples of classes of such compounds include antibodies (e.g., to renin), amino acids and analogs thereof (including those conjugated to larger molecules), peptides (including peptide analogs of angiotensin and angiotensin I), pro-renin related analogs, etc. Among the most potent and useful renin-angiotensin system inhibitors are renin inhibitors, ACE inhibitors, and angiotensin II antagonists. In a preferred embodiment of the invention, the renin-angiotensin system inhibitors are renin inhibitors, ACE inhibitors, and angiotensin II antagonists.

"Angiotensin II antagonists" are compounds which interfere with the activity of angiotensin II by binding to angiotensin II receptors and interfering with its activity. Angiotensin II antagonists are well known and include peptide compounds and non-peptide compounds. Most angiotensin II antagonists are slightly modified congeners in which agonist activity is attenuated by replacement of phenylalanine in position 8 with some other amino acid; stability can be enhanced by other replacements that slow degeneration in vivo. Examples of angiotensin II antagonists include: peptidic compounds (e.g., saralasin, [(San$^1$)(Val$^5$)(Ala$^8$)] angiotensin-(1-8) octapeptide and related analogs); N-substituted imidazole-2-one (U.S. Pat. No. 5,087,634); imidazole acetate derivatives including 2-N-butyl-4-chloro-1-(2-chlorobenzile) imidazole-5-acetic acid (see Long et al., *J. Pharmacol. Exp. Ther.* 247(1), 1-7 (1988)); 4, 5,6,7-tetrahydro-1H-imidazo[4,5-c]pyridine-6-carboxylic acid and analog derivatives (U.S. Pat. No. 4,816,463); N2-tetrazole beta-glucuronide analogs (U.S. Pat. No. 5,085,992); substituted pyrroles, pyrazoles, and tryazoles (U.S. Pat. No. 5,081,127); phenyl and heterocyclic derivatives such as 1,3-imidazoles (U.S. Pat. No. 5,073,566); imidazo-fused 7-member ring heterocycles (U.S. Pat. No. 5,064,825); peptides (e.g., U.S. Pat. No. 4,772,684); antibodies to angiotensin II (e.g., U.S. Pat. No. 4,302,386); and aralkyl imidazole compounds such as biphenyl-methyl substituted imidazoles (e.g., EP Number 253,310, Jan. 20, 1988); ES8891 (N-morpholinoacetyl-(-1-naphthyl)-L-alanyl-(4, thiazolyl)-L-alanyl (35, 45)-4-amino-3-hydroxy-5-cyclo-hexapentanoyl-N-hexylamide, Sankyo Company, Ltd., Tokyo, Japan); SKF108566 (E-alpha-2-[2-butyl-1-(carboxy phenyl) methyl]1H-imidazole-5-yl[methylane]-2-thiophenepropanoic acid, Smith Kline Beecham Pharmaceuticals, PA); Losartan (DUP753/MK954, DuPont Merck Pharmaceutical Company); Remikirin (RO42-5892, F. Hoffman LaRoche AG); $A_2$ agonists (Marion Merrill Dow) and certain non-peptide heterocycles (G.D.Searle and Company).

"Angiotensin converting enzyme (ACE), is an enzyme which catalyzes the conversion of angiotensin I to angiotensin II. ACE inhibitors include amino acids and derivatives thereof, peptides, including di and tri peptides and antibodies to ACE which intervene in the renin-angiotensin system by inhibiting the activity of ACE thereby reducing or eliminating the formation of pressor substance angiotensin II. ACE inhibitors have been used medically to treat hypertension, congestive heart failure, myocardial infarction and renal disease. Classes of compounds known to be useful as ACE inhibitors include acylmercapto and mercaptoalkanoyl prolines such as captopril (U.S. Pat. No. 4,105,776) and zofenopril (U.S. Pat. No. 4,316,906), carboxyalkyl dipeptides such as enalapril (U.S. Pat. No. 4,374,829), lisinopril (U.S. Pat. No. 4,374,829), quinapril (U.S. Pat. No. 4,344,949), ramipril (U.S. Pat. No. 4,587,258), and perindopril (U.S. Pat. No. 4,508,729), carboxyalkyl dipeptide mimics such as cilazapril (U.S. Pat. No. 4,512,924) and benazapril (U.S. Pat. No. 4,410,520), phosphinylalkanoyl prolines such as fosinopril (U.S. Pat. No. 4,337,201) and trandolopril.

"Renin inhibitors" are compounds which interfere with the activity of renin. Renin inhibitors include amino acids and derivatives thereof, peptides and derivatives thereof, and antibodies to renin. Examples of renin inhibitors that are the subject of United States patents are as follows: urea derivatives of peptides (U.S. Pat. No. 5,116,835); amino acids connected by nonpeptide bonds (U.S. Pat. No. 5,114,937); di and tri peptide derivatives (U.S. Pat. No. 5,106,835); amino acids and derivatives thereof (U.S. Pat. Nos. 5,104,869 and 5,095,119); diol sulfonamides and sulfinyls (U.S. Pat. No. 5,098,924); modified peptides (U.S. Pat. No. 5,095,006); peptidyl beta-aminoacyl aminodiol carbamates (U.S. Pat. No. 5,089,471); pyrolimidazolones (U.S. Pat. No. 5,075,451); fluorine and chlorine statine or statone containing peptides (U.S. Pat. No. 5,066,643); peptidyl amino diols (U.S. Pat. Nos. 5,063,208 and 4,845,079); N-morpholino derivatives (U.S. Pat. No. 5,055,466); pepstatin derivatives (U.S. Pat. No. 4,980,283); N-heterocyclic alcohols (U.S. Pat. No. 4,885,292); monoclonal antibodies to renin (U.S. Pat. No. 4,780,401); and a variety of other peptides and analogs thereof (U.S. Pat. Nos. 5,071,837, 5,064,965, 5,063,207, 5,036,054, 5,036,053, 5,034,512, and 4,894,437).

Agents that bind to cellular adhesion molecules and inhibit the ability of white blood cells to attach to such molecules include polypeptide agents. Such polypeptides include polyclonal and monoclonal antibodies, prepared according to conventional methodology. Such antibodies already are known in the art and include anti-ICAM 1 antibodies as well as other such antibodies. Significantly, as is well-known in the art, only a small portion of an antibody molecule, the paratrope, is involved in the binding of the antibody to its epitope (see, in general, Clark, W. R. (1986) *The Experimental Foundations of Modern Immunology*, Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd Fragment may be associated with up to ten different light chains without altering antibody specificity) and Fd fragments retain epitope-binding ability in isolation.

Within the antigen-binding portion of an antibody, as is well-know in the art, there are complementarity determining regions (CDRs), which directly interact with the epitope of the antigen, and framework regions (Frs), which maintain the tertiary structure of the paratope (see, in general, Clar, 1986; Roitt, 1991). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for $F(ab')_2$, Fab, Fv and Fd fragments; chimeric antibodies in which the Fc and/or Fr and/or CDR1 and/or CDR2 and/or light chain CDR3 regions have been replaced by homologous human or non-human sequences; chimeric $F(ab')_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or nonhuman sequences. The present invention also includes so-called single chain antibodies.

Thus, the invention involves polypeptides of numerous size and type that bind specifically to cellular adhesion molecules. These polypeptides may be derived also from sources other than antibody technology. For example, such polypeptide binding agents can be provided by degenerate peptide libraries which can be readily prepared in solution, in immobilized form or as phage display libraries. Combinatorial libraries also can be synthesized of peptides containing one or more amino acids. Libraries further can be synthesized of peptoids and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to the cellular adhesion molecule. This process can be repeated through several cycles of reselection of phage that bind to the cellular adhesion molecule. Repeated rounds lead to enrichment of phage bearing particular sequences. DNA sequences analysis can be conducted to identify the sequences of the expressed polypeptides. The minimal linear portion of the sequence that binds to the cellular adhesion molecule can be determined. One can repeat the procedure using a biased library containing inserts containing part of all of the minimal linear portion plus one or more additional degenerate residues upstream or downstream thereof. Yeast two-hybrid screening methods also may be used to identify polypeptides that bind to the cellular adhesion molecules. Thus, cellular adhesion molecules, or a fragment thereof, can be used to screen peptide libraries, including phage display libraries, to identify and select peptide binding partners of the cellular adhesion molecules.

An "infection" or "infectious disease" as used herein, refers to a disorder arising from the invasion of a host, superficially, locally, or systemically, by an infectious microorganism. Infectious microorganisms include bacteria, viruses, parasites and fungi. The term "sepsis" refers to the clinical condition in which infective agents (bacteria, pathogenic fungi) or products of infection (bacterial toxins) enter the blood circulation and profoundly affects the patient's blood pressure, heart rate, and body temperature.

Bacteria are unicellular organisms which multiply asexually by binary fission. They are classified and named based on their morphology, staining reactions, nutrition and metabolic requirements, antigenic structure, chemical composition, and genetic homology. Bacteria can be classified into three groups based on their morphological forms, spherical (*coccus*), straight-rod (*bacillus*) and curved or spiral rod (*vibrio, campylobacter, spirillum*, and *spirochaete*). Bacteria are also more commonly characterized based on their staining reactions into two classes of organisms, gram-positive and gram-negative. Gram refers to the method of staining which is commonly performed in microbiology labs. Gram-positive organisms retain the stain following the staining procedure and appear a deep violet color. Gram-negative organisms do not retain the stain but take up the counter-stain and thus appear pink.

Bacteria have two main structural components, a rigid cell wall and protoplast (material enclosed by the cell wall). The protoplast includes cytoplasm and genetic material. Surrounding the protoplast is the cytoplasmic membrane which includes some of the cell respiratory enzymes and is responsible for the permeability of bacteria and transport of many small molecular weight substances. The cell wall surrounding the cytoplasmic membrane and protoplast is composed of mucopeptides which include complex polymers of sugars cross-linked by peptide chains of amino acids. The wall is also composed of polysaccharides and teichoic acids.

Infectious bacteria include, but are not limited to, gram negative and gram positive bacteria. Gram positive bacteria include, but are not limited to *Pasteurella* species, *Staphylococci* species, and *Streptococcus* species. Gram negative bacteria include, but are not limited to, *Escherichia coli*, *Pseudomonas* species, and *Salmonella* species. Specific examples of infectious bacteria include but are not limited to: *Helicobacter pyloris*, *Borelia burgdorferi*, *Legionella pneumophilia*, *Mycobacteria* species (e.g. *M. tuberculosis*, *M. avium*, *M. intracellulare*, *M. kansaii*, *M. gordonae*), *Staphylococcus aureus*, *Neisseria gonorrhoeae*, *Neisseria meningitidis*, *Listeria monocytogenes*, *Streptococcus pyogenes* (Group A *Streptococcus*), *Streptococcus agalactiae* (Group B *Streptococcus*), *Streptococcus* (viridans group), *Streptococcus faecalis*, *Streptococcus bovis*, *Streptococcus* (anaerobic species), *Streptococcus pneumoniae*, pathogenic *Campylobacter* species, *Enterococcus* species, *Haemophilus influenzae*, *Bacillus antracis*, *Corynebacterium diphtheriae*, *Erysipelothrix rhusiopathiae*, *Clostridium perfringers*, *Clostridium tetani*, *Enterobacter aerogenes*, *Klebsiella pneumoniae*, *Pasturella multocida*, *Bacteroides* species, *Fusobacterium nucleatum*, *Streptobacillus moniliformis*, *Treponema pallidium*, *Treponema pertenue*, *Leptospira* species, *Rickettsia* species, and *Actinomyces israelli*. Additional exemplary bacteria are *Mycoplasma*, e.g. *Mycoplasma pneumoniae*, *Chlamydophila*, e.g. *Chlamydophila pneumoniae*, *Bartonella* species, and *Tropheryma whippelii*.

Viruses are small infectious agents which contain a nucleic acid core and a protein coat, but are not independently living organisms. A virus cannot survive in the absence of a living cell within which it can replicate. Viruses enter specific living cells either by endocytosis or direct injection of DNA (phage) and multiply, causing disease. The multiplied virus can then be released and infect additional cells. Some viruses are DNA-containing viruses and other are RNA-containing viruses.

Once the virus enters the cell it can cause a variety of physiological effects. One effect is cell degeneration, in which the accumulation of virus within the cell causes the cell to die and break into pieces and release the virus. Another effect is cell fusion, in which infected cells fuse with neighboring cells to produce syncytia. Other types of virus cause cell proliferation which results in tumor formation.

Specific examples of viruses that have been found in humans include but are not limited to: Retroviridae (e.g. human immunodeficiency viruses, such as HIV-1 (also referred to as HTLV-III, LAV or HTLV-III/LAV, or HIV-III); and other isolates, such as HIV-LP); Picornaviridae (e.g. polio viruses, hepatitis A virus; enteroviruses, human Coxsackie viruses, rhinoviruses, echoviruses); Calciviridae (e.g. strains that cause gastroenteritis); Togaviridae (e.g. equine encephalitis viruses, rubella viruses); Flaviridae (e.g. dengue viruses, encephalitis viruses, yellow fever viruses); Coronoviridae (e.g. coronaviruses); Rhabdoviradae (e.g. vesicular stomatitis viruses, rabies viruses); Filoviridae (e.g. ebola viruses); Paramyxoviridae (e.g. parainfluenza viruses, mumps virus, measles virus, respiratory syncytial virus); Orthomyxoviridae (e.g. influenza viruses); Bunyaviridae (e.g. Hantaan viruses, bunyaviruses, phleboviruses and Nairo viruses); Arenaviridae hemorrhagic fever viruses); Reoviridae (e.g. reoviruses, orbiviurses and rotaviruses); Birnaviridae; Hepadnaviridae (Hepatitis B virus); Parvovirida (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes virus); Poxyiridae (variola viruses, vaccinia viruses, pox viruses); and Iridoviridae (e.g. African swine fever virus); and unclassified viruses (e.g., the agent of delta hepatitis (thought to be a defective satellite of hepatitis B virus), the agents of non-A, non-B hepatitis (class 1=internally transmitted; class 2=parenterally transmitted (i.e. Hepatitis C); Norwalk and related viruses, and astroviruses).

In addition to viruses that infect human subjects causing human disorders, the invention is also useful for treating other non-human vertebrates. Non-human vertebrates are also capable of developing infections which can be prevented or treated with the combinations of aziridino compounds and anti-microbials disclosed herein. For instance, in addition to the treatment of infectious human diseases, the methods of the invention are useful for treating or preventing infections of non-human animals.

Infectious virus of both human and non-human vertebrates, include retroviruses, RNA viruses and DNA viruses. This group of retroviruses includes both simple retroviruses and complex retroviruses. The simple retroviruses include the subgroups of B-type retroviruses, C-type retroviruses and D-type retroviruses. An example of a B-type retrovirus is mouse mammary tumor virus (MMTV). The C-type retroviruses include subgroups C-type group A (including Rous sarcoma virus (RSV), avian leukemia virus (ALV), and avian myeloblastosis virus (AMV)) and C-type group B (including murine leukemia virus (MLV), feline leukemia virus (FeLV), murine sarcoma virus (MSV), gibbon ape leukemia virus (GALV), spleen necrosis virus (SNV), reticuloendotheliosis virus (RV) and simian sarcoma virus (SSV)). The D-type retroviruses include Mason-Pfizer monkey virus (MPMV) and simian retrovirus type 1 (SRV-1). The complex retroviruses include the subgroups of lentiviruses, T-cell leukemia viruses and the foamy viruses. Lentiviruses include HIV-1, but also include HIV-2, SIV, Visna virus, feline immunodeficiency virus (FIV), and equine infectious anemia virus (EIAV). The T-cell leukemia viruses include HTLV-1, HTLV-II, simian T-cell leukemia virus (STLV), and bovine leukemia virus (BLV). The foamy viruses include human foamy virus (HFV), simian foamy virus (SFV) and bovine foamy virus (BFV).

Examples of other RNA viruses that are pathogens in vertebrate animals include, but are not limited to, the following: members of the family Reoviridae, including the genus Orthoreovirus (multiple serotypes of both *mammalian* and *avian* retroviruses), the genus Orbivirus (Bluetongue virus, Eugenangee virus, Kemerovo virus, African horse sickness virus, and Colorado Tick Fever virus), the genus *Rotavirus* (human *rotavirus*, Nebraska calf diarrhea virus, murine *rotavirus*, simian *rotavirus*, bovine or ovine *rotavirus, avian rotavirus*); the family Picornaviridae, including the genus *Enterovirus* (poliovirus, Coxsackie virus A and B, enteric cytopathic human orphan (ECHO) viruses, hepatitis A virus, Simian enteroviruses, Murine encephalomyelitis (ME) viruses, *Poliovirus muris, Bovine enteroviruses, Porcine enteroviruses*, the genus *Cardiovirus* (Encephalomyocarditis virus (EMC), Mengovirus), the genus *Rhinovirus* (Human rhinoviruses including at least 113 subtypes; other rhinoviruses), the genus *Apthovirus* (Foot and Mouth disease (FMDV); the family Calciviridae, including Vesicular exanthema of swine virus, San Miguel sea lion virus, *Feline picornavirus* and Norwalk virus; the family Togaviridae, including the genus *Alphavirus* (Eastern equine encephalitis virus, Semliki forest virus, Sindbis virus, Chikungunya virus, O'Nyong-Nyong virus, Ross river virus, Venezuelan equine encephalitis virus, Western equine encephalitis virus), the genus *Flavirus* (Mosquito borne yellow fever virus, Dengue virus, Japanese encephalitis virus, St. Louis encephalitis virus, Murray Valley encephalitis virus, West Nile virus, Kunjin virus, Central European tick borne virus, Far Eastern tick borne virus, Kyasanur forest virus, Louping III virus, Powassan virus, Omsk hemorrhagic fever virus), the genus *Rubivirus* (Rubella virus), the genus *Pestivirus* (Mucosal disease virus, Hog cholera virus, Border disease virus); the family Bunyaviridae, including the genus *Bunyavirus* (Bunyamwera and related viruses, California encephalitis group viruses), the genus *Phlebovirus* (Sandfly fever Sicilian virus, Rift Valley fever virus), the genus *Nairovirus* (Crimean-Congo hemorrhagic fever virus, Nairobi sheep disease virus), and the genus *Uukuvirus* (Uukuniemi and related viruses); the family Orthomyxoviridae, including the genus *influenza virus* (influenza virus type A, many human subtypes); Swine *influenza virus*, and Avian and Equine *Influenza viruses*; influenza type B (many human subtypes), and influenza type C (possible separate genus); the family Paramyxoviridae, including the genus *Paramyxovirus* (Parainfluenza virus type 1, Sendai virus, Hemadsorption virus, Parainfluenza viruses types 2 to 5, Newcastle Disease Virus, Mumps virus), the genus *Morbillivirus* (Measles virus, subacute sclerosing panencephalitis virus, distemper virus, Rinderpest virus), the genus *Pneumovirus* (respiratory syncytial virus (RSV), Bovine respiratory syncytial virus and Pneumonia virus of mice); the family Rhabdoviridae, including the genus *Vesiculovirus* (VSV), Chandipura virus, Flanders-Hart Park virus), the genus *Lyssavirus* (Rabies virus), fish Rhabdoviruses, and two probable Rhabdoviruses (Marburg virus and Ebola virus); the family Arenaviridae, including Lymphocytic choriomeningitis virus (LCM), Tacaribe virus complex, and Lassa virus; the family Coronoaviridae, including Infectious Bronchitis Virus (IBV), Mouse Hepatitis virus, Human enteric corona virus, and Feline infectious peritonitis (Feline coronavirus).

Illustrative DNA viruses that infect vertebrate animals include, but are not limited to: the family Poxyiridae, including the genus *Orthopoxvirus* (*Variola major, Variola minor*, Monkeypox, Vaccinia, Cowpox, Buffalopox, Rabbitpox, Ectromelia), the genus *Leporipoxvirus* (Myxoma, Fibroma), the genus *Avipoxvirus* (Fowlpox, other avian poxvirus), the genus *Capripoxvirus* (sheeppox, goatpox), the genus *Suipoxvirus* (Swinepox), the genus *Parapoxvirus* (contagious postular dermatitis virus, pseudocowpox, bovine papular stomatitis virus); the family Iridoviridae (African swine fever virus, Frog viruses 2 and 3, Lymphocystis virus of fish); the family Herpesviridae, including the alpha-Herpesviruses (Herpes Simplex Types 1 and 2, Varicella-Zoster, Equine abortion virus, Equine herpes virus 2 and 3, pseudorabies virus, infectious bovine keratoconjunctivitis virus, infectious bovine rhinotracheitis virus, feline rhinotracheitis virus, infectious laryngotracheitis virus) the Beta-herpesviruses (Human cytomegalovirus and cytomegaloviruses of swine, monkeys and rodents); the gamma-herpesviruses (Epstein-Barr virus (EBV), Marek's disease virus, Herpes saimiri, Herpesvirus ateles, Herpesvirus sylvilagus, guinea pig herpes virus, Lucke tumor virus); the family Adenoviridae, including the genus *Mastadenovirus* (Human subgroups A,B,C,D,E and ungrouped); simian adenoviruses (at least 23 serotypes), infectious canine hepatitis, and adenoviruses of cattle, pigs, sheep, frogs and many other species, the genus *Aviadenovirus* (*Avian* adenoviruses); and non-cultivatable adenoviruses; the family Papoviridae, including the genus *Papillomavirus* (Human papilloma viruses, bovine papilloma viruses, Shope rabbit papilloma virus, and various pathogenic papilloma viruses of other species), the genus *Polyomavirus* (polyomavirus, Simian vacuolating agent (SV-40), Rabbit vacuolating agent (RKV), K virus, BK virus, JC virus, and other primate polyoma viruses such as Lymphotrophic papilloma virus); the family Parvoviridae including the genus Adeno-associated viruses, and the genus *Parvovirus* (Feline panleukopenia virus, bovine parvovirus, canine parvovirus, Aleutian mink disease virus, etc).

Parasites are organisms which depend upon other organisms in order to survive and thus must enter, or infect, another organism to continue their life cycle. The infected organism, i.e., the host, provides both nutrition and habitat to the parasite. The term "parasite" as used herein refers to protozoa, helminths, and ectoparasitic arthropods (e.g., ticks, mites, etc.). Protozoa are single celled organisms which can replicate both intracellularly and extracellularly, particularly in the blood, intestinal tract or the extracellular matrix of tissues. Helminths are multicellular organisms which almost always are extracellular (the exception being *Trichinella*). Helminths normally require exit from a primary host and transmission into a secondary host in order to replicate. In contrast to these aforementioned classes, ectoparasitic arthropods form a parasitic relationship with the external surface of the host body.

Parasites can be classified based on whether they are intracellular or extracellular. An "intracellular parasite" as used herein is a parasite whose entire life cycle is intracellular. Examples of human intracellular parasites include *Leishmania, Plasmodium, Trypanosoma cruzi, Toxoplasma gondii, Babesia*, and *Trichinella spiralis*. An "extracellular parasite" as used herein is a parasite whose entire life cycle is extracellular. Extracellular parasites capable of infecting humans include *Entamoeba histolytica, Giardia lamblia, Enterocytozoon bieneusi, Naegleria* and *Acanthamoeba* as well as most helminths. Yet another class of parasites is defined as being mainly extracellular but with an obligate intracellular existence at a critical stage in their life cycles. Such parasites are referred to herein as "obligate intracellular parasites". These parasites may exist most of their lives or only a small portion of their lives in an extracellular environment, but they all have at lest one obligate intracellular stage in their life cycles. This latter category of parasites includes *Trypanosoma rhodesiense* and *Trypanosoma gambiense, Isospora, Cryptosporidium, Eimeria, Neospora, Sarcocystis*, and *Schistosoma*. In one aspect, the invention relates to the prevention and treatment of infection resulting from intracellular parasites and obligate intracellular parasites which have at least in one stage of their life cycle that is intracellular. In some embodiments, the invention is directed to the prevention of infection from obligate intracellular parasites which are predominantly intracellular. An exemplary and non-limiting list of parasites for some aspects of the invention is provided herein.

Blood-borne and/or tissues parasites include *Plasmodium, Babesia microti, Babesia divergens, Leishmania tropica, Leishmania, Leishmania braziliensis, Leishmania donovani, Trypanosoma gambiense* and *Trypanosoma rhodesiense* (African sleeping sickness), *Trypanosoma cruzi* (Chagas' disease), and *Toxoplasma gondii*. Typical parasites infecting horses are *Gasterophilus; Eimeria leuckarti, Giardia; Tritrichomonas equi; Babesia* (RBCs), *Theileria equi; Trypanosoma; Klossiella equi; Sarcocystis*.

Typical parasites infecting swine include *Eimeria bebliecki, Eimeria scabra, Isospora suis, Giardia; Balantidium coli, Entamoeba histolytica; Toxoplasma gondii* and *Sarcocystis*, and *Trichinella spiralis*.

The major parasites of dairy and beef cattle include *Eimeria, Cryptosporidium, Giardia; Toxoplasma gondii; Babesia* bovis (RBCs), *Babesia bigemina* (RBCs), *Trypanosoma* (plasma), *Theileria* (RBC); *Theileria parva* (lymphocytes); *Tritrichomonas foetus*; and *Sarcocystis*.

Typical parasites infecting sheep and goats include *Eimeria, Cryptosporidium, Giardia; Toxoplasma gondii; Babesia* (RBC), *Trypanosoma* (plasma), *Theileria* (RBC); and *Sarcocystis*.

Typical parasitic infections in poultry include coccidiosis caused by *Eimeria acervulina, E. necatrix, E. tenella, Isospora* and *Eimeria truncata*; histomoniasis, caused by *Histomonas meleagridis* and *Histomonas gallinarum*; trichomoniasis caused by *Trichomonas gallinae*; and hexamitiasis caused by *Hexamita meleagridis*. Poultry can also be infected *Emeria maxima, Emeria meleagridis, Eimeria adenoeides, Eimeria meleagrimitis, Cryptosporidium, Eimeria brunetti, Emeria adenoeides, Leucocytozoon, Plasmodium, Hemoproteus meleagridis, Toxoplasma gondii* and *Sarcocystis*.

Parasitic infections also pose serious problems in laboratory research settings involving animal colonies. Some examples of laboratory animals intended to be treated, or in which parasite infection is sought to be prevented, by the methods of the invention include mice, rats, rabbits, guinea pigs, nonhuman primates, as well as the aforementioned swine and sheep.

Typical parasites in mice include *Leishmania, Plasmodium berghei, Plasmodium yoelii, Giardia muris, Hexamita muris; Toxoplasma gondii; Trypanosoma duttoni* (plasma); *Klossiella muris; Sarcocystis*. Typical parasites in rats include *Giardia muris, Hexamita muris; Toxoplasma gondii; Trypanosoma lewisi* (plasma); *Trichinella spiralis*; and *Sarcocystis*. Typical parasites in rabbits include *Eimeria; Toxoplasma gondii; Nosema cuniculi; Eimeria stiedae*, and *Sarcocystis*. Typical parasites of the hamster include *Trichomonas; Toxoplasma gondii; Trichinella spiralis*; and *Sarcocystis*. Typical parasites in the guinea pig include *Balantidium caviae; Toxoplasma gondii; Klossiella caviae*; and *Sarcocystis*.

Fungi are eukaryotic organisms, only a few of which cause infection in vertebrate mammals. Because fungi are eukaryotic organisms, they differ significantly from prokaryotic bacteria in size, structural organization, life cycle and mechanism of multiplication. Fungi are classified generally based on morphological features, modes of reproduction and culture characteristics. Although fungi can cause different types of disease in subjects, such as respiratory allergies following inhalation of fungal antigens, fungal intoxication due to ingestion of toxic substances, such as amatatoxin and phallotoxin produced by poisonous mushrooms and aflotoxins, produced by aspergillus species, not all fungi cause infectious disease.

Infectious fungi can cause systemic or superficial infections. Primary systemic infection can occur in normal healthy subjects and opportunistic infections, are most frequently found in immuno-compromised subjects. The most common fungal agents causing primary systemic infection include *Blastomyces, Coccidioides*, and *Histoplasma*. Common fungi causing opportunistic infection in immuno-compromised or immunosuppressed subjects include, but are not limited to, *Candida albicans* (an organism which is normally part of the respiratory tract flora), *Cryptococcus neoformans* (sometimes in normal flora of respiratory tract), and various *Aspergillus* species. Systemic fungal infections are invasive infections of the internal organs. The organism usually enters the body through the lungs, gastrointestinal tract, or intravenous lines. These types of infections can be caused by primary pathogenic fungi or opportunistic fungi.

Superficial fungal infections involve growth of fungi on an external surface without invasion of internal tissues. Typical superficial fungal infections include cutaneous fungal infections involving skin, hair, or nails. An example of a cutaneous infection is *Tinea* infections, such as ringworm, caused by *Dermatophytes*, such as *Microsporum* or *Traicophyton* species, i.e., *Microsporum canis, Microsporum gypsum, Tricofitin rubrum*. Examples of fungi include: *Cryptococcus neoformans, Histoplasma capsulatum, Coccidioides immitis, Blastomyces dermatitidis, Chlamydia trachomatis, Candida albicans*.

Diseases associated with fungal infection include aspergillosis, blastomycosis, camdidiais, chromoblastomycosis, coccidioidomycosis, cryptococcosis, fungal eye infections, fungal hair, nail, and skin infections, histoplasmosis, lobomycosis, mycetoma, otomycosis, paracoccidioidomycosis, penicilliosis, marneffeii, phaeohyphomycosis, rhinosporidioisis, sporotrichosis, and zygomycosis.

Aspergillosis is a disease caused by the fungi of the genus *Aspergillus*, which can lead to mild or severe disease, generally depending on factors such as the status of the host immune system. *Aspergillus* frequently arises as an opportunistic infection in patients having immune-suppressive diseases, or being treated with chemotherapy. Some forms of *aspergillus* can be treated with prednisone, disodium chromoglycat, nystatin, amphotericin B, itraconazole, or voriconazole.

Blastomycosis is a fungal infection arising from the organism *Blastomyces dermatitis*. The infection initiates in the lungs and usually is disseminated to other body sites, especially the skin and bone. It is treated by amphotericin B, hydroxystilbamidine, itraconazole and voriconazole. When amphotericin B is used, at least 1.5 grams must be given to avoid relapse. However, when the drug is administered in combination with the aziridino compounds, lower doses can be given without a relapse. Generally hydroxystilbamidine has been used for treating the cutaneous form of the disease but not other forms. When combined with aziridino compounds in the combination compositions of the invention, it can also be used for the treatment of other forms, as well as in lower doses for the cutaneous form.

Candidiasis is a fungal infection caused by a member of the genus *Candida*. The disease can be in the form of allergic, cutaneous, mucocutaneous, or systemic candidiasis. Nystatin is used for the treatment of the cutaneous, mucocutaneous, and allergic diseases. Amphotericin B is useful for treating this systemic disease. Other drugs useful for the treatment include 5-fluorocytosine, fluconazole, itraconazole and voriconazole.

Chromoblastomycosis is a chronic infection of the skin and subcutaneous tissue. Although the infection is usually localized, parts can disseminate systemically and in particular to the brain. Itraconazole and terbinafine are the drugs used to treat this infection. The principal fungi causing this infection are *Cladophialophora, Carrionii, Fonsecaea, Compacta, Fonsecaeapedrosoi, Phialophora, Verruceosa, Rhinocladiella*, and *Aquasbera*.

Coccidioidomycosis is a fungal disease of the respiratory tract which can be acute, chronic, severe or fatal. The disease is primarily caused by *Coccidioides immitis*. Amphotericin B, itraconazole, fluconazole, ketaconazole, and voriconazole are anti-fungal agents that are used for the treatment of this disorder.

Cryptococcosis is a fungal disorder caused by *Cryptococcus norformans* or *Filobasidiella neoformans*. The disease can take the form of a chronic, subacute, acute, pulmonary, systemic, or meningitic disease, following primary infection in the lungs. If the disease spreads from the lungs to the central nervous system, it is usually treated immediately with amphotericin B and/or 5-fluorocytosine and in some cases fluconazole.

Fungal infections of the eye include mycotic keratitis, and endogenous or extension oculomycosis. Mycotic keratitis is caused by a variety of fungi including *Acremonium, Aspergillus, Bipolaris, Candida albicans, Curvularia, Exserohilum, Fusarium*, and *Lasiodiplodia*. Amphotericin B is not used for treatment because it irritates the infected tissue. Drugs useful for treating mycotic keratitis include pimaricin and fluconazole. Oculomycosis is generally caused by *Candida albicans* or rhizopus, arrhizus. Amphotericin B is the anti-fungal agent used for treatment.

Fungal infections of the hair, nail, and skin include onychomycosis, piedra, pityriasis versicolor, tinea barbae, tinea capitis, tinea corporis, tinea cruris, tinea faosa, tinea nigra, tinea unguium. Onychomycosis, which is generally caused by fungi such as *Acremonium, Aspergillus, Candida, Fusarium, Scopulariopsis, Onychocola*, and *Scytalidium*, can be treated with itraconazole, turbinifine, amphotericin B, gentian violet, resorcin, iodine, nystatin, thiabendazole, and glutarardeyde. Piedra, which is a colonization of the hair shaft to bifungal organisms such as *Piedraia* and *Trichosporin*, can be treated with keratolytic agents, mild fungicides, fluconazole, and itraconazole. The tineas are various forms of ringworm colonizing different bodily regions. These diseases are generally caused by fungi such as *Microsporum, Trichophyton*, and *Epidermophyton*. The tineas can be treated with keratolytic agents, intraconazole, turbinifine, tolnaftate, clotrimazole, miconazole, econazole, and ketaconzole.

Histoplasmosis (*capsulati* and *duboisii*) are fungal infections caused by *Histoplasma* and *Ajellomyces*. *Histoplasmosis capsulati* can adequately be treated with amphotericin B, itraconazole or voriconazole. If the subject being treated has AIDS, fluconazole is usually used. *Histoplasmosis duboisii* once it becomes disseminated, especially to the liver or spleen, is very difficult to treat. Amphotericin B, itraconazole, fluconazole, and voriconazole are used. When these compounds are combined with the aziridino compounds of the invention, prognosis is improved.

Lobomycosis is a fungal infection caused by *Lacazia loboi*. Lobomycosis is a cutaneous infection which develops into lesions which can be removed by surgery. There are not drugs specifically used for this disorder. Mycetoma is an infection caused by a variety of fungi including *Eumycotic, Acromonium, Aspergillus, Exophiala, Leptos Phaeria, Madurella, Neotestudina, Pseudallesheria*, and *Pyrenochieta*. The disease involves lesions of the cutaneous and subcutaneous tissues, which can rupture and spread to surrounding tissues. The mycetomas can be treated with ketoconazole, in combination with surgery.

Otomycosis is a fungal ear infection caused by *Aspergillus* or *candida*. The infection is a superficial infection of the outer ear canal, which is characterized by inflammation, pruritus, scaling, and sever discomfort. It is a chronic recurring mycosis.

Paracoccidioidomycosis is a fungal infection cause by *Paracoccidioides brasiliensis*. The disease originates as a pulmonary infection and can disseminate into the nasal, buccal, and gastrointestinal mucosa. Amphotericin B and sulfonamides are generally used to treat the disease.

Phaeohyphomycosis is a fungal infection caused by a variety of fungi including *Cladophialophora, Curvularia, Bipolaris, Exserohilum, Exophiala, Scedosporium, Ochroconis, Coniothyrium, Phialophora, Wangiella*, and *Lasiodiplodia*. The infection can be localized or can invade various tissues including the brain, bone, eyes, and skin. Invasion of the brain or bone can be lethal. Generally, phaeohyphomycosis is treated with amphotericin B and phyfluorocytozine or intaconazole. *Rhinosporidiosis* is an infection of the mucus membrane caused by *Rhinosporidium seeberi*. Local injection of amphotericin B is used as treatment.

Sporotrichosis is a chronic infection of the cutaneous tissues, subcutaneous tissues, or lymph system. The infection may also spread to tissues such as bone, muscle, CNS, lungs, and/or genitourinary system. Usually the fungi *Sporothrix schenckii* is inhaled or passed through a lesion in the skin. Sporotrichosis is usually treated with oral potassium iodide, amphotericin B, or 5-fluorocytozine.

Zygomycosis is a chronic infection caused by *Conidobolus* and *Basidiobolus ranarum*. The disease is treated by potassium iodide and/or amphotericin B.

Other medically relevant microorganisms and the diseases they cause have been described extensively in the literature, e.g., see C. G. A. Thomas, *Medical Microbiology*, Bailliere Tindall, Great Britain 1983, the entire contents of which is hereby incorporated by reference. Each of the foregoing lists is illustrative, and is not intended to be limiting.

The methods of the invention involve, in some aspects, combinations of compounds that are inhibitors of cellular necrosis (e.g., heterocyclic thiohydantoin, hydantoin, oxazolidinone, thioxo-oxazolidinone, pyrimidinone, or oxazinanone compounds, or combinations thereof) with anti-microbial agents for the treatment or prevention of infectious disease. An "anti-microbial agent", as used herein, refers to a naturally-occurring or synthetic compound which is capable of killing or inhibiting infectious microorganisms. The type of anti-microbial agent useful according to the invention will depend upon the type of microorganism with which the subject is infected or at risk of becoming infected. It is contemplated that several different kinds of anti-microbial agents can be combined with the aziridino compounds to make compositions useful for treating multifactorial diseases (e.g., HIV infection with opportunistic fungal infections).

One type of anti-microbial agent is an antibacterial agent. Antibacterial agents kill or inhibit the growth or function of bacteria. A large class of antibacterial agents is antibiotics. Antibiotics, which are effective for killing or inhibiting a wide range of bacteria, are referred to as broad spectrum antibiotics. Other types of antibiotics are predominantly effective against the bacteria of the class gram-positive or gram-negative. These types of antibiotics are referred to as narrow spectrum antibiotics. Other antibiotics which are effective against a single organism or disease and not against other types of bacteria, are referred to as limited spectrum antibiotics.

Antibacterial agents are sometimes classified based on their primary mode of action. In general, antibacterial agents are cell wall synthesis inhibitors, cell membrane inhibitors, protein synthesis inhibitors, nucleic acid synthesis or functional inhibitors, and competitive inhibitors. Cell wall synthesis inhibitors inhibit a step in the process of cell wall synthesis, and in general in the synthesis of bacterial peptidoglycan. Cell wall synthesis inhibitors include β-lactam antibiotics, natural penicillins, semi-synthetic penicillins, ampicillin, clavulanic acid, cephalolsporins, and bacitracin.

The β-lactams are antibiotics containing a four-membered β-lactam ring which inhibits the last step of peptidoglycan synthesis. β-lactam antibiotics can be synthesized or natural. The natural antibiotics are generally produced by two groups of fungi, *Penicillium* and *Cephalosporium* molds. The β-lactam antibiotics produced by *Penicillium* are the natural penicillins, such as penicillin G or penicillin V. These are produced by fermentation of *Penicillium chrysogenum*. The natural penicillins have a narrow spectrum of activity and are generally effective against *Streptococcus, Gonococcus*, and *Staphylococcus*. Other types of natural penicillins, which are also effective against gram-positive bacteria, include penicillins F, X, K, and O.

Semi-synthetic penicillins are generally modifications of the molecule 6-aminopenicillanic acid produced by a mold. The 6-aminopenicillanic acid can be modified by addition of side chains which produce penicillins having broader spectrums of activity than natural penicillins or various other advantageous properties. Some types of semi-synthetic penicillins have broad spectrums against gram-positive and gram-negative bacteria, but are inactivated by penicillinase. These semi-synthetic penicillins include ampicillin, carbenicillin, oxacillin, azlocillin, mezlocillin, and piperacillin. Other types of semi-synthetic penicillins have narrower activities against gram-positive bacteria, but have developed properties such that they are not inactivated by penicillinase. These include, for instance, methicillin, dicloxacillin, and nafcillin. Some of the broad spectrum semi-synthetic penicillins can be used in combination with β-lactamase inhibitors, such as clavulanic acids and sulbactam. The β-lactamase inhibitors do not have anti-microbial action but they function to inhibit penicillinase, thus protecting the semi-synthetic penicillin from degradation.

Another type of β-lactam antibiotic is the cephalosporins. Cephalosporins are produced by *Cephalosporium* molds, and have a similar mode of action to penicillin. They are sensitive to degradation by bacterial β-lactamases, and thus, are not always effective alone. Cephaloisporins, however, are resistant to penicillinase. They are effective against a variety of gram-positive and gram-negative bacteria. Cephalolsporins include, but are not limited to, cephalothin, cephapirin, cephalexin, cefamandole, cefaclor, cefazolin, cefuroxine, cefoxitin, cefotaxime, cefsulodin, cefetamet, cefixime, ceftriaxone, cefoperazone, ceftazidine, and moxalactam.

Bacitracin is another class of antibiotics which inhibit cell wall synthesis. These antibiotics, produced by *Bacillus* species, prevent cell wall growth by inhibiting the release of muropeptide subunits or peptidoglycan from the molecule that delivers the subunit to the outside of the membrane. Although bacitracin is effective against gram-positive bacteria, its use is limited in general to topical administration because of its high toxicity. Since lower effective doses of bacitracin can be used when the compound is administered with the aziridino compounds in accordance with the invention, this compound can be used systemically and the toxicity reduced.

Carbapenems are another type of broad spectrum β-lactam antibiotic, which is capable of inhibiting cell wall synthesis. Examples of carbapenems include, but are not limited to, imipenems. Monobactems are also broad spectrum β-lactam antibiotics, and include, euztreonam. An antibiotic produced by *Streptomyces*, vancomycin, is also effective against gram-positive bacteria by inhibiting cell membrane synthesis.

Another class of anti-bacterial agents is the anti-bacterial agents that are cell membrane inhibitors. These compounds disorganize the structure or inhibit the function of bacterial membranes. Alteration of the cytoplasmic membrane of bacteria results in leakage of cellular materials from the cell. Compounds that inhibit or interfere with the cell membrane cause death of the cell because the integrity of the cytoplasmic and outer membranes is vital to bacteria. One problem with anti-bacterial agents that are cell membrane inhibitors is that they can produce effects in eukaryotic cells as well as bacteria because of the similarities in phospholipids in bacterial and eukaryotic membranes. Thus these compounds are rarely specific enough to permit these compounds to be used systemically and prevent the use of high doses for local administration.

One clinically useful anti-bacterial agent that is a cell membrane inhibitor is Polymyxin, produced by *Bacillus polymyxis*. Polymyxins interfere with membrane function by binding to membrane phospholipids. Polymyxin is effective mainly against Gram-negative bacteria and is generally used in severe *Pseudomonas* infections or *Pseudomonas* infections that are resistant to less toxic antibiotics. It is also used in some limited instances topically. The limited use of this agent is due to the severe side effects associated with systemic administration, such as damage to the kidney and other organs.

Other cell membrane inhibitors include Amphotericin B and Nystatin produced by the bacterium *Streptomyces* which are also anti-fungal agents, used predominantly in the treatment of systemic fungal infections and *Candida* yeast infections respectively. Imidazoles, produced by the bacterium *Streptomyces*, are another class of antibiotic that is a cell membrane inhibitor. Imidazoles are used as bacterial agents as well as anti-fungal agents, e.g., used for treatment of yeast infections, dermatophytic infections, and systemic fungal infections. Imidazoles include but are not limited to clotrimazole, miconazole, ketoconazole, itraconazole, and fluconazole.

Many anti-bacterial agents are protein synthesis inhibitors. These compounds prevent bacteria from synthesizing structural proteins and enzymes and thus cause inhibition of bacterial cell growth or function or cell death. In general these compounds interfere with the processes of transcription or translation. Anti-bacterial agents that block transcription include but are not limited to Rifampins, produced by the bacterium *Streptomyces* and Ethambutol, a synthetic chemical. Rifampins, which inhibit the enzyme RNA polymerase, have a broad spectrum activity and are effective against gram-positive and gram-negative bacteria as well as *Mycobacterium tuberculosis*. Ethambutol is effective against *Mycobacterium tuberculosis*.

Anti-bacterial agents which block translation interfere with bacterial ribosomes to prevent mRNA from being translated into proteins. In general this class of compounds includes but is not limited to tetracyclines, chloramphenicol, the macrolides (e.g. erythromycin) and the aminoglycosides (e.g. streptomycin).

Some of these compounds bind irreversibly to the 30S ribosomal subunit and cause a misreading of the mRNA, e.g., the aminoglycosides. The aminoglycosides are a class of antibiotics which are produced by the bacterium *Streptomyces*, such as, for instance streptomycin, kanamycin, tobramycin, amikacin, and gentamicin. Aminoglycosides have been used against a wide variety of bacterial infections caused by Gram-positive and Gram-negative bacteria. Streptomycin has been used extensively as a primary drug in the treatment of tuberculosis. Gentamicin is used against many strains of Gram-positive and Gram-negative bacteria, including *Pseudomonas* infections, especially in combination with tobramycin. Kanamycin is used against many Gram-positive bacteria, including penicillin-resistant *Staphylococci*. One side effect of aminoglycosides that has limited their use clinically is that at dosages which are essential for efficacy, prolonged use has been shown to impair kidney function and cause damage to the auditory nerves leading to deafness.

Another type of translation inhibitor anti-bacterial agent is the tetracyclines. The tetracyclines bind reversibly to the 30s ribosomal subunit and interfere with the binding of charged tRNA to the bacterial ribosome. The tetracyclines are a class of antibiotics, produced by the bacterium *Streptomyces*, that are broad-spectrum and are effective against a variety of gram-positive and gram-negative bacteria. Examples of tetracyclines include tetracycline, minocycline, doxycycline, and chlortetracycline. They are important for the treatment of many types of bacteria but are particularly important in the treatment of Lyme disease.

Anti-bacterial agents such as the macrolides bind reversibly to the 50S ribosomal subunit and inhibits elongation of the protein by peptidyl transferase or prevents the release of uncharged tRNA from the bacterial ribosome or both. The macrolides contain large lactone rings linked through glycoside bonds with amino sugars. These compounds include erythromycin, roxithromycin, clarithromycin, oleandomycin, and azithromycin. Erythromycin is active against most Gram-positive bacteria, *Neisseria, Legionella* and *Haemophilus*, but not against the *Enterobacteriaceae*. Lincomycin and clindamycin, which block peptide bond formation during protein synthesis, are used against gram-positive bacteria.

Another type of translation inhibitor is chloramphenicol. Chloramphenicol binds the 70S ribosome inhibiting the bacterial enzyme peptidyl transferase thereby preventing the growth of the polypeptide chain during protein synthesis. Chloramphenicol can be prepared from *Streptomyces* or produced entirely by chemical synthesis. One serious side effect associated with chloramphenicol is aplastic anemia. Aplastic anemia develops at doses of chloramphenicol which are effective for treating bacteria in a small proportion (1/50,000) of patients. Chloramphenicol which was once a highly prescribed antibiotic is now seldom uses as a result of the deaths from anemia. Because of its effectiveness it is still used in life-threatening situations (e.g. typhoid fever). By combining chloramphenicol with aziridino compounds as described herein, chloramphenicol can again be used as an anti-bacterial agent because the action of the aziridino compounds allows a lower dose of the chloramphenicol to be used, a dose that does not produce side effects.

Some anti-bacterial agents disrupt nucleic acid synthesis or function, e.g., bind to DNA or RNA so that their messages cannot be read. These include but are not limited to quinolones and co-trimoxazole, both synthetic chemicals and rifamycins, a natural or semi-synthetic chemical. The quinolones block bacterial DNA replication by inhibiting the DNA gyrase, the enzyme needed by bacteria to produce their circular DNA. They are broad spectrum and examples include norfloxacin, ciprofloxacin, enoxacin, nalidixic acid and temafloxacin. Nalidixic acid is a bactericidal agent that binds to the DNA gyrase enzyme (topoisomerase) which is essential for DNA replication and allows supercoils to be relaxed and reformed, inhibiting DNA gyrase activity. The main use of nalidixic acid is in treatment of lower urinary tract infections (UTI) because it is effective against several types of Gram-negative bacteria such as *E. coli, Enterobacter aerogenes, K. pneumoniae* and *Proteus* species which are common causes of UTI. Co-trimoxazole is a combination of sulfamethoxazole and trimethoprim, which blocks the bacterial synthesis of folic acid needed to make DNA nucleotides. Rifampicin is a derivative of rifamycin that is active against Gram-positive bacteria (including *Mycobacterium tuberculosis* and meningitis caused by *Neisseria meningitidis*) and some Gram-negative bacteria. Rifampicin binds to the beta subunit of the polymerase and blocks the addition of the first nucleotide which is necessary to activate the polymerase, thereby blocking mRNA synthesis.

Another class of anti-bacterial agents is compounds that function as competitive inhibitors of bacterial enzymes. The competitive inhibitors are mostly all structurally similar to a bacterial growth factor and compete for binding but do not perform the metabolic function in the cell. These compounds include sulfonamides and chemically modified forms of sulfanilamide which have even higher and broader antibacterial activity. The sulfonamides (e.g. gantrisin and trimethoprim) are useful for the treatment of *Streptococcus pneumoniae*, beta-hemolytic streptococci and *E. coli*, and have been used in the treatment of uncomplicated UTI caused by *E. coli*, and in the treatment of meningococcal meningitis.

Antiviral agents are compounds which prevent infection of cells by viruses or replication of the virus within the cell. There are many fewer antiviral drugs than antibacterial drugs because the process of viral replication is so closely related to DNA replication within the host cell, that non-specific antiviral agents would often be toxic to the host. There are several stages within the process of viral infection which can be blocked or inhibited by antiviral agents. These stages include, attachment of the virus to the host cell (immunoglobulin or binding peptides), uncoating of the virus (e.g. amantadine), synthesis or translation of viral mRNA (e.g. interferon), replication of viral RNA or DNA (e.g. nucleoside analogues), maturation of new virus proteins (e.g. protease inhibitors), and budding and release of the virus.

Nucleotide analogues are synthetic compounds which are similar to nucleotides, but which have an incomplete or abnormal deoxyribose or ribose group. Once the nucleotide analogues are in the cell, they are phosphorylated, producing the triphosphate formed which competes with normal nucleotides for incorporation into the viral DNA or RNA. Once the triphosphate form of the nucleotide analogue is incorporated into the growing nucleic acid chain, it causes irreversible association with the viral polymerase and thus chain termination. Nucleotide analogues include, but are not limited to, acyclovir (used for the treatment of herpes simplex virus and varicella-zoster virus), gancyclovir (useful for the treatment of cytomegalovirus), idoxuridine, ribavirin (useful for the treatment of respiratory syncitial virus), dideoxyinosine, dideoxycytidine, and zidovudine (azidothymidine).

The interferons are cytokines which are secreted by virus-infected cells as well as immune cells. The interferons function by binding to specific receptors on cells adjacent to the infected cells, causing the change in the cell which protects it from infection by the virus. $\alpha$ and $\beta$-interferon also induce the expression of Class I and Class II MHC molecules on the surface of infected cells, resulting in increased antigen presentation for host immune cell recognition. α and β-interferons are available as recombinant forms and have been used for the treatment of chronic hepatitis B and C infection. At the dosages which are effective for anti-viral therapy, interferons have severe side effects such as fever, malaise and weight loss.

Immunoglobulin therapy is used for the prevention of viral infection. Immunoglobulin therapy for viral infections is different than bacterial infections, because rather than being antigen-specific, the immunoglobulin therapy functions by binding to extracellular virions and preventing them from attaching to and entering cells which are susceptible to the viral infection. The therapy is useful for the prevention of viral infection for the period of time that the antibodies are present in the host. In general there are two types of immunoglobulin therapies, normal immunoglobulin therapy and hyper-immunoglobulin therapy. Normal immune globulin therapy utilizes a antibody product which is prepared from the serum of normal blood donors and pooled. This pooled product contains low titers of antibody to a wide range of human viruses, such as hepatitis A, parvovirus, enterovirus (especially in neonates). Hyper-immune globulin therapy utilizes antibodies which are prepared from the serum of individuals who have high titers of an antibody to a particular virus. Those antibodies are then used against a specific virus. Examples of hyper-immune globulins include zoster immune globulin (useful for the prevention of varicella in immuno-compromised children and neonates), human rabies immunoglobulin (useful in the post-exposure prophylaxis of a subject bitten by a rabid animal), hepatitis B immune globulin (useful in the prevention of hepatitis B virus, especially in a subject exposed to the virus), and RSV immune globulin (useful in the treatment of respiratory syncitial virus infections).

Another type of immunoglobulin therapy is active immunization. This involves the administration of antibodies or antibody fragments to viral surface proteins. Two types of vaccines which are available for active immunization of hepatitis B include serum-derived hepatitis B antibodies and recombinant hepatitis B antibodies. Both are prepared from HBsAg. The antibodies are administered in three doses to subjects at high risk of infection with hepatitis B virus, such as health care workers, sexual partners of chronic carriers, and infants.

Thus antiviral agents that can be combined with aziridino compounds in the therapeutic compositions of the invention include nucleoside analogs, normucleoside reverse transcriptase inhibitors, protease inhibitors, and integrase inhibitors. Specific examples of antiviral compounds include the following: Acemannan; Acyclovir; Acyclovir Sodium; Adefovir; Alovudine; Alvircept Sudotox; Amantadine Hydrochloride; Aranotin; Arildone; Atevirdine Mesylate; Avridine; Cidofovir; Cipamfylline; Cytarabine Hydrochloride; Delavirdine Mesylate; Desciclovir; Didanosine; Disoxaril; Edoxudine; Enviradene; Enviroxime; Famciclovir; Famotine Hydrochloride; Fiacitabine; Fialuridine; Fosarilate; Foscarnet Sodium; Fosfonet Sodium; Ganciclovir; Ganciclovir Sodium; Idoxuridine; Indinavir; Kethoxal; Lamivudine; Lobucavir; Memotine Hydrochloride; Methisazone; Nelfinavir; Nevirapine; Penciclovir; Pirodavir; Ribavirin; Rimantadine Hydrochloride; Ritonavir; Saquinavir Mesylate; Somantadine Hydrochloride; Sorivudine; Statolon; Stavudine; Tilorone Hydrochloride; Trifluridine; Valacyclovir Hydrochloride; Vidarabine; Vidarabine Phosphate; Vidarabine Sodium Phosphate; Viroxime; Zalcitabine; Zidovudine; Zinviroxime and integrase inhibitors.

Parasiticides are agents that kill parasites directly. Such compounds are known in the art and are generally commercially available. Examples of parasiticides useful for human administration include but are not limited to albendazole, amphotericin B, benznidazole, bithionol, chloroquine HCl, chloroquine phosphate, clindamycin, dehydroemetine, diethylcarbamazine, diloxamide furoate, eflornithine, furazolidaone, glucocorticoids, halofantrine, iodoquinol, ivermectin, mebendazole, mefloquine, meglumine antimoniate, melarsoprol, metrifonate, metronidazole, niclosamide, nifurtimox, oxamniquine, paromomycin, pentamidine isethionate, piperazine, praziquantel, primaquine phosphate, proguanil, pyrantel pamoate, pyrimethanmine-sulfonamides, pyrimethanmine-sulfadoxine, quinacrine HCl, quinine sulfate, quinidine gluconate, spiramycin, stibogluconate sodium (sodium antimony gluconate), suramin, tetracycline, doxycycline, thiabendazole, tinidazole, trimethroprim-sulfamethoxazole, and tryparsamide some of which are used alone or in combination with others.

Parasiticides used in non-human subjects include piperazine, diethylcarbamazine, thiabendazole, fenbendazole, albendazole, oxfendazole, oxibendazole, febantel, levamisole, pyrantel tartrate, pyrantel pamoate, dichlorvos, ivermectin, doramectin, milbemycin oxime, iprinomectin, moxidectin, N-butyl chloride, toluene, hygromycin B thiacetarsemide sodium, melarsomine, praziquantel, epsiprantel, benzimidazoles such as fenbendazole, albendazole, oxfendazole, clorsulon, albendazole, amprolium; decoquinate, lasalocid, monensin sulfadimethoxine; sulfamethazine, sulfaquinoxaline, metronidazole.

Parasiticides used in horses include mebendazole, oxfendazole, febantel, pyrantel, dichlorvos, trichlorfon, ivermectin, piperazine; for *S. westeri*: ivermectin, benzimiddazoles such as thiabendazole, cambendazole, oxibendazole and fenbendazole. Useful parasiticides in dogs include milbemycin oxine, ivermectin, pyrantel pamoate and the combination of ivermectin and pyrantel. The treatment of parasites in swine can include the use of levamisole, piperazine, pyrantel, thiabendazole, dichlorvos and fenbendazole. In sheep and goats anthelmintic agents include levamisole or ivermectin. Caparsolate has shown some efficacy in the treatment of *D. immitis* (heartworm) in cats.

Agents used in the prevention and treatment of protozoal diseases in poultry, particularly trichomoniasis, can be administered in the feed or in the drinking water and include protozoacides such as aminonitrothiazole, dimetridazole (Emtryl), nithiazide (Hepzide) and Enheptin.

Anti-fungal agents are useful for the treatment and prevention of infective fungi. Anti-fungal agents are sometimes classified by their mechanism of action. Some anti-fungal agents function as cell wall inhibitors by inhibiting glucose synthase. These include, but are not limited to, basiungin/ECB. Other anti-fungal agents function by destabilizing membrane integrity. These include, but are not limited to, imidazoles, such as clotrimazole, sertaconzole, fluconazole, itraconazole, ketoconazole, miconazole, and voriconacole, as well as FK 463, amphotericin B, BAY 38-9502, MK 991, pradimicin, UK 292, butenafine, and terbinafine. Other anti-fungal agents function by breaking down chitin (e.g. chitinase) or immunosuppression (501 cream).

Some exemplary anti-fungal agents include imidazoles, FK 463, amphotericin B, BAY 38-9502, MK 991, pradimicin, UK 292, butenafine, chitinase and 501 cream, Acrisorcin; Ambruticin; Amorolfine, Amphotericin B; Azaconazole; Azaserine; Basifungin; Bifonazole; Biphenamine Hydrochloride; Bispyrithione Magsulfex; Butoconazole Nitrate; Calcium Undecylenate; Candicidin; Carbol-Fuchsin; Chlordantoin; Ciclopirox; Ciclopirox Olamine; Cilofungin; Cisconazole; Clotrimazole; Cuprimyxin; Denofungin; Dipyrithione; Doconazole; Econazole; Econazole Nitrate; Enilconazole; Ethonam Nitrate; Fenticonazole Nitrate; Filipin; Fluconazole; Flucytosine; Fungimycin; Griseofulvin; Hamycin; Isoconazole; Itraconazole; Kalafungin; Ketoconazole; Lomofungin; Lydimycin; Mepartricin; Miconazole; Miconazole Nitrate; Monensin; Monensin Sodium; Naftifine Hydrochloride; Neomycin Undecylenate; Nifuratel; Nifurmerone; Nitralamine Hydrochloride; Nystatin; Octanoic Acid; Orconazole Nitrate; Oxiconazole Nitrate; Oxifungin Hydrochloride; Parconazole Hydrochloride; Partricin; Potassium Iodide; Proclonol; Pyrithione Zinc; PyrroInitrin; Rutamycin; Sanguinarium Chloride; Saperconazole; Scopafungin; Selenium Sulfide; Sinefungin; Sulconazole Nitrate; Terbinafine; Terconazole; Thiram; Ticlatone; Tioconazole; Tolciclate; Tolindate; Tolnaftate; Triacetin; Triafungin; Undecylenic Acid; Viridofulvin; Zinc Undecylenate; and Zinoconazole Hydrochloride.

The invention also provides combinations of two or more compounds that inhibit cellular necrosis. The invention also provides combinations of one or more compounds that inhibit cellular necrosis combined with one or more additional agents or compounds (e.g., other therapeutic compounds for treating a disease, condition, or infection).

The invention also provides kits including one or more compounds or combinations of the invention (e.g., the heterocylic thiohydantoin, hydantoin, oxazolidinone, thioxo-oxazolidinone, pyrimidinone, oxazinanone compounds, or combinations thereof). A kit can also include one or more additional agents or compounds described herein. The different components of the kit can be provided in different containers. The kit can be compartmentalized to receive the containers in close confinement. The kit can also contain instructions for using the compounds according to the invention.

As used herein, a kit such as a compartmentalized kit includes any kit in which compounds or agents are contained in separate containers. Illustrative examples of such containers include, but are not limited to, small glass containers, plastic containers or strips of plastic or paper. Particularly preferred types of containers allow the skilled worker to efficiently transfer reagents from one compartment to another compartment such that the samples and reagents are not cross-contaminated and the agents or solutions of each container can be added in a quantitative fashion from one compartment to another. Such containers include, but are not limited to, a container that will accept a compound or combination of compounds and/or other agents of the invention. One or more compounds or agents can be provided as a powder (e.g. lyophilized powder) or precipitate. Such compound(s) can be resuspended prior to administration in a solution that may be provided as part of the kit or separately available. A kit can contain compounds or agents in other forms such as liquids, gels, solids, as described herein. Different compounds and/or agents may be provided in different forms in a single kit.

The term "$ED_{50}$" means the dose of a drug that produces 50% of its maximum response or effect. Alternatively, "$ED_{50}$" means the dose that produces a pre-determined response in 50% of test subjects or preparations.

The term "$LD_{50}$" means the dose of a drug that is lethal in 50% of test subjects.

The term "$EC_{50}$" means the concentration of a drug that produces 50% of its maximum response or effect in a test assay. Alternatively, "$EC_{50}$" means the effective concentration that produces a pre-determined response in 50% of test assays.

The term "therapeutic index" refers to the therapeutic index of a drug defined as $LD_{50}/ED_{50}$.

The term "structure-activity relationship (SAR)" refers to the way in which altering the molecular structure of drugs alters their interaction with a receptor, enzyme, etc.

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

EXAMPLES

Example 1

Screening Assays Used to Identify Inhibitors of Cellular Necrosis

After a cell receives an initial assault either apoptotic, necrotic, or both apoptotic and necrotic mechanisms of cell death may be activated. The present example focuses on the necrosis pathway. Several chemical assaults were used to induce cell death, including exposure to tumor necrosis factor alpha (TNF-α), Fas ligand or β-amyloid protein. Various cell types were also used, including human neuroblastoma cells (SH-SY5Y) and human Jurkat T cells. In order to block the apoptosis mechanism, a general caspase inhibitor, N-benzyloxycarbonyl-valine-alanine-aspartic acid-(OMe) fluoromethyl ketone (zVAD, Polyerino, A. J.; Patterson, S. D. *J. Biol. Chem.* 1997, 272, 7013-7021), was used. This compound inhibits all caspases and consequently disrupts the apoptosis pathway. Resulting cell death occurs by a necrosis-like mechanism (Holler, N., et al. *Nature Immunol.* 2000, 1, 489-495; Kawahara, A., et al. *J. Cell Biol.* 1998, 143, 1353-1360). Experimental compounds were applied to the cells in attempts to rescue them from this necrotic death. Therefore, compounds found to restore cell viability using this protocol are inhibitors of the necrosis pathway.

Compound libraries were screened for inhibition of cell death induced by TNF-α in the presence of zVAD in human B cell line U-937. One compound identified as an inhibitor of necrosis was 1:

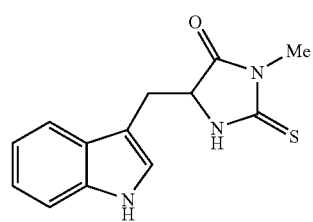

Compounds were also tested in another necrosis assay utilizing human Jurkat T cells, Fas ligand to induce cell death, and zVAD to inhibit the apoptosis pathway. After 36 h, cell viability was measure by the commercial CellTiter ATP cell viability assay (Promega).

Figure 2:
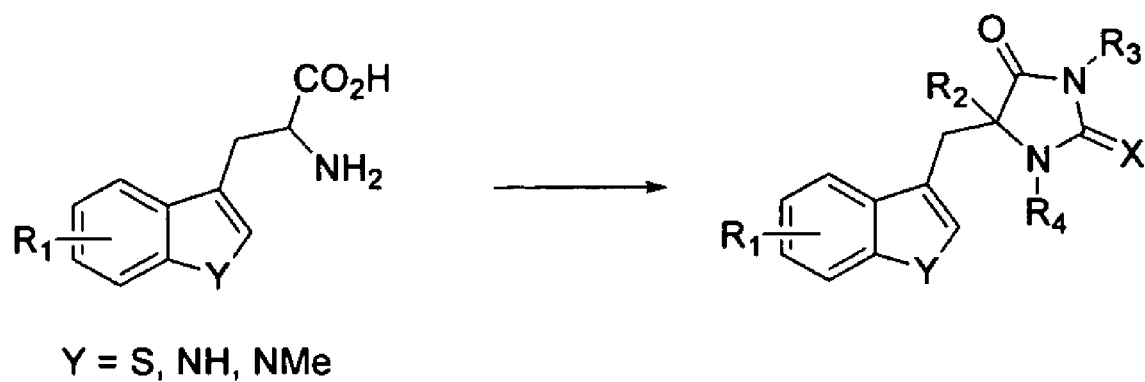
FIG. 2 depicts a general scheme for synthesizing a heterocyclic compound comprising a thiohydantoin or hydantoin moiety.
Figure 3:
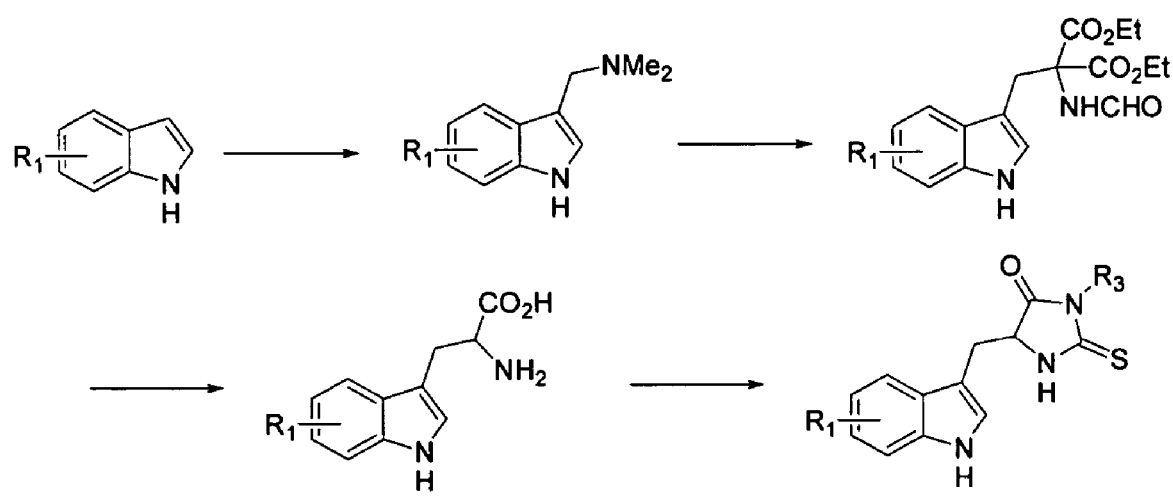
FIG. 3 depicts a general scheme for synthesizing a heterocyclic compound comprising a thiohydantoin moiety.
Figure 4:
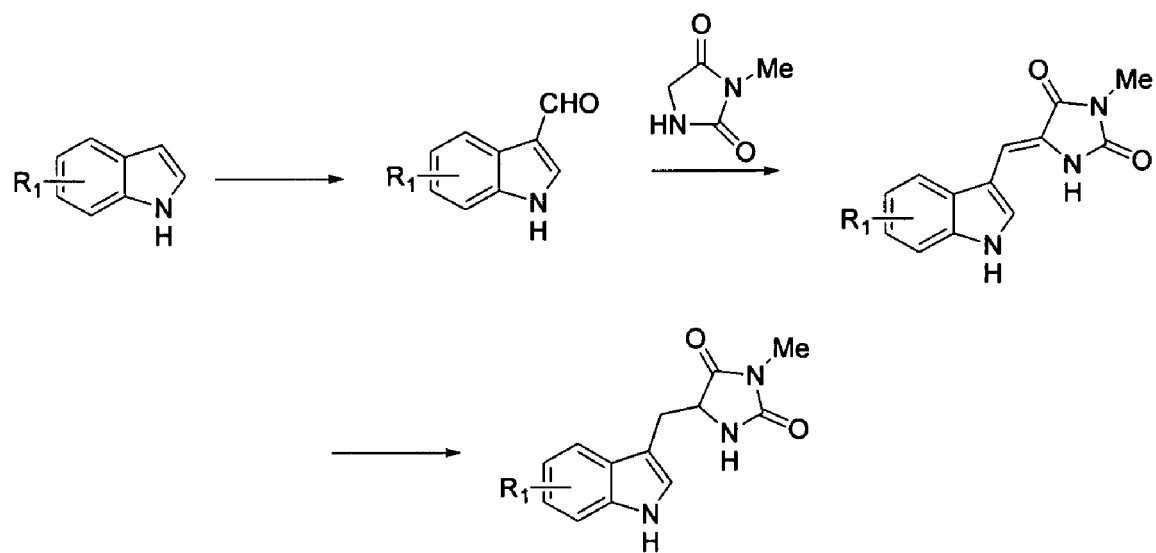
FIG. 4 depicts a general scheme for synthesizing a heterocyclic compound comprising a hydantoin moiety.
Figure 5:
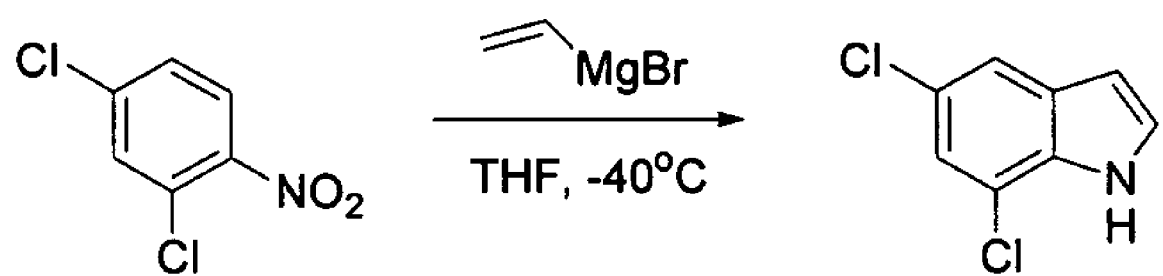
FIG. 5 depicts a scheme for the preparation of indoles.

A structure-activity-relationships (SAR) study was conducted in order to increase anti-necrosis activity. The compounds in Table 1 were prepared according to the procedures outlined in FIGS. 2 and 3.

TABLE 1

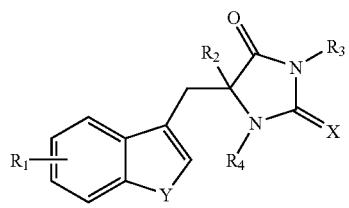

| Compound No. | $R_1$ | $R_2$ | $R_3$ | $R_4$ | X | Y |
|---|---|---|---|---|---|---|
| 893-01 | H | H | Me | H | S | NH |
| 893-02 | H | Me | Me | H | S | NH |
| 893-03 | H | H | Me | Me | S | NH |
| 893-04 | H | H | Et | H | O | NH |
| 893-05 | 6-F | H | Me | H | S | NH |
| 893-06 | 5-OMe | H | Me | H | S | NH |
| 893-07 | 5-OH | H | Me | H | S | NH |
| 893-08 | H | H | Me | H | S | NMe |
| 893-09 | 7-F | H | Me | H | S | NH |
| 893-10 | 7-Cl | H | Me | H | S | NH |
| 893-11 | 6-Cl | H | Me | H | S | NH |
| 893-12 | 7-Br | H | Me | H | S | NH |
| 893-13 | 7-OMe | H | Me | H | S | NH |
| 893-14 | 5-Cl | H | Me | H | S | S |
| 893-15 | 7-Cl | H | Me | H | S | NMe |
| 893-16 | 6-SO$_2$Me; 7-Cl | H | Me | H | S | NH |
| 893-17 | H | H | CH$_2$CH$_2$-morpholine | H | S | NH |
| 893-18 | H | H | H | H | S | NH |
| 893-19 | H | H | H | H | O | NH |
| 893-20 | H | H | Me | H | O | NH |
| 893-21 | H | H | Me | H | S | S |
| 893-22 | H | H | Me | H | O | NH |
| 893-23 | 7-Me | H | Me | H | O | NH |
| 893-24 | 5-Cl | H | Me | H | O | NH |
| 893-25 | 7-OMe | H | Me | H | O | NH |
| 893-26 | 5-OMe | H | Me | H | O | NH |
| 893-27 | 6-Cl | H | Me | H | O | NH |
| 893-28 | 7-F | H | Me | H | O | NH |

Me = methyl, Et = ethyl

Other derivatives were also prepared utilizing similar procedures:

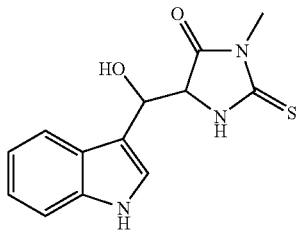

893-29

893-30

Compounds were screened for anti-necrotic activity utilizing human Jurkat T cells challenged with Fas ligand and treated with zVAD to inhibit the apoptosis pathway. Table 2 shows the EC$_{50}$ (μM) values of select compounds for cell viability.

TABLE 2

| Compound Number | EC$_{50}$ (μM) |
|---|---|
| 893-01 | 6.0 |
| 893-04 | 10.0 |
| 893-05 | 2.3 |
| 893-08 | 35 |
| 893-09 | 4.0 |
| 893-10 | 1.5 |
| 893-11 | 67.0 |
| 893-12 | 1.8 |
| 893-13 | 10.3 |
| 893-21 | 8.0 |
| 893-20 | 6.0 |

Compounds were screened for anti-necrotic activity utilizing human FAD-deficient Jurkat T cells challenged with human TNF-alpha. FADD−/− Jurkat cells (Juo P, et al. Cell Growth Differ. 1999, 10(12):797-804) were seeded at the density of 5*10$^5$ cells/mL into 96 well white plates (Costar) at 100 μL/well. Cells were treated in duplicate with various concentrations of test compounds in the presence or absence of 10 ng/ml human TNFα (Cell Sciences). After 30 hours viability of the cells was determined using luminescent ATP-based cell viability assay (CellTiter-Glo, Promega). Percentage of protection by the compound was calculated as a ratio of the cps (counts per second) value in the well treated with the test compound and TNFα to the cps value in the well treated with the compound alone. Table 3 shows the EC$_{50}$ (μM) values of select compounds for cell viability.

TABLE 3

| Compound Number | EC$_{50}$ (μM) |
|---|---|
| 893-22 | 0.439 |
| 893-23 | 0.095 |
| 893-24 | 6.8 |
| 893-25 | 0.229 |
| 893-26 | >300 |
| 893-27 | 1.12 |
| 893-28 | 0.324 |
| 893-31 | 0.303 |
| 893-32 | 0.078 |
| 893-33 | >10 |
| 893-34 | 0.154 |
| 893-35 | 0.448 |
| 893-36 | >10 |
| 893-37 | 1.8 |
| 893-38 | >10 |
| 893-39 | 5.4 |
| 893-40 | >10 |

TABLE 3-continued

| Compound Number | EC$_{50}$ (μM) |
|---|---|
| 893-41 | >10 |
| 893-42 | >10 |
| 893-43 | >10 |
| 893-44 | >10 |
| 893-45 | >10 |
| 893-46 | 5.3 |
| 893-47 | >10 |
| 893-48 | >10 |
| 893-49 | 4.3 |
| 893-50 | >10 |
| 893-51 | >10 |
| 893-52 | >10 |
| 893-53 | 0.359 |
| 893-21 | 0.845 |
| 893-54 | 0.200 |

Inhibition of LPS-induced necrosis. RAW264.7 cells were maintained in RPMI1640 with antibiotic-antimycotic mixture and 10% FBS. One day prior to the experiment cells were seeded into 96 well plates at the density of 5000 cells/well. Cells were treated with the indicated dose of LPS and 100 μM zVAD-fmk (marked "Z", Q-Biogene), 0.25 μg/ml cyclohexamide ("C", it potentiates aponecrosis induced by TNFalpha, Sigma) and 30 uM of compound 893-01. Cell viability was determined 24 hr later using CellTiter-Glo ATP assay (Promega). Viability is expressed a percentage of the viable RAW264.7 macrophages in the treated well versus the untreated control, which is set as 100% viability as shown in FIG. 1 (cells treated with LPS and the apoptotic inhibitor zVAD (marked "Z" in FIG. 1) and/or cyclohexamide, a potentiator of aponecrosis (marked "C" in FIG. 1).

Accordingly, compounds of the invention are inhibitors of cellular necrosis. The compounds are effective at maintaining cell viability when the cells were challenged with toxins (e.g. TNF-alpha, LPS) and the apoptosis pathway had been interrupted by the addition of zVAD. This protection was found in different cell types, such as human neuronal cells, human T-cells and macrophages. Compounds described herein may be useful as therapeutic agents (alone or in combination with other compounds) for the treatment of humans afflicted with an acute or chronic disease. In addition, these compounds can be used in assay development of novel molecular targets integral to induced necrotic cell death.

Example 2

Preparation of 2-chloro-4-methanesulfonyl-6-trimethylsilanylethynyl-phenylamine

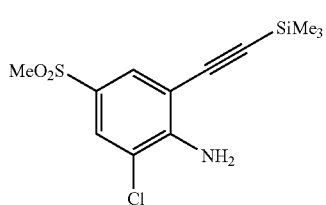

To a solution of 2-chloro-4-methanesulfonylaniline (822.6 mg, 4.0 mmol.) in dichloromethane (10 mL) were added, under argon, bis(pyridine)iodinium tetrafluoroborate (2.970 gm, 8 mmol.) and trifluoromethanesulfonic acid (2.40 g, 16 mmol.). The reaction mixture stirred at room temperature for ~16 h. It was diluted with water, and extracted in dichloromethane, dried and concentrated. The residue was purified on the column using 0 to 40% ethyl acetate-hexane to give 2-chloro-6-iodo-4-methanesulfonylaniline (969 mg, 73%): $^1$H NMR (500 MHz, CDCl$_3$): 3.03 (s, 3H), 5.12 (s, 2H), 7.81 (s, 1H), 8.09 (s, 1H).

To the suspension of 2-chloro-6-iodo-4-methanesulfonylaniline (886.9 mg, 2.7 mmol.), Pd(PPh$_3$)$_2$Cl$_2$ (94.5 mg, 0.13 mmol), and CuI (24.3 mg, 0.13 mmol.) was added triethyl amine (2 mL), and the suspension was slowly treated with (trimethylsilyl)acetylene (0.22 mL, 0.16 mmol.) at 0° C. The reaction mixture was stirred at room temperature for ~16 h. Solvent was removed under vacuum. The residue was diluted with ethyl acetate, and filtered through Celite. The filtrate was washed with saturated NaCl, water, dried over anhydrous sodium sulfate and concentrated. The residue was purified by column chromatography on silica gel using 20% ethyl acetate-hexane to give 2-chloro-4-methanesulfonyl-6-trimethylsilanylethynyl-phenylamine (632 mg, 78%). The $^1$H NMR (500 MHz, CDCl$_3$) spectrum was: 0.27 (s, 9H), 3.01 (s, 3H), 5.17 (s, 2H), 7.77 (d, J=2.5 Hz, 1H), 7.78 (d, J=2.5 Hz, 1H).

Example 3

Preparation of 7-Chloro-4-methanesulfonyl-1H-indole

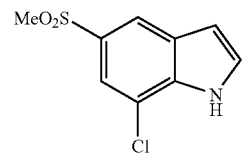

To a mixture of 2-chloro-4-methanesulfonyl-6-trimethylsilanylethynyl-phenylamine (100 mg, 0.33 mmol.) and CuI (126.2 mg, 0.66 mmol.), DMF (2 mL) under argon was added and the reaction mixture was heated at 100° C. for 2 hr. The reaction mixture was diluted with ethyl acetate and filtered through Celite. The filtrate was washed with saturated NaCl, dried and concentrated. The residue was purified by column chromatography on silica gel using 30% ethyl acetate-hexane to give 7-Chloro-4-methanesulfonyl-1H-indole (38 mg, 50%): mp 160-162° C., $^1$H NMR (500 MHz, CDCl$_3$): 3.09 (s, 3H), 6.75 (m, 1H), 7.43 (m, 1H), 7.75 (d, J=2.5 Hz, 1H), 8.19 (d, J=2.5 Hz, 1H), 8.84 (s, 1H).

Example 4

General procedure for the preparation of 1H-indol-3-ylmethyl-dimethylamine, exemplified for (7-Fluoro-1H-indol-3-ylmethyl)dimethyl-amine

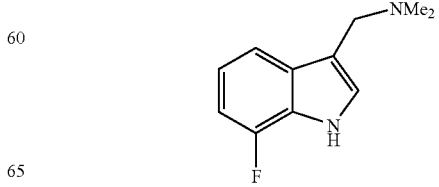

To a mixture of acetic acid (13.6 mL) and formaldehyde (0.340 mL, 4.5 mmol, 37% solution) under argon was added dimethyl amine (2.05 mL, 16.3 mmol., 40% solution). The reaction mixture was stirred for 10 min and then treated with 7-fluoroindole (540 mg, 4.0 mmol.). The resulting mixture was stirred at room temperature for ~16 h. The reaction mixture was first neutralized with $K_2CO_3$ and then basified with NaOH (2N), and then extracted in ethyl acetate, washed with water, dried, and concentrated. Solid obtained was recrystallized from ethyl acetate and hexane to give (7-Fluoro-1H-indol-3-ylmethyl)dimethylamine (570 mg, 74%): mp 133-137° C., $^1$H NMR (500 MHz, CDCl$_3$): 2.31 (s, 6H), 3.62 (s, 2H), 6.88-6.92 (dd, J=8.0 and 8.0 Hz, 1H), 7.00-7.04 (m, 1H), 7.16 (d, J=2.5 Hz, 1H), 7.46 (d, J=8.0 Hz, 1H), 8.34 (s, 1H).

(7-Bromo-1H-indol-3-ylmethyl)dimethylamine: yield 81%, mp 113-118° C., $^1$H NMR (500 MHz, CDCl$_3$): 2.30 (s, 6H), 3.61 (s, 2H), 7.01 (dd, J=8.0 and 8.0 Hz, 1H), 7.20 (d, J=2.0 Hz, 1H), 7.35 (d, J=7.5 Hz, 1H), 7.66 (d, J=8.0 Hz, 1H), 8.25 (s, 1H).

(7-Chloro-1H-indol-3-ylmethyl)dimethylamine: yield 86%, mp 136-138° C., $^1$H NMR (500 MHz, CDCl$_3$): 2.27 (s, 6H), 3.61 (s, 2H), 7.04 (dd, J=8.0 and 8.0 Hz, 1H), 7.15 (d, J=2.5 Hz, 1H), 7.18 (d, J=7.5 Hz, 1H), 7.60 (d, J=7.5 Hz, 1H), 8.53 (s,1H,).

(7-Methoxy-1H-indol-3-ylmethyl)dimethylamine: yield 81%, mp 99-102° C., $^1$H NMR (500 MHz, CDCl$_3$): yield 81%, 2.27 (s, 6H), 3.62 (s, 2H), 3.95 (s, 3H), 6.64 (d, J=7.5 Hz, 1H), 7.04 (dd, J=8.0 and 7.5 Hz, 1H), 7.11 (d, J=2.5 Hz, 1H), 7.30 (d, J=8.0 Hz, 1H), 8.36 (s, 1H).

(7-Chloro-5-methanesulfonyl-1H-indol-3-ylmethyl)dimethylamine: yield 82%, $^1$H NMR (500 MHz, CDCl$_3$): 2.29 (s, 3H), 3.10 (s, 3H), 3.64 (s, 2H), 7.37 (s, 1H), 7.77 (d, J=1.5 Hz, 1H), 8.30 (d, J=1.5 Hz, 1H), 8.63 (s, 1H).

Example 5

General procedure for the preparation of 2-(1H-indol-3-ylmethyl)-2-formylamino-malonic acid diethyl esters. Preparation of 2-(7-Fluoro-1H-indol-3-ylmethyl)-2-formylamino-malonic acid diethyl ester

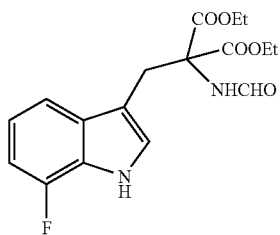

A suspension of (7-fluoro-1H-indol-3-ylmethyl)-dimethyl-amine (550 mg, 0.0028 mol.), 2-formylamino-malonic acid diethyl ester (640 mg, 0.0031 mol.), and NaOH (30 mg) in toluene (20 mL) under argon was refluxed for 3 days. The reaction mixture was concentrated and purified by column chromatography on silica gel using 40% ethyl acetate-hexane to give 2-(7-Fluoro-1H-indol-3-ylmethyl)-2-formylamino-malonic acid diethyl ester (1.0 gm, 99%): mp 164-166° C., $^1$H NMR (500 MHz, CDCl$_3$): 1.28 (t, J=7.5 Hz, 6H), 3.87 (s, 2H), 4.17-4.31 (m, 4H), 6.80 (s, 1H), 6.86-6.86 (dd, J=8.0 and 8.0 Hz, 1H), 6.97-7.01 (m, 2H), 7.27 (s, 1H), 8.18 (d, J=1.5 Hz, 1H), 8.27 (s, 1H).

2-(7-Bromo-1H-indol-3-ylmethyl)-2-formylamino-malonic acid diethyl ester: yield, 98%, mp 159-162° C., $^1$H NMR (500 MHz, CDCl$_3$): 1.28 (t, J=7.5 Hz, 6H), 3.85 (s, 2H), 4.18-4.31 (m, 4H), 6.61 (d, J=8.0 Hz, 1H), 6.78 (s, 1H), 6.90 (d, J=2.0 Hz, 1H), 6.99 (dd, J=7.5 and 8.0 Ha, 1H), 7.10 (d, J=7.5 Hz, 1H), 8.18 (d, J=1.5 Hz, 1H), 8.28 (s, 1H).

2-(7-Chloro-1H-indol-3-ylmethyl)-2-formylamino-malonic acid diethyl ester: yield 65%, mp 170-174° C., $^1$H NMR (500 MHz, CDCl$_3$): 1.28 (t, J=7.5 Hz, 6H), 3.87 (s, 2H), 4.17-4.31 (m, 4H), 6.80 (s, 1H), 7.00 (d, J=2.5 Hz, 1H), 7.02 (dd, J=7.5 and 8.0 Hz, 1H), 7.17 (d, J=7.5 Hz, 1H), 7.40 (d, J=8.0 Hz, 1H), 8.18 (d, J=1.0 Hz, 1H), 8.32 (s, 1H).

2-(7-Methoxy-1H-indol-3-ylmethyl)-2-formylamino-malonic acid diethyl ester: yield 73% (based on unrecovered starting compound), mp 149-153° C., $^1$H NMR (500 MHz, CDCl$_3$): 1.28 (t, J=7.5 Hz, 6H), 3.85 (s, 2H), 3.94 (s, 3H), 4.17-4.31 (m, 4H), 6.61 (d, J=8.0 Hz, 1H), 6.78 (s, 1H), 6.90 (d, J=2.0 Hz, 1H), 6.99 (dd, J=7.5 and 7.5 Hz, 1H), 7.10 (d, J=7.5 Hz, 1H), 8.18 (d, J=1.5 Hz, 1H), 8.28 (s, 1H).

2-(7-Chloro-5-methanesulfonyl-1H-indol-3-ylmethyl)-2-formylamino-malonic acid diethyl ester: yield 66%, mp 206-209° C., $^1$H NMR (500 MHz, CDCl$_3$): 1.15 (t, J=7.5 Hz, 6H), 3.21 (s, 3H), 3.67 (s, 2H), 4.09-4.17 (m, 4H), 7.34 (s, 1H), 7.68 (d, J=1.0 Hz, 1H), 7.91 (d, J=1.5 Hz, 1H), 8.03 (s, 1H), 8.68 (s, 1H), 12.07 (s, 1H).

Example 6

Preparation of 2-(7-Chloro-1-methyl-1H-indol-3-ylmethyl)-2-formylamino-malonic acid diethyl ester

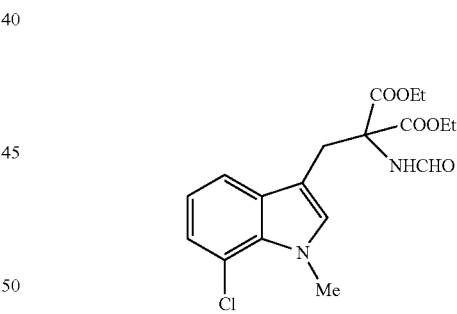

To a suspension of DMSO (5 mL) and KOH (229 mg, 4.1 mmol) was added 2-(7-Chloro-1H-indol-3-ylmethyl)-2-formylamino-malonic acid diethyl ester (500 mg, 1.4 mmol), followed by MeI (0.127 mL, 2 mmol) at 0° C. The reaction mixture was stirred for 4 hr. After the usual workup the product was purified by column chromatography on silica gel using 30% ethyl acetate—hexane to give 2-(7-Chloro-1-methyl-1H-indol-3-ylmethyl)-2-formylamino-malonic acid diethyl ester (402 mg, 77%): mp 83-87° C., $^1$H NMR (500 MHz, CDCl$_3$): 1.28 (t, J=7.5 Hz, 6H), 3.81 (s, 2H), 4.08 (s, 3H), 4.17-4.31 (m, 4H), 6.71 (s, 1H), 6.93 (dd, J=7.5 and 7.5 Hz, 1H), 7.10 (d, J=7.5 Hz, 1H), 7.35 (d, J=7.5 Hz, 1H), 8.18 (d, J=1.0 Hz, 1H).

Example 7

General procedure for the preparation of tryptophans, exemplified for DL-7-Fluoro-tryptophan

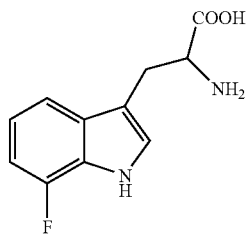

A solution of 2-(7-Fluoro-1H-indol-3-ylmethyl)-2-formylamino-malonic acid diethyl ester in THF was treated with NaOH (300 mg in 10 mL water) at room temperature for 24 hr. The mixture was slowly acidified with acetic acid (5 mL) and then refluxed for 24 hr. The reaction mixture was concentrated under vacuum, and treated with dil. HCl (10 mL, 3M) and then again refluxed for ~16 h. The reaction was allowed to cool to room temperature. The pH was adjusted to 6.0 with 2M KOH. The white solid that formed was filtered, washed with water, and dried under vacuum to give 7-fluoro-tryptophan (282 mg, 52%): mp 256-261° C., $^1$H NMR (500 MHz, DMSO-$d_6$): 2.92-2.97 (dd, J=8.5 and 15 Hz, 1H), 3.25-3.29 (dd, J=4.0 and 15 Hz, 1H), 3.38-3.41 (dd, J=4.0 and 8.5 Hz, 1H), 6.87-6.96 (m, 2H), 7.25 (s, 1H), 7.37 (d, J=7.5 Hz, 1H), 11.36 (s, 1H).

DL-7-Bromo-tryptophan: yield 92%, mp>260° C., $^1$H NMR (500 MHz, DMSO-$d_6$): 2.95-3.00 (dd, J=8.5 and 15 Hz, 1H), 3.25-3.29 (dd, J=4.0 and 15 Hz, 1H), 3.40-3.42 (dd, J=4.0 and 8.5 Hz, 1H), 6.91 (dd, J=8.0 and 7.5 Hz, 1H), 7.27 (d, J=2.0 Hz, 1H), 7.29 (d, J=7.5 Hz, 1H), 7.60 (d, J=8.0 Hz, 1H), 11.11 (s, 1H).

DL-7-Chloro-tryptophan: yield 83%, mp 236-239° C., $^1$H NMR (500 MHz, DMSO-$d_6$): 2.95-3.00 (dd, J=8.5 and 15 Hz, 1H), 3.24-3.28 (dd, J=4.0 and 15 Hz, 1H), 3.41-3.43 (dd, J=4.0 and 8.5 Hz, 1H), 6.95 (dd, J=7.5 and 7.5 Hz, 1H), 7.10 (d, J=7.5 Hz, 1H), 7.22 (s, 1H), 7.52 (d, J=7.5 Hz, 1H), 11.18 (s, 1H).

DL-7-Chloro-N-methyl-tryptophan: yield 71%, mp 208-211° C., $^1$H NMR (500 MHz, DMSO-$d_6$): 2.95-3.43 (m, 3H) 4.02 (s, 3H), 6.92-6.96 (m, 1H), 7.09 (d, J=7.5 Hz, 1H), 7.16 (s, 1H), 7.50-7.73 (dd, J=7.5 and 7.5 Hz, 1H).

DL-7-Methoxy-tryptophan: yield 46%, used as such for the next reaction without isolation.

DL-7-Chloro-5-methanesulfonyl-tryptophan: yield 83%, mp 292-294° C., $^1$H NMR (500 MHz, DMSO-$d_6$): 3.04-3.08 (dd, J=8.5 and 15.5 Hz, 1H), 3.32 (m, 1H), 3.44-3.47 (dd, J=4.5 and 8.5 Hz, 1H), 7.47 (s, 1H), 7.66 (d, J=1.5 Hz, 1H), 8.20 (d, J=1.5 Hz, 1H), 11.90 (s, 1H).

Example 8

General procedure for the preparation of 5-(1H-Indol-3-ylmethyl)-3-methyl-2-thioxo-imidazolidin-4-ones from tryptophan esters, exemplified for 893-01

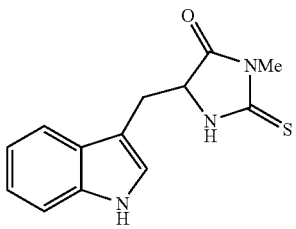

To a solution of L-tryptophan methyl ester hydrochloride (0.254 mg, 0.001 mol.) in dichloromethane (10 mL) was added triethyl amine (0.1 mL) followed by methylisothiocyanate (0.074 gm, 0.001 mol.). The reaction mixture was stirred at room temperature for 1 hr and then concentrated. The residue obtained was purified by column chromatography on silica gel using 30% ethyl acetate in hexane to give 893-01 (230 mg, 89%): mp 144-148° C., $^1$H NMR (500 MHz, CDCl$_3$): 2.97-3.02 (dd, J=10.5 and 14.5 Hz, 1H), 3.22 (s, 3H), 3.49-3.53 (dd, J=3.5 and 14.5 Hz, 1H), 4.36-4.39 (m, 1H), 6.98 (s, 1H), 7.11 (d, J=2.5 Hz, 1H), 7.17 (t, J=8.0 Hz, 1H), 7.24 (d, J=7.5 Hz, 1H), 7.40 (d, J=8.0 Hz, 1H), 7.60 (d, J=7.5 Hz, 1H), 8.16 (s, 1H).

Example 9

General procedure for the preparation of 5-(1H-Indol-3-ylmethyl)-3-methyl-2-thioxo-imidazolidin-4-ones from tryptophans, exemplified for 893-01

To a solution of L-tryptophan (0.408 gm, 0.002 mol.) in 50% aqueous pyridine (10 mL) was added methylisothiocyanate (0.175 gm, 0.0024 mol.) followed by the addition of NaOH (0.5 N) to pH (8-9). The reaction mixture was stirred at room temperature for 1 h and then extracted with petroleum ether. Aqueous layer was acidified with concentrated HCl. The acidic solution (pH 1.0) was left at room temperature for 2 days. Then it was extracted in ethyl acetate, dried, and concentrated. The residue obtained was purified by column chromatography on silica gel using 30% ethyl acetate-hexane as an eluent to give 893-01 (42 mg, 8%): mp 144-148° C.

5-(1H-Indol-3-ylmethyl)-1,3-dimethyl-2-thioxo-imidazolidin-4-one (893-03):

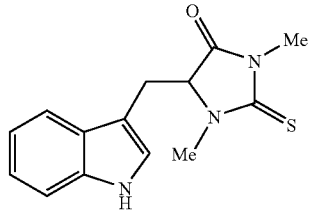

Yield 15%, mp 132-135° C., $^1$H NMR (400 MHz, CDCl$_3$): 3.04 (s, 3H), 3.22 (s, 3H), 3.37-3.39 (m, 2H), 4.23-4.25 (m, 1H), 6.92 (d, J=1.6 Hz, 1H), 7.08-7.18 (m, 2H), 7.31 (d, J=8.4 Hz, 1H), 7.55 (d, J=8.4 Hz, 1H), 8.04 (s, 1H).

3-Methyl-5-(1-methyl-1H-Indol-3-ylmethyl)-2-thioxo-imidazolidin-4-one (893-08):

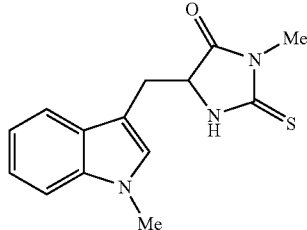

Yield 15%, mp 155-157° C., $^1$H NMR (400 MHz, CDCl$_3$): 2.88-2.94 (dd, J=10.0 and 14.8 Hz, 1H), 3.45-3.50 (dd, J=4.0 and 14.8 Hz, 1H), 4.30-4.34 (m, 1H), 6.81 (s, 1H), 6.92 (s, 1H), 7.10-7.31 (m, 3H), 7.54 (d, J=8.0 Hz, 1H).

5-(1H-Indol-3-ylmethyl)-3,5-dimethyl-2-thioxo-imidazolidin-4-one (893-02):

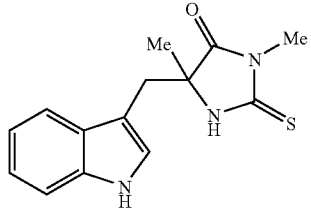

Yield 57%, mp 179-182° C., $^1$H NMR (400 MHz, CDCl$_3$): 1.42 (s, 3H), 3.10 (s, 3H), 3.12-3.13 (m, 2H), 7.03 (s, 1H), 7.11-7.20 (m, 3H), 7.33 (d, J=7.2 Hz), 7.54 (d, J=8.0 Hz, 1H), 8.13 (s, 1H).

5-(6-Fluoro-1H-Indol-3-ylmethyl)-3-methyl-2-thioxo-imidazolidin-4-one (893-05):

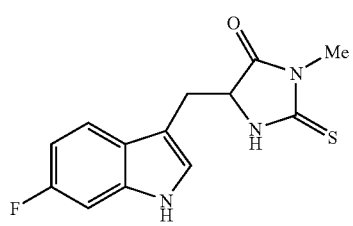

Yield 24%, mp 126-129° C., $^1$H NMR (400 MHz, CDCl$_3$): 2.94-3.00 (dd, J=10.0 and 14.8 Hz, 1H), 3.16 (s, 3H), 3.40-3.45 (dd, J=4.0 and 14.8 Hz, 1H), 4.30 -4.34 (m, 1H), 6.87-6.92 (m, 2H), 7.02-7.05 (m, 2H), 7.44-7.47 (m, 1H), 8.09 (s, 1H).

5-(5-Methoxy-1H-Indol-3-ylmethyl)-3-methyl-2-thioxo-imidazolidin-4-one (893-06):

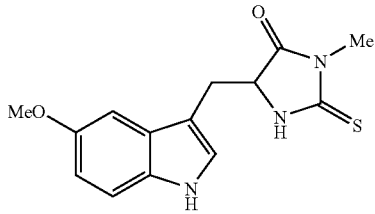

Yield 17%, mp 181-185° C., $^1$H NMR (400 MHz, CDCl$_3$): 2.90-2.96 (dd, J=10.0 and 14.8 Hz, 1H), 3.19 (s, 3H), 3.41-3.46 (dd, J=4.0 and 14.8 Hz, 1H), 3.83 (s, 3H), 4.30-4.34 (m, 1H), 6.85-6.87 (dd, J=2.4 and 8.4 Hz, 1H), 6.91 (s, 3H), 6.96 (d, J=2.4 Hz, 1H), 7.04 (d, J=2.4 Hz, 1H), 7.25 (d, J=8.4 Hz, 1H), 8.00 (s, 1H).

5-(5-Hydroxy-1H-Indol-3-ylmethyl)-3-methyl-2-thioxo-imidazolidin-4-one (893-07):

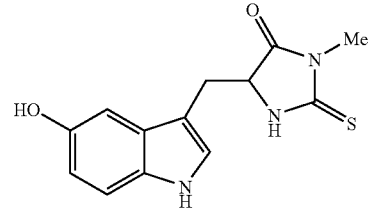

Yield 17%, mp 166-168° C., $^1$H NMR (400 MHz, CDCl$_3$): 2.87-2.93 (dd, J=10.0 and 14.8 Hz, 1H), 3.18 (s, 3H), 3.37-3.41 (dd, J=4.0 and 14.8 Hz, 1H), 4.27-4.31 (m, 1H), 6.76-6.79 (dd, J=2.4 and 8.4 Hz, 1H), 6.86 (s, 3H), 6.94 (d, J=2.4 Hz, 1H), 7.04 (d, J=2.4 Hz, 1H), 7.23 (d, J=8.4 Hz, 1H), 7.98 (s, 1H).

5-(7-Fluoro-1H-Indol-3-ylmethyl)-3-methyl-2-thioxo-imidazolidin-4-one (893-09):

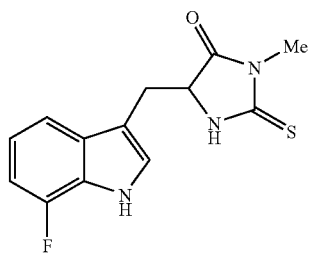

Yield 31%, mp 217-220° C., $^1$H NMR (500 MHz, CDCl$_3$): 3.00-3.05 (dd, J=9.5 and 15.0 Hz, 1H), 3.22 (s, 3H), 3.47-3.51 (dd, J=4.0 and 15.0 Hz, 1H), 4.36-4.39 (m, 1H), 6.83 (s, 1H), 6.94-6.98 (m, 1H), 7.06-7.10 (m, 1H), 7.15 (d, J=2.0 Hz, 1H), 7.36 (d, J=8.0 Hz, 1H), 8.32 (s, 1H). Anal. Calcd for $C_{13}H_{12}FlN_3OS$: C, 56.30; H, 4.36; N, 15.15. Found: C, 56.12; H, 4.39; N, 14.88.

5-(7-Bromo-1H-indol-3-ylmethyl)-3-methyl-2-thioxo-imidazolidin-4-one (893-12):

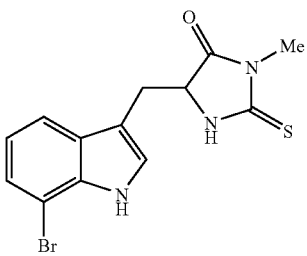

Yield 34%, mp 230-233° C., ¹H NMR (500 MHz, CDCl₃): 2.99-3.05 (dd, J=10 and 15.0 Hz, 1H), 3.22 (s, 3H), 3.46-3.50 (dd, J=4.0 and 15.0 Hz, 1H), 4.35-4.38 (m, 1H), 6.84 (s, 1H), 7.06 (t, J=7.5 Hz, 1H), 7.10 (d, J=2.5 Hz, 1H), 7.40 (d, J=7.5 Hz, 1H), 7.54 (d, J=7.5 Hz, 1H), 8.32 (s, 1H).

5-(7-Chloro-1H-indol-3-ylmethyl)-3-methyl-2-thioxo-imidazolidin-4-one (893-10):

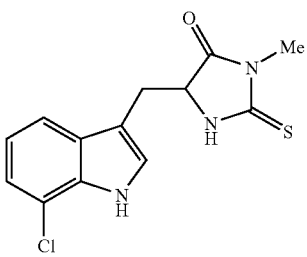

Yield 29%, mp 249-253° C., ¹H NMR (500 MHz, DMSO-d₆-CDCl₃): 3.02 (s, 3H), 3.18-3.22 (dd, J=5.5 and 14.5 Hz, 1H), 3.30-3.34 (dd, J=4.5 and 14.5 Hz, 1H), 4.35 (dd, J=4.5 and 5.5 Hz, H), 7.00 (t, J=7.5 Hz, 1H), 7.13 (d, J=7.5 Hz, 1H), 7.19 (d, J=2.0 Hz, 1H), 7.52 (d, J=7.5 Hz, 1H), 9.92 (s, 1H), 10.45 (s, 1H). Anal. Calcd for $C_{13}H_{12}ClN_3OS$: C, 53.15; H, 4.12; N, 12.07. Found: C, 53.16; H, 4.21; N, 14.01.

5-(6-Chloro-1H-indol-3-ylmethyl)-3-methyl-2-thioxo-imidazolidin-4-one (893-11):

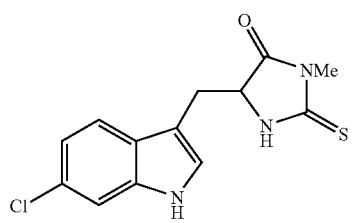

Yield 31%, ¹H NMR (500 MHz, DMSO-d₆): 3.13 (m, 1H), 3.30 (m, 1H), 3.32 (s, 3H), 4.55-4.47 (m, 1H), 6.97-6.99 (dd, J=2.5 and 8.5 Hz, 1H), 7.19 (s, 1H), 7.35 (d, J=2.5 Hz, 1H), 7.53 (d, J=8.5 Hz, 1H), 10.33 (s, 1H), 11.03 (s, 1H).

5-(7-Methoxy-1H-indol-3-ylmethyl)-3-methyl-2-thioxo-imidazolidin-4-one (893-13):

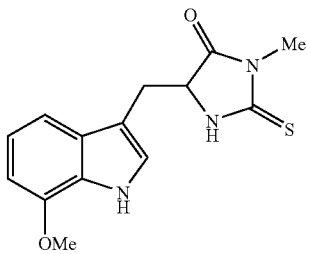

Yield 12%, mp 219-222° C., ¹H NMR (500 MHz, CDCl₃): 2.94-2.99 (dd, J=10 and 15.0 Hz, 1H), 3.23 (s, 3H), 3.48-3.52 (dd, J=4.0 and 15.0 Hz, 1H), 3.92 (s, 3H), 4.36-4.39 (m, 1H), 6.69 (d, J=7.5 Hz, 1H), 6.82 (s, 1H), 7.07-7.11 (m, 2H), 7.19 (d, J=8.0 Hz, 1H), 8.33 (s, 1H).

5-(7-Chloro-1methyl)-3-methyl-2-thioxo-imidazolidin-4-one (893-15):

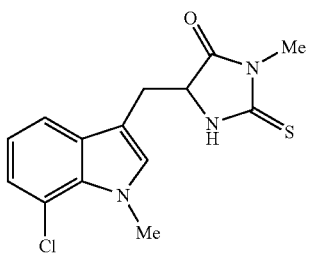

Yield 10%, mp 128-131° C., ¹H NMR (500 MHz, CDCl₃): 2.91-2.96 (dd, J=9.5 and 15.5 Hz, 1H), 3.23 (s, 3H), 3.43-3.47 (dd, J=4.0 and 15.5 Hz, 1H), 4.12 (s, 3H), 4.31-4.33 (m, 1H), 6.81 (s, 1H), 6.90 (s, 1H), 7.02 (dd, J=8.0 and 9.5 Hz, 1H), 7.18 (d, J=7.5 Hz, 1H), 7.44 (d, J=7.5 Hz, 1H).

5-(7-Chloro-5-methanesulfonyl-1H-indol-3-ylmethyl)-3-methyl-2-thioxo-imidazolidin-4-one (893-16):

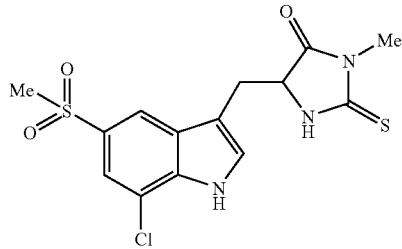

Yield 26%, mp 242-245° C., ¹H NMR (500 MHz, CDCl₃): 3.12 (s, 3H), 3.13 (s, 3H), 3.19-3.23 (dd, J=8.0 and 15.0 Hz, 1H), 3.42-3.46 (dd, J=4.0 and 15.0 Hz, 1H), 4.41-4.44 (m, 1H), 7.11 (s, 1H), 7.33 (d, J=2.5 Hz, 1H), 7.80 (s, J=1.0 Hz, 1H), 8.17 (d, J=1.0 Hz, 1H), 8.67 (s, 1H).

3-Methyl-5-(1H-pyrrolo [2,3-b]pyridin-3-ylmethyl)-2-thioxo-imidazolidin-4-one (893-29):

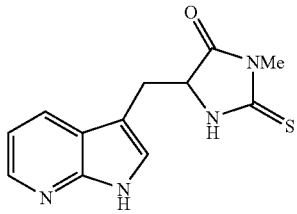

Yield 41%, $^1$H NMR (500 MHz, DMSO-d$_6$): 2.73 (s, 3H), 3.14-3.16 (m, 2H), 4.55-4.58 (m, 1H), 7.16-7.32 (m, 2H), 8.24-8.32 (m, 2H), 10.29 (s, 1H), 10.10 (s, 1H).

3-[Hydroxy-1-(methyl-5-oxo-2-thioxo-imidazolidin-4-yl)methyl]-indole-1-carboxylic acid tert-butyl ester (893-55):

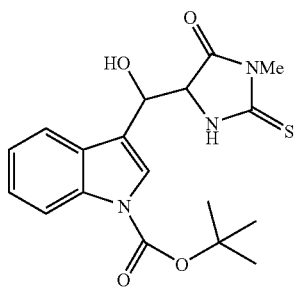

Yield 18%, $^1$H NMR (500 MHz, CDCl$_3$): 1.69 (s, 9H), 2.30 (m, 1H), 4.47 (m, 1H), 5.37 (m, 1H), 6.69 (s, 1H), 7.26-7.41 (m, 2H), 7.59 (d, J=7.5 Hz, 1H), 7.67 (s, 1H), 8.21 (d, J=8.5 Hz, 1H).

Example 10

Preparation of 5-(1H-Indol-3-ylmethyl)-3-(2-morph-lin-4-yl-ethyl)-2-thioxo-imidazolidin-4-one (893-17)

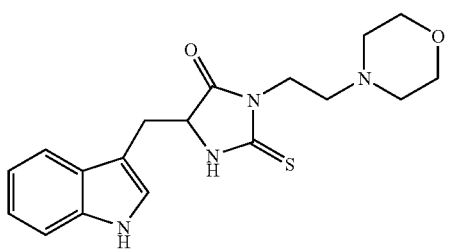

To a solution of L-tryptophan methyl ester hydrochloride (0.250 mg, 0.001 mol.) in dichloromethane (10 mL) was added triethyl amine (3.0 eq.) followed by 4-(2-isothiocyanato-ethyl)-morpholine (0.190 gm, 0.0011 mol.). The reaction mixture was stirred at room temperature for 24 hr, and then concentrated. The residue obtained was purified by column chromatography on silica gel using 60% ethyl acetate-hexane to give 893-17 (292 mg, 83%): mp 167-169° C., $^1$H NMR (500 MHz, CDCl$_3$): 2.45-2.51 (m, 6H), 3.02-3.07 (dd, J=9.5 and 15.0 Hz, 1H), 3.46-3.50 (dd, J=4.0 and 15.0 Hz, 1H), 3.65 (m, 4H) 3.89 (d, J=7.0 Hz, 2H), 4.35-4.38 (m, 1H), 6.38 (s, 1H), 7.12 (d, J=2.5 Hz, 1H), 7.16-7.19 (m, 1H), 7.23-7.25 (dd, J=1.5 and 8.0 Hz, 1H), 7.39 (d, J=8.5 Hz, 1H), 7.61 (d, J=8.5 Hz, 1H), 8.15 (s, 1H).

Example 11

Preparation of 5-(1H-indol-3-ylmethyl)-2-thioxo-imidazolidin-4-one (893-18)

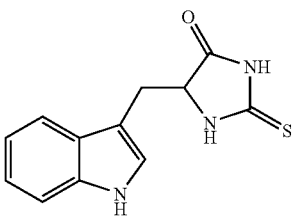

To a solution of L-tryptophan methyl ester hydrochloride (0.257 mg, 0.001 mol.) in dichloromethane (10 mL) was added DMAP (5.0 mg), diisopropylethylamine (10 eq.) and then trimethylsilylisothiocyanate (1.3 gm, 0.01 mol.). The reaction mixture was stirred at room temperature for 24 hr, and then concentrated. The residue obtained was dissolved in AcOH (10 mL) and refluxed for 6 h. The reaction mixture was concentrated and dried under vacuum. The solid obtained was suspended in EtOAc, filtered, washed with EtOAc, and dried under vacuum to give 893-18 (230 mg, 94%): mp 206-210° C., $^1$H NMR (500 MHz, DMSO-d$_6$): 3.00-yield 34%, $^1$H NMR (500 MHz, CDCl$_3$): 3.24-3.33 (m, 2H), 4.23-4.26 (m, 1H), 7.01(dd, J=8.0 and 7.0 Hz, 1H), 7.09 (dd, J=8.0 and 7.0 Hz, 1H), 7.23 (d, J=2.0 Hz, 1H), 7.37 (d, J=8.0 Hz, 1H), 7.50 (d, J=8.0 Hz, 1H), 8.50 (s, 2H), 11.08 (s, 1H).

Example 12

Preparation of 3-Ethyl-5-(1H-indol-3-ylmethyl)-imidazolidine-2,4-dione (893-04)

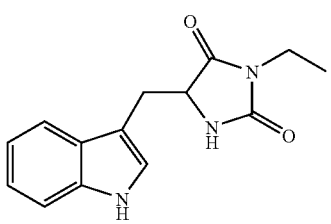

To a solution of L-tryptophan methyl ester hydrochloride (0.510 mg, 0.002 mol.) in dichloromethane (10 mL) was added triethyl amine (0.350 mL, 0.0025 mol.) followed by ethylisocyanate (0.198 mL, 0.0025 mol.). The reaction mixture was stirred at room temperature for 24 hr, and then concentrated. The residue obtained was diluted with dioxane (10 mL) and then conc. HCl (5 mL) was added. The mixture was heated at reflux for 3-4 hr. The reaction mixture was extracted in ethyl acetate, washed with water, dried and concentrated. The residue was purified by column chromatography on silica gel using 60% ethyl acetate-hexane to give 893-04 (480 mg, 93%): mp 167-170° C. (lit. 163-164° C.), $^1$H NMR (400 MHz, CDCl$_3$): 0.99 (t, J=6.8 Hz, 3H), 2.95-3.01 (dd, J=8.4 and 14.8 Hz, 1H), 3.34-3.46 (m, 3H), 4.19-4.22

(dd, J=3.6 and 8.8 Hz, 1H), 5.70 (s, 1H), 6.98 (d, J=2.0 Hz, 1H), 7.06-7.10(dd, J=8.0 and 6.8 Hz, 1H), 7.16(dd, J=7.2 and 6.8 Hz, 1H), 7.30 (d, J=8.4 Hz, 1H), 7.55 (d, J=8.8 Hz, 1H), 8,18 (s, 1H).

Example 13

Preparation of 5-(1H-indol-3-ylmethyl)-imidazolidine-2,4-dione (893-19)

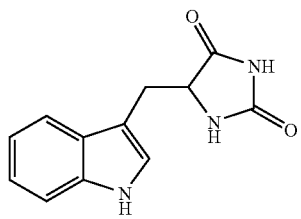

To a solution of L-tryptophan methyl ester hydrochloride (0.500 mg, 0.002 mol.) in dichloromethane (10 mL) was added triethyl amine (3.0 mL) followed by trimethylsilylisocyanate (2.300 gm, 0.02 mol.). The reaction mixture was stirred at room temperature for 24 hr and then concentrated. The residue obtained was dissolved in AcOH (5 mL) and refluxed for 5 hr. The reaction mixture was extracted in ethyl acetate, washed with water, dried and concentrated. The residue was dissolved in EtOH and treated with KOH, and stirred for 30 min. Then the reaction was concentrated and dried under vacuum to give 5-(1H-indol-3-ylmethyl)-imidazolidine-2,4-dione potassium salt (245 mg, 46%). This solid (50 mg, 0.18 mg) was acidified with dilute HCl at 0° C. The residue was extracted in ethyl acetate, and concentrated. The solid obtained after concentration was dried under vacuum to give 893-19 (42 mg, 93%): mp 229-232° C., $^1$H NMR (500 MHz, DMSO-d$_6$): 3.00-3.10 (m, 1H), 3.23-3.27 (dd, J=4.0 and 14.5 Hz, 1H), 4.24-4.26 (m, 1H), 7.01(dd, J=7.5 and 7.0 Hz, 1H), 7.09(dd, J=7.0 and 7.5 Hz, 1H), 7.13 (d, J=1.0 Hz, 1H), 7.34-7.36 (m, 2H), 7.60 (d, J=8.0 Hz, 1H), 10.26 (s, 1H), 10.33 (s, 1H).

Example 14

Preparation of 3-Methyl-5-(1H-indol-3-ylmethyl)-imidazolidine-2,4-dione (893-20)

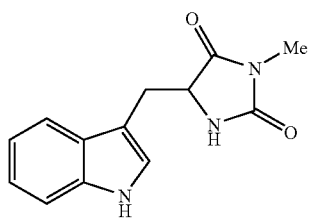

5-(1H-indol-3-ylmethyl)-imidazolidine-2,4-dione potassium salt (200 mg, 0.75 mmol.) obtained from above reaction was dissolved in DMF (5 mL), and treated with MeI (3 eq.). The reaction mixture was stirred at room temperature for 30 min., and then extracted with ethyl acetate, washed with water, dried and concentrated. The solid obtained after concentration was recrystallized from ethyl acetate to give 893-20 (168 mg, 92%): mp 207-210° C. (lit. mp 207-209° C.), $^1$H NMR (500 MHz, CDCl$_3$-DMSO-d$_6$): 2.80 (s, 3H), 3.08-3.12 (dd, J=7.0 and 14.5 Hz, 1H), 3.28-3.31 (dd, J=4.0 and 14.5 Hz, 1H), 4.25-4.28 (m, 1H), 7.00-7.10 (m, 3H), 7.35 (d, J=7.5 Hz, 1H), 7.57 (d, J=8.0 Hz, 1H), 7.79 (s, 1H), 10.39 (s, 1H). Anal. Calcd for C$_{13}$H$_{13}$N$_3$O$_2$: C, 64.19; H, 5.39; N, 17.27. Found: C, 63.98; H, 5.44; N, 17.24.

Example 15

Preparation of 5-(5-Chloro-benzo[b]thiophen-3-ylmethyl)-3-methyl-imidazolidine-2,4-dione (893-14)

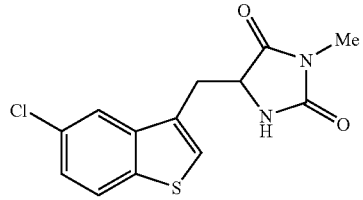

To a mixture of 2-Amino-3-(5-chloro-benzo[b]thiophen-3-yl)-propionic acid (255.7 mg, 1.0 mmol) in methanol was added thionyl chloride (0.08 mL) at 0° C. The resulting mixture was heated at reflux for 7 h, allowed to cool to room temperature, diluted with saturated sodium bicarbonate and extracted with ethyl acetate (2×30 mL). The organic extracts were combined, washed with brine (25 mL), dried over anhydrous sodium sulfate, filtered, and concentrated to give a yellow oil (2-amino-3-(5-chloro-benzo[b]thiophen-3-yl)-propionic acid methyl ester).

The oil (257 mg, 0.95 mmol) was dissolved in dichloromethane (20 mL) and then methyl isothiocyanate (70 mg, 0.95 mmol) was added. The reaction mixture was heated at reflux for 24 h. The reaction mixture was allowed to cool to room temperature and then concentrated. The residue was purified by column chromatography using hexane/ethyl acetate (75:25) as eluent to give a colorless oil (3-(5-chloro-benzo[b]thiophen-3-yl)-2-(3-methyl-thioureido)propionic acid methyl ester).

The oil (193 mg, 0.563 mmol) was stirred in dioxane (4 mL) with concentrated HCl (2 mL) at 100° C. for 3 h. The mixture was allowed to cool to room temperature, diluted with water and extracted with ethyl acetate. The organic layer was dried over anhydrous magnesium sulfate, filtered, and concentrated to give a yellow solid. The solid was purified by column chromatography using hexane/ethyl acetate (80:20) as eluent to give 893-14 as a white solid: $^1$H NMR (500 MHz, DMSO-d$_6$): 2.94 (s, 3H), 3.23-3.32 (m, 2H), 4.66 (dt, J=1.0 and 5.5 Hz, 1H), 7.39 (dd, J=2.0 and 8.5 Hz, 1H), 7.56 (s, 1H), 7.35 (d, J=7.5 Hz, 1H), 7.92 (d, J=2.0 Hz, 1H), 8.01 (d, J=8.5 Hz, 1H), 10.96 (s, 1H).

Example 16

Procedure used for the preparation of 1-4.
Exemplified for the preparation of
6-chloroindole-3-carboxaldehyde (1)

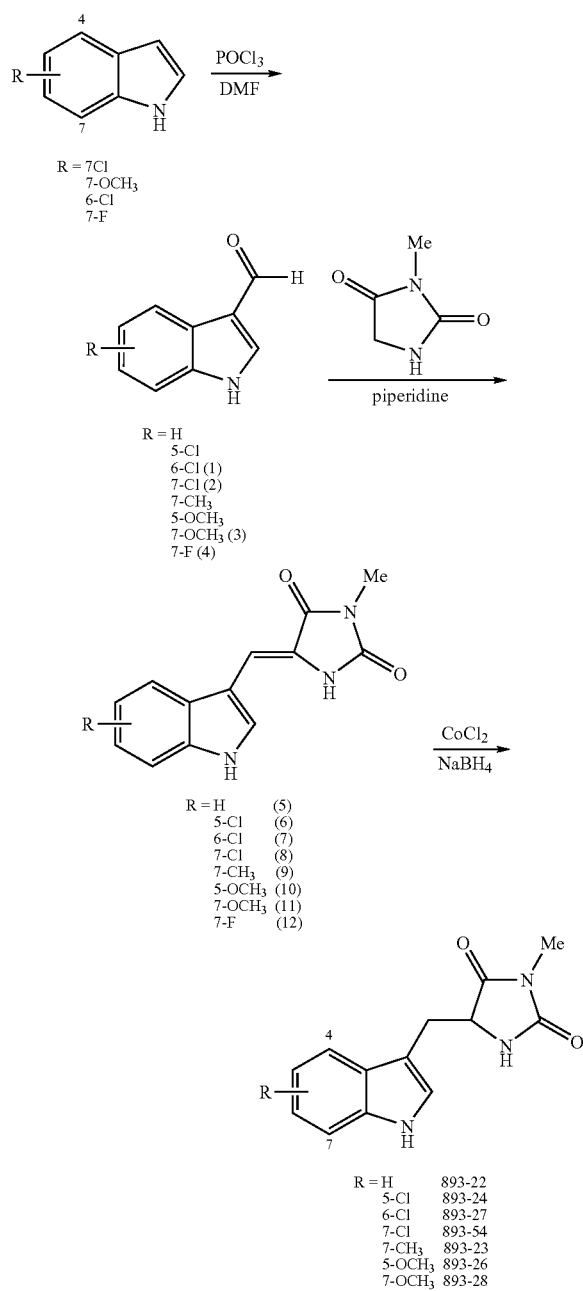

Phosphorus oxychloride (0.66 mL, 7 mmol) was added dropwise to anhydrous DMF (5 mL) at 0° C. under argon. A solution of 7-chloroindole (1 g, 6.6 mmol) in anhydrous DMF (15 mL) was added dropwise at room temperature and the resulting mixture was stirred for 2 h. The reaction mixture was poured into ice and saturated NaHCO$_3$ and extracted with ethyl acetate. The combined organic solutions were washed with saturated NaCl (10 mL×3), dried over anhydrous MgSO$_4$, filtered and concentrated to give 990 mg of product, 1, as a yellow-orange solid (83%). $^1$NMR (500 MHz, DMSO-d$_6$) δ 12.22 (1H, br s), 9.93 (1H, s), 8.34 (1H, s), 8.07 (1H, d, J=9.0 Hz), 7,57(1H, d, J=1.5), 7.25 (1H, dd, J=1.8, 7.8 Hz).

(2)$^1$NMR (500 MHz, DMSO-d$_6$) δ 12.54 (1H, br s), 9.97 (1H, s), 8.39 (1H, s) 8.06 (1H, dd, J=1.3, 7.8 Hz), 7.37 (1H, dd, J=1.0, 7.5), 7.23 (1H, t, J=7.8 Hz,).

(3)$^1$NMR (500 MHz, DMSO-d$_6$) δ 12.32 (1H, br s), 9.92 (1H, s), 8.17 (1H, d, J=2.5), 7.66 (1H, d, J=8.0 Hz), 7.14 (1H, t, J=7.5 Hz), 6.84 (1H, d, J=7.5 Hz), 3.94 (3H, s).

(4)$^1$NMR (500 MHz, DMSO-d$_6$) δ 12.69 (1H, br s), 9.97 (1H, s), 8.37 (1H, s) 7.90 (1H, d, J=8.5 Hz), 7.20 (1H, dt, J=4.5, 8.0), 7.17 (1H, dd, J=7.5, 10.5 Hz).

Procedure used for the preparation of 5-12. Exemplified for the preparation of 5-(1H-Indol-3-ylmethylene)-3-methylimidazolidine-2,4-dione (5). A mixture of indole-3-carboxaldehyde (146 mg, 1 mmol) and 1-methylimidazol-2,5(1,3H)-dione (synthesized according to the method used in Eur. J. Org. Chem. 2002, 1763-1769) (250 mg, 2.5 mmol) in piperidine (2 mL) was heated at 110° C. for 4 h under an argon atmosphere. Then the reaction mixture was allowed to cool in a refrigerator (~5° C.) with the addition of ether (2 mL). The precipitate was filtered and washed with ether to give 5 as a yellow solid (171 mg, 71%). $^1$NMR (500 MHz, DMSO-d$_6$): δ 11.84 (1H, br s), 10.29 (1H, br s), 8.15 (1H, s), 7.79 (1H, d, J=7.5 Hz), 7.43 (1H, d, J=8.5 Hz), 7.18 -7.12 (1H, m), 7.13 (1H, td, J=1.0, 7.8), 6.86 (1H, s), 2.97 (3H, s).

Remark: For products that did not precipitate from reaction mixtures, ethyl acetate (200 mL) was added. The resulting solutions were washed sequentially with 1N HCl (50 mL×2), saturated NaHCO$_3$ (50 mL×2), saturated NaCl (50 mL), and then dried over anhydrous MgSO$_4$ with the addition of 20 mL of MeOH. The mixtures were filtered and evaporated to gives solids. Then 20 to 30% ethyl acetate in hexane solutions was added. The solid was filtered, washed with the same solvent to give the products as yellow solids. These solids were used without further purification.

(6) $^1$NMR (500 MHz, DMSO-d$_6$): δ 12.01 (1H, br s), 10.34 (1H, br s), 8.19 (1s), 7.90 (1H, d, J=2.5 Hz), 7.44 (1H, d, J=9.0 Hz), 7.19 (1H, dd, J=2.0, 8.8 Hz), 6.85 (1H, s), 2.97 (3H, s).

(7) $^1$NMR (500 MHz, DMSO-d$_6$): δ 11.95 (1H, br s), 10.37 (1H, br s), 8.17 (1d, J=3.0), 7.83 (1H, d, J=9.0 Hz), 7.47 (1H, d, J=2.0 Hz), 7.13 (1H, dd, J=2.0, 8.5 Hz), 6.83 (1H, s), 2.97 (3H, s).

(8) $^1$NMR (500 MHz, DMSO-d$_6$): δ 12.15 (1H, br s), 10.26 (1H, br s), 8.23 (1H), s), 7.79 (1H, d, J=8.0 Hz), 7.27 (1H, d, J=8.0 Hz,), 7.13 (1H, t, J=7.8 Hz), 6.82 (1H, s), 2.97 (3H, s).

(9) $^1$NMR (500 MHz, DMSO-d$_6$): δ 11.80 (1H, br s), 10.35 (1H, br s), 8.16 (1H), d, J=3.0), 7.60 (1H, d, J=8.0 Hz), 7.04 (1H, t, J=7.5 Hz), 6.99 (1H, d, J=7.5 Hz), 6.84 (1H, s), 2.97 (3H, s), 2.48 (3H, s).

(10) $^1$NMR (500 MHz, DMSO-d$_6$): δ 11.71 (1H, br s), 10.27 (1H, br s), 8.09 (1H), s), 7.31 (1H, d, J=7.0 Hz), 7.30 (1H, s), 6.89 (1H, s), 6.81 (1H, dd, J=2.5, 8.5 Hz), 3.82 (3H, s), 2.97 (3H, s).

(11) $^1$NMR (500 MHz, DMSO-d$_6$): δ 11.94 (1H, br s), 10.33 (1H, br s), 8.09 (1H), d, J=3.0 Hz), 7.35 (1H, d, J=7.5 Hz), 7.06 (1H, t, J=7.8 Hz,), 6.81 (1H, s), 6.76 (1H, d, J=7.5), 3.93 (3H, s), 2.97 (3H, s).

(12) $^1$NMR (500 MHz, DMSO-d$_6$): δ 12.30 (1H, br s), 10.36 (1H, br s), 8.20 (1H), s), 7.63 (1H, d, J=8.0 Hz), 7.10 (1H, dt, J=5.0, 8.0 Hz), 7.03 (1H, dd, J=7.5, 11.0 Hz), 6.82 (1H, s), 2.97 (3H, s).

Procedure used for the preparation of 5-(1H-Indol-3-ylmethyl)-3-methylimidazolidine-2,4-diones. Exemplified for the preparation of 5-(1H-Indol-3-ylmethyl)-3-methylimidazolidine-2,4-dione (893-22). To a solution of 5-(1H-Indol-3-ylmethylene)-3-methylimidazolidine-2,4-dione (5) (120 mg, 0.5 mmol) in a mixed solvent of anhydrous MeOH/THF (1:1, 40 mL) were added CoCl$_2$ (130 mg, 1.0 mmol) and NaBH$_4$ (380 mg, 10 mmol) portion wise. The mixture was stirred at room temperature overnight and then diluted with ethyl acetate (100 mL). The mixture was washed sequentially with saturated NaHCO$_3$ (30 mL), 1N HCl (30 mL), saturated NaCl (30 mL) and then dried over anhydrous MgSO$_4$, filtered and concentrated. The crude product was purified by column chromatography on silica gel using 50% ethyl acetate n hexane as eluent to give 893-22 as a white solid (80 mg, 66%). $^1$H NMR (500 MHz, CDCl$_3$): δ 8.14 (1H, br s), 7.61 (1H, d, J=7.0 Hz), 7.39 (1H, d, J=8.0 Hz), 7.22-7.25 (1H, m), 7.16 (1H, t, J=7.8 Hz), 7.09 (1H, d, J=2.5), 5.32 (1H, br s), 4.30 (1H, ddd, J=1.0, 3.5, 10.0 Hz), 3.50 (1H, dd, J=4.0, 15.0 Hz), 2.99 (3H, s), 2.94-2.97 (1H, m).

(893-24) $^1$H NMR (500 MHz, CDCl$_3$): δ 8.17 (1H, br s), 7.58 (1H, d, J=2.0 Hz), 7.30 (1H, d, J=8.5 Hz), 7.18 (1H, dd, J=2.0, 8.5 Hz), 7.12 (1H, d, J=2.5 Hz), 5.26 (1H, br s), 4.30 (1H, ddd, J=1.0, 3.7, 9.4 Hz), 3.43 (1H, dd, J=3.8, 14.8 Hz), 2.99 (3H, s), 2.94-3.00 (1H, m).

(893-27) $^1$H NMR (500 MHz, CDCl$_3$): δ 8.13 (1H, br s), 7.51 (1H, d, J=9.0 Hz), 7.39 (1H, d, J=2.0 Hz), 7.13 (1H, dd, J=1.8, 8.8 Hz), 7.09 (1H, d, J=2.5 Hz), 5.20 (1H, br s), 4.28 (1H, ddd, J=2.5, 3.8, 9.0 Hz), 3.44 (1H, dd, J=3.5, 15.0 Hz), 2.99 (1H, dd, J=9.0, 14.5 Hz), 2.97 (3H, s).

(893-54) $^1$H NMR (500 MHz, CDCl$_3$): δ 8.43 (1H, br s), 7.50 (1H, d, J=8.0 Hz), 7.22 (1H, d, J=7.5 Hz), 7.13 (1H, d, J=2.0 Hz), 7.06 (1H, t, J=7.8 Hz), 5.69 (1H, br s), 4.27 (1H, ddd, J=1.0, 3.5, 8.8 Hz,), 3.43 (1H, dd, J=3.5, 14.5 Hz), 3.01 (1H, dd, J=9.3, 14.8 Hz), 2.95 (3H, s).

(893-23) $^1$H NMR (500 MHz, CDCl$_3$): δ 8.08 (1H, br s), 7.46 (1H, d, J=8.0 Hz), 7.03-7.10 (3H, m), 5.30 (1H, br s), 4.30 (1H, ddd, J=1.0, 3.9, 10.1 Hz,), 3.48-3.52 (1H, m), 3.00 (3H, s), 2.95 (1H, dd, J=9.8, 14.8 Hz), 2.50 (3H, s).

(893-26) $^1$H NMR (500 MHz, CDCl$_3$): δ 8.06 (1H, br s), 7.27 (1H, d, J=8.5 Hz), 7.05 (1H, d, J=2.5 Hz), 7.02 (1H, d, J=2.5 Hz), 6.89 (1H, dd, J=2.5, 8.5 Hz), 5.45 (1H, br s), 4.28-4.30 (1H, m), 3.86 (3H, s), 3.44 (1H, dd, J=3.3, 14.8 Hz), 2.98 (3H, s), 2.94 (1H, dd, J=9.3, 14.8 Hz).

(893-25) $^1$H NMR (500 MHz, CDCl$_3$): δ 8.33 (1H, br s), 7.21 (1H, d, J=8.0 Hz), 7.08 (1H, t, J=7.3 Hz), 7.05 (1H, s), 6.68 (1H, d, J=7.5 Hz), 5.22 (1H, br s), 4.29 (1H, dd, J=3.5, 10.0 Hz), 3.97 (3H, s), 3.49 (1H, dd, J=3.5, 14.5 Hz), 3.00 (3H, s), 2.93 (1H, dd, J=10.3, 14.8 Hz).

(893-28) $^1$H NMR (500 MHz, CDCl$_3$): δ 8.35 (1H, br s), 7.36 (1H, d, J=7.5 Hz), 7.11 (1H, d, J=2.0 Hz), 7.05 (1H, dt, J=4.5, 8.0 Hz), 6.93 (1H, dd, J=7.5, 10.5 Hz), 5.38 (1H, s), 4.29 (1H, dd, J=2.5, 9.0 Hz), 3.45 (1H, dd, J=3.5, 15.0 Hz), 2.99 (1H, dd, J=9.0, 15.0 Hz), 2.97 (3H, s).

Example 17

Preparation of Indoles

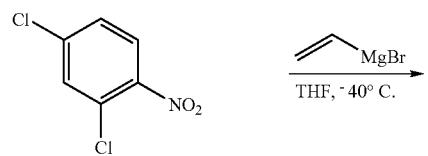

-continued

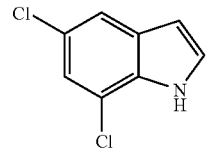

Figure 6:
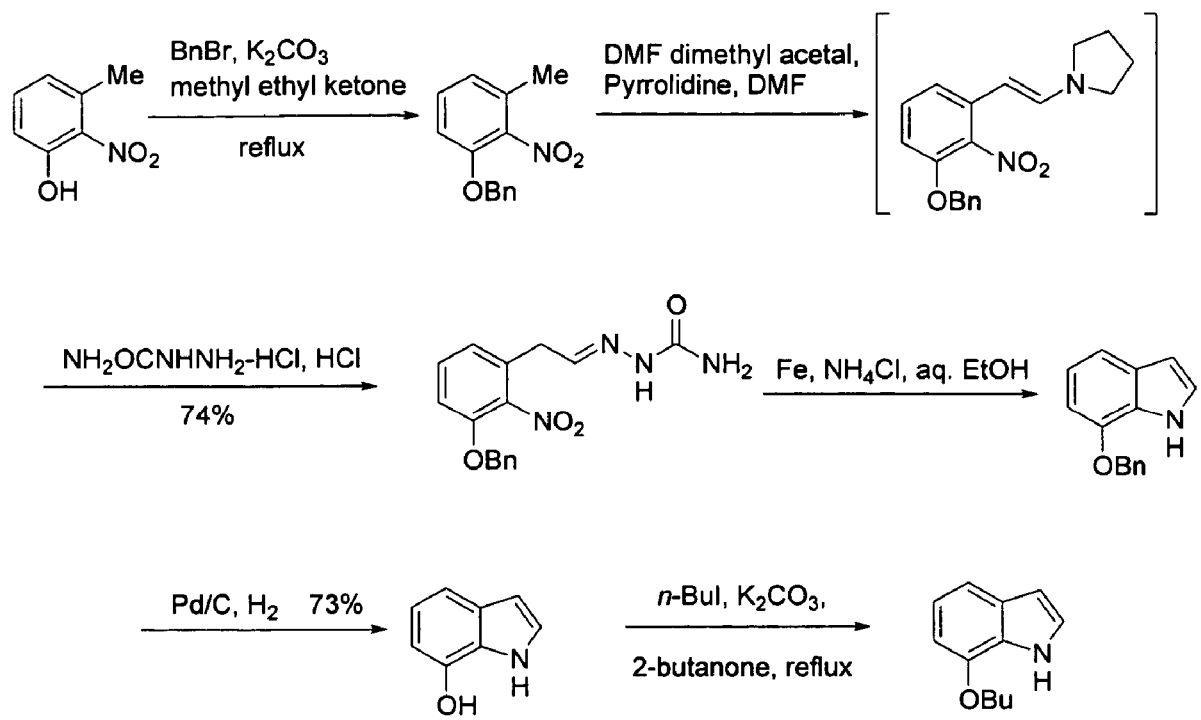
FIG. 6 shows a scheme for the preparation of 7-oxygenated indoles.
Figure 7:
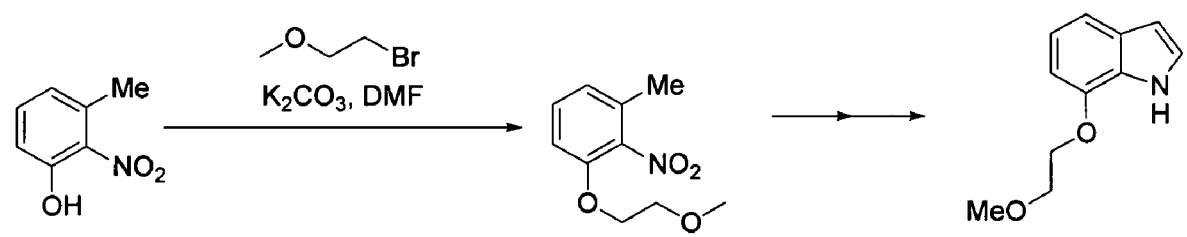
FIG. 7 shows a scheme for the preparation of 7-(2-methoxy-ethoxy)-1H-indole.
Figure 8A:
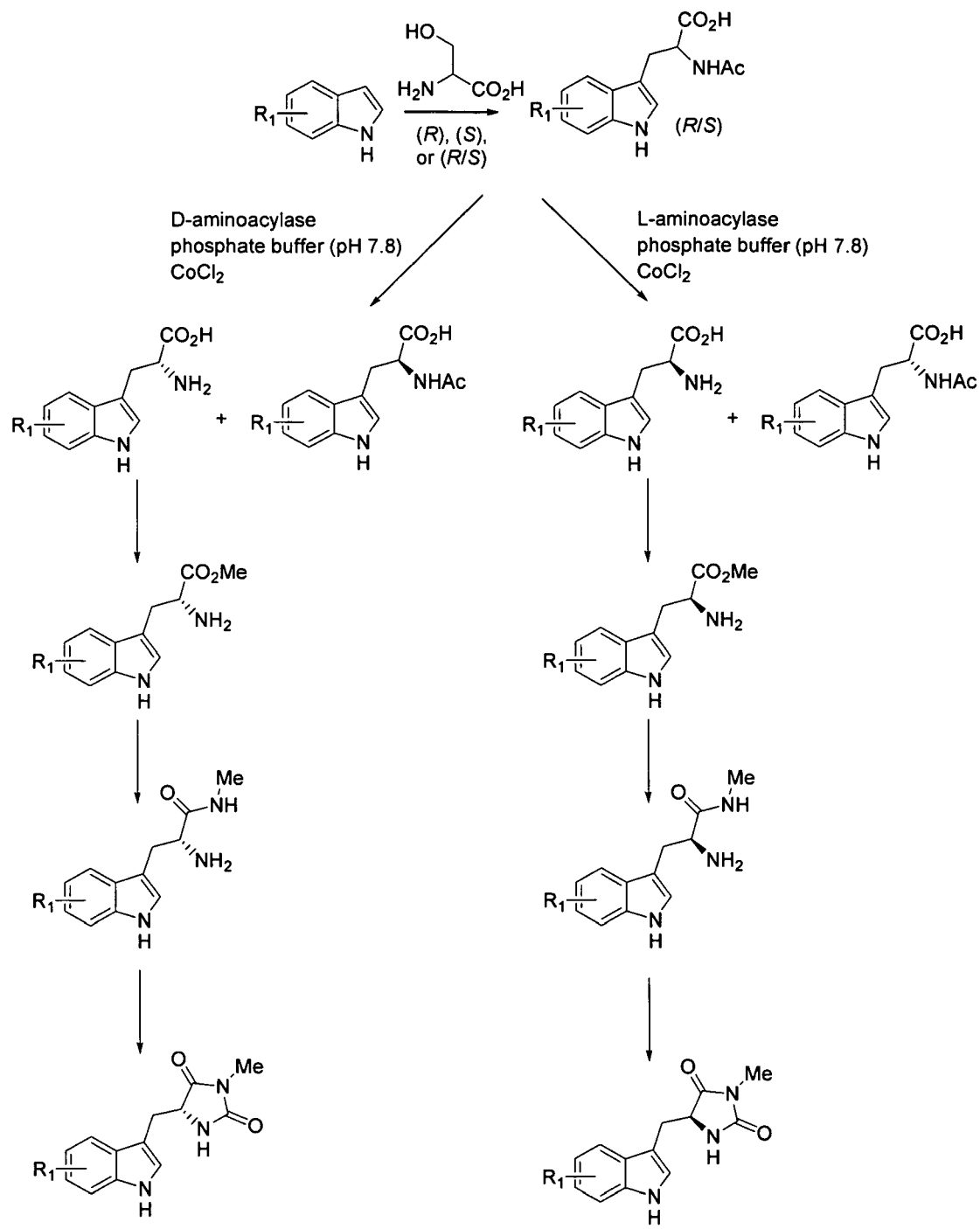
FIG. 8 depicts (A) a general scheme for enantioselectively synthesizing a heterocyclic compound comprising a hydantoin moiety (B) scheme for synthesizing compounds 893-31 and 893-32.
Figure 8B:
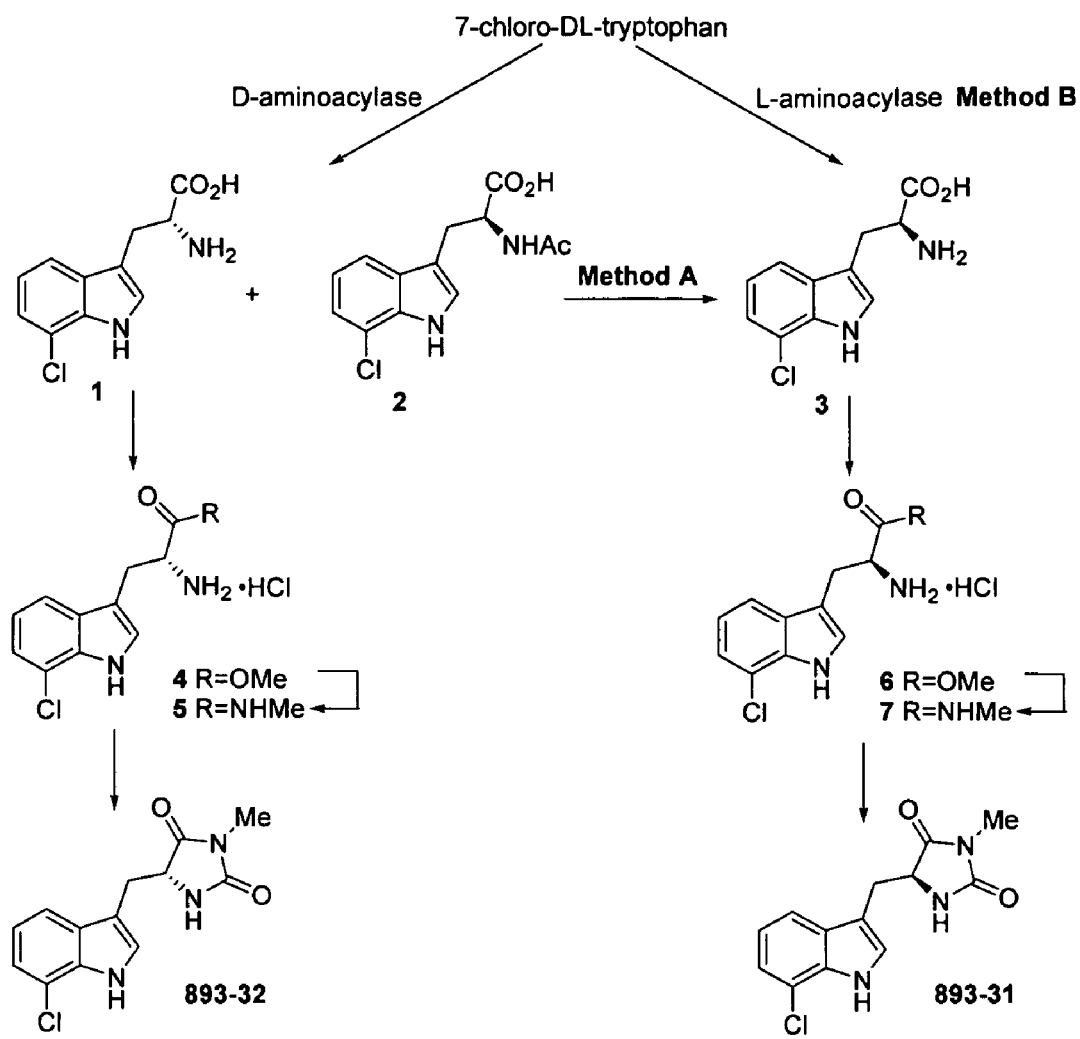
Figure 9:
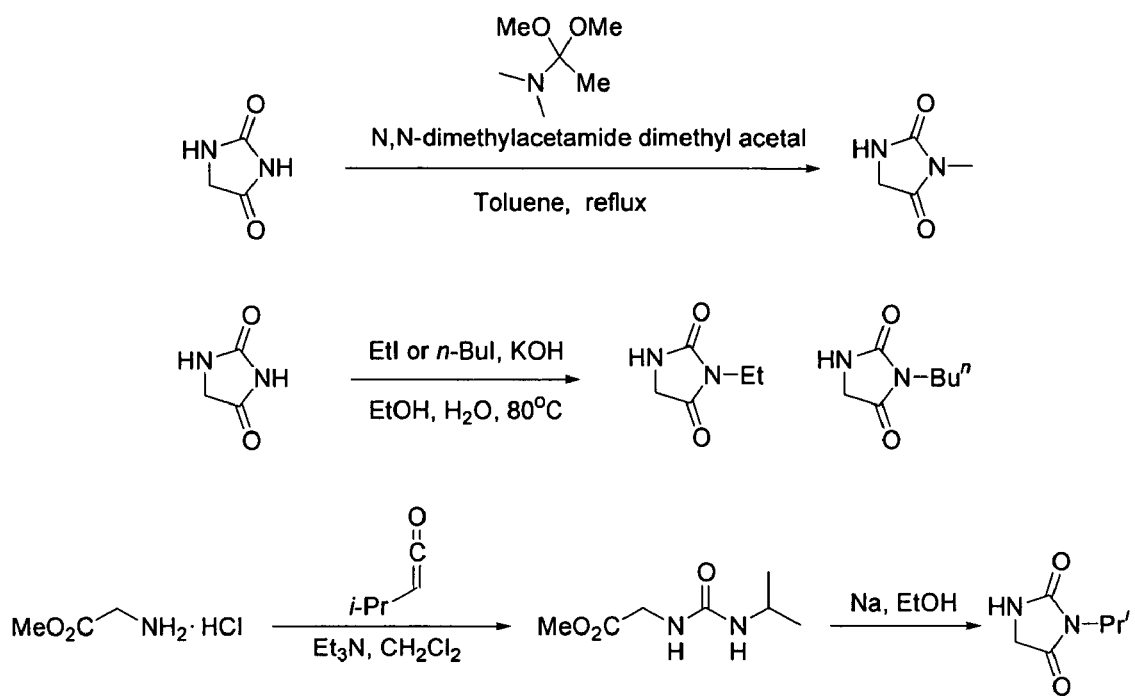
FIG. 9 depicts a general scheme for synthesizing hydantoins.
Figure 10:
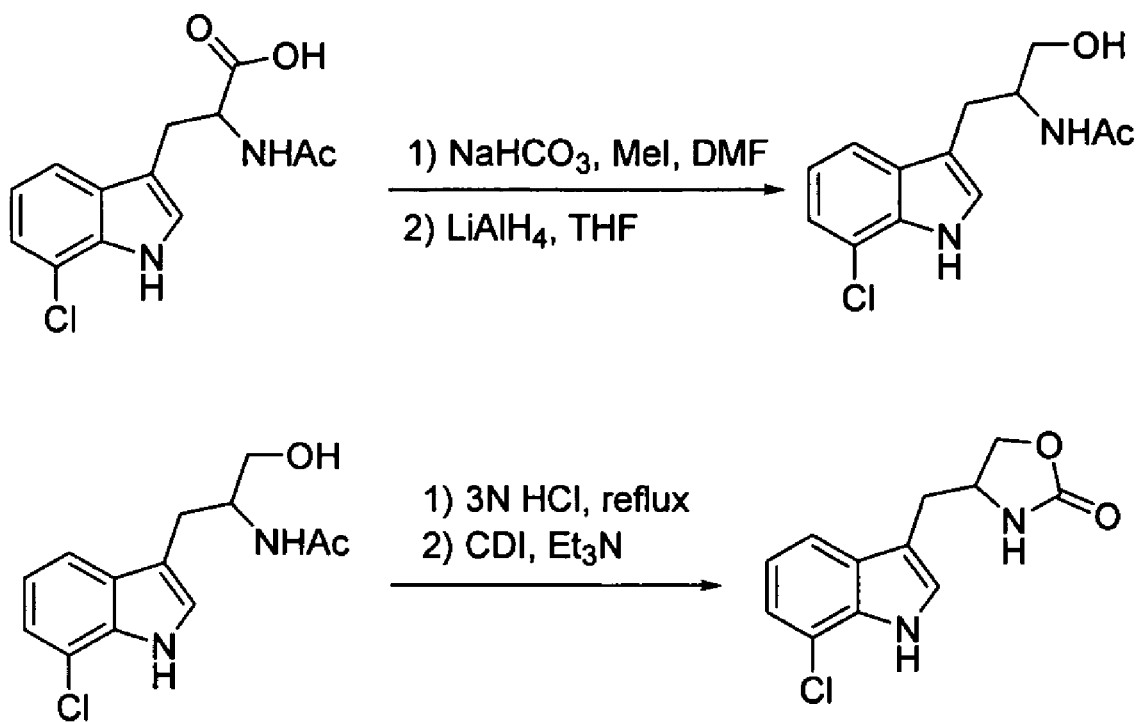
FIG. 10 depicts a general scheme for the preparation of oxazolidinones.

Several indoles needed were prepared utilizing the Bartoli synthesis (Bartoli, G.; Palmieri, G.; Bosco, M.; Dalpozzo R., Tetrahedron Lett., 1989, 2129). An example of this synthesis is illustrated for 5,7-dichloroindole (FIG. 6).

A solution of 1.0 M vinylmagnesium bromide (45.0 mL, 45.0 mmol) was quickly added to a stirred THF solution (30.0 mL) of 2,4-dichloronitrobenzene (2.88 g, 15.0 mmol) cooled at −40° C. under N$_2$. The reaction mixture was stirred for 20 minutes and poured into saturated aqueous ammonium chloride, extracted with ether and dried over anhydrous sodium sulfate. After chromatographic purification on silica gel, the indole was obtained in 46% yield (1.28 g). $^1$H NMR (500 MHz, CDCl$_3$): δ 8.38 (1H, brs), 7.49 (1H, s), 7.52 (1H, d, J=1.5 Hz), 7.28 (1H, t, J=8.0 Hz), 7.20 (1H, d, J=2.0 Hz), 6.54 (1H, dd, J=2.5, 3.5 Hz).

The known indole, 6,7-dichloroindole, and the previously unreported indole, 7-chloro-2-methylindole ($^1$H NMR (500 MHz, CDCl$_3$): δ 8.07 (1H, brs), 7.39 (1H, d, J=7.5 Hz), 7.10 (1H, d, J=7.5 Hz), 6.99 (1H, t, J=8.0 Hz), 6.26-6.24 (1H, m), 2.47 (3H, m) were prepared in a similar manner.

Example 18

Preparation of 7-oxygenated Indoles

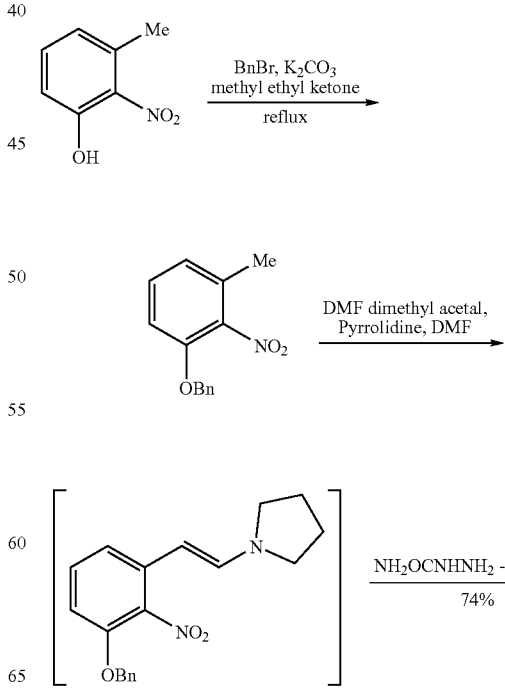

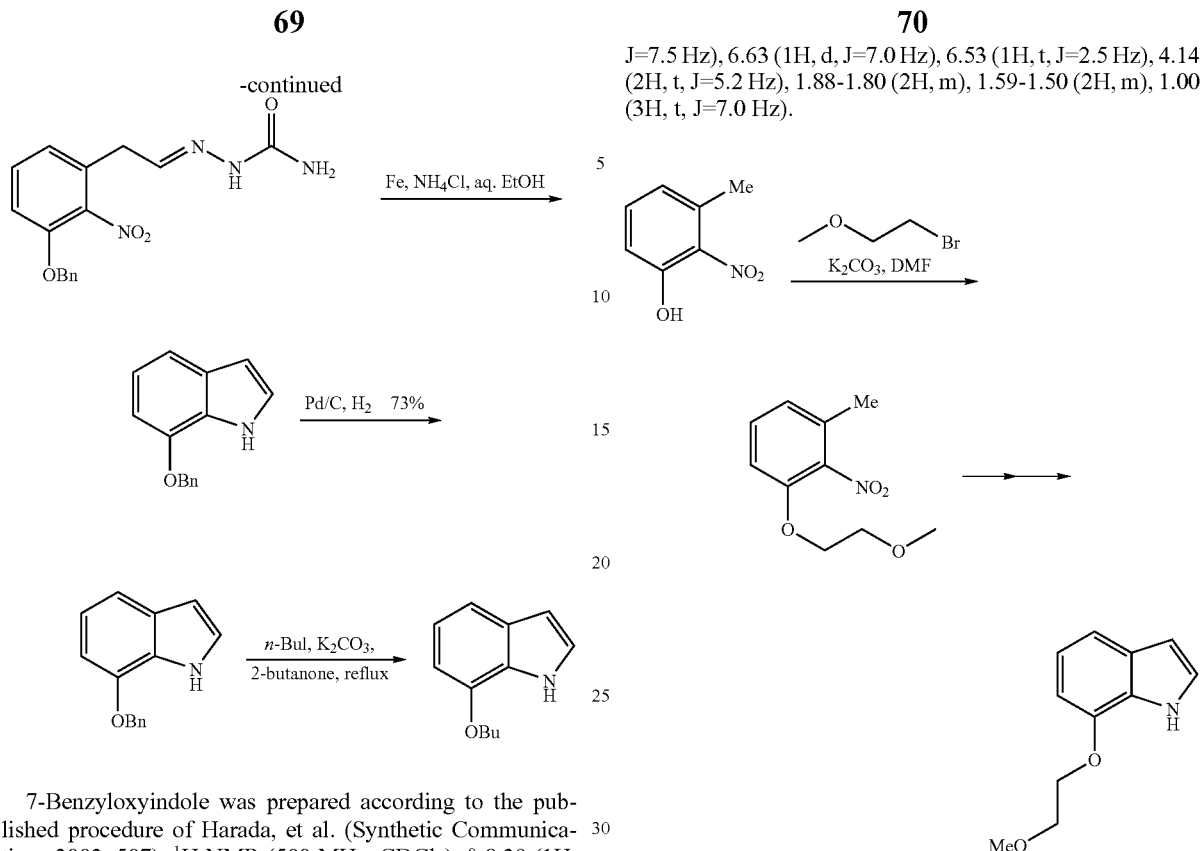

7-Benzyloxyindole was prepared according to the published procedure of Harada, et al. (Synthetic Communications 2003, 507). $^1$H NMR (500 MHz, CDCl$_3$): δ 8.39 (1H, brs), 7.23 (1H, d, J=8.0 Hz), 7.17 (1H, t, J=3.0 Hz), 7.01 (1H, t, J=7.5 Hz), 6.63 (1H, d, J=7.0 Hz), 6.53 (1H, t, J=2.5 Hz), 4.14 (2H, t, J=6.5 Hz), 1.88-1.80 (2H, m), 1.59-1.50 (2H, m), 1.00 (3H, t, J=7.0 Hz).

Furthermore, 7-benzyloxyindole (404 mg, 1.81 mmol) was hydrogenated over 10% palladium on carbon (40 mg) in EtOH (4.2 mL) at ambient temperature under atmosphere pressure for 6 h. The catalyst was filtered off and washed with EtOH. The filtrate was concentrated to give 7-hydroxyindole as pale purple crystals, which was rapidly and directly used for the next reaction.

To a stirred solution of 7-hydroxyindole and potassium carbonate (325 mg, 2.35 mmol) in methyl ethyl ketone (2.4 mL) was added iodobutane (1.24 mL, 10.8 mmol) at room temperature. After the mixture was heated at 55° C. for 12 h the solvent was removed and water was added. The mixture was extracted with EtOAc (3 times), dried over anhydrous MgSO$_4$, filtered and evaporated. After chromatographic purification on silica gel, 7-n-butoxyindole was obtained in 90% yield (310 mg). $^1$H NMR (500 MHz, CDCl$_3$) δ 8.39 (1H, brs), 7.23 (1H, d, J=8.0 Hz), 7.17 (1H, t, J=3.0 Hz), 7.01 (1H, t, J=7.5 Hz), 6.63 (1H, d, J=7.0 Hz), 6.53 (1H, t, J=2.5 Hz), 4.14 (2H, t, J=5.2 Hz), 1.88-1.80 (2H, m), 1.59-1.50 (2H, m), 1.00 (3H, t, J=7.0 Hz).

7-(2-Methoxy-ethoxy)-1H-indole was prepared in a similar as described above for the 7-benzyloxyindole.

The required 1-(2-methoxy-ethoxy)-3-methyl-2-nitrobenzene was prepared from 3-methyl-2-nitrophenyl. To a stirred solution of the phenyl (2.0 g, 13.1 mmol) in DMF (65 mL) was added potassium carbonate (2.16 g, 15.7 mmol) and bromoethyl methyl ether (1.47 mL, 15.7 mmol) at room temperature. After the mixture was stirred at 50° C. for 48 h, water was added. The mixture was extracted with EtOAc (3×), washed with brine, dried over anhydrous MgSO$_4$ filtered and evaporated. After chromatographic purification on silica gel, 1-(2-methoxy-ethoxy)-3-methyl-2-nitrobenzene was obtained in 85% yield (2.34 g). $^1$H NMR (500 MHz, CDCl$_3$) δ 7.28 (1H, t, J=8.0 Hz), 6.89 (1H, d, J=9.0 Hz), 6.85 (1H, d, J=8.0 Hz), 4.19 (2H, t, J=4.5 Hz), 3.72 (2H, t, J=5.0 Hz), 3.41 (3H, s), 2.30(3H, s).

Example 19

Preparation of (R)-7'-Chlorotryptophan, 1, and (S)-N-acetyl-7'-chlorotryptophan, 2

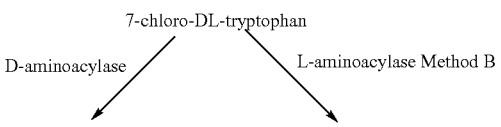

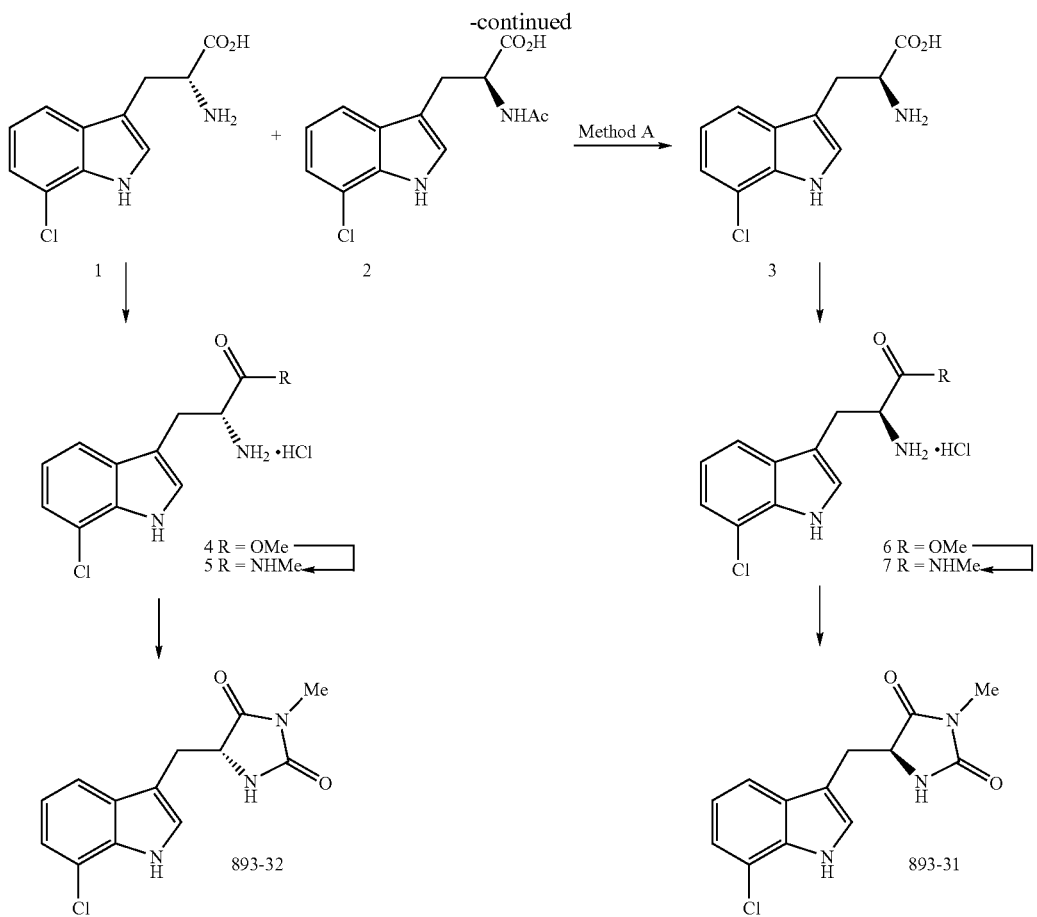

A mixture of N-acetyl-7'-chloro-DL-tryptophan (300 mg, 1.08 mmol), D-aminoacylase (10.1 MU/g, 8 mg) and cobalt dichloride (1.2 mg) in 30 mL of phosphate buffer solution (pH 7.8) was stirred at 37° C. for 2d. The pH of the reaction mixture was adjusted to 5 with 10% HCl and then filtered through a celite pad. The filtrate was extracted with ethyl acetate (3×40 mL). The aqueous layer was concentrated to give a pale yellow solid, which was extracted with methanol (4×2 mL). The combined methanol solutions were concentrated to give 200 mg of crude (R)-7'-chlorotryptophan as a white solid containing some inorganic salts. This crude product was used directly for the next reaction without further purification. The ethyl acetate solutions were combined and concentrated to give 150 mg of (S)-N-acetyl-7'-chlorotryptophan as a light yellow solid (100%).

(S)-7'-Chlorotryptophan, 3. Method A: (S)-N-acetyl-7'-chlorotryptophan was refluxed in 3 N HCl for 6 h to remove the acetyl group. Concentration of the reaction mixture gave x mg of (S)-7'-chlorotryptophan (x %). Method B: Prepared with L-aminoacylase using the same procedure described for (R)-7'-chlorotryptophan.

(R)-7'-Chlorotryptophan methyl ester hydrochloride, 4. Thionyl chloride (0.09 mL, 1.2 mmol) was dissolved in 3 mL of anhydrous methanol at 0° C. and then this solution was added to a flask containing crude (R)-7'-chlorotryptophan (200 mg, 0.5 mmol). After stirring at −5° C. for 4 h, the reaction mixture was allowed to warm to room temperature and stirred overnight before being concentrated. The white solid was collected, washed with ethyl acetate and dried in vacuo. The product was used directly without further purification.

(R)-7'-Chlorotryptophan methylamide hydrochloride, 5. To (R)-7'-chlorotryptophan methyl ester hydrochloride was added 4 mL of 2.0 M solution of methyl amine in methanol. The mixture was stirred for 3d at room temperature under an atmosphere of argon. Concentration of the reaction mixture gave the crude product as a white solid, which was used directly without further purification.

(R)-5-(7'-Chloro-1H-indol-3ylmethyl)-3-methyl-imidazolidine-2,4-dione. To a mixture of the crude (R)-7'-chlorotryptophan methylamide hydrochloride (ca. 0.5 mmol), pyridine (0.24 mL, 3.0 mmol), and dichloromethane (6 mL) at 0° C. was slowly added triphosgene (178 mg, 0.6 mmol) under argon. The reaction mixture was stirred at 0° C. for 1 h before removing the cooling bath. The stirring was continued overnight at room temperature under argon, then diluted with 120 mL of ethyl acetate. The organic solution was washed with 1N HCl (2×40 mL) and brine (40 mL), dried over anhydrous $MgSO_4$, filtered and concentrated. The residue was purified by chromatography on silica gel using hexane/ethyl acetate (50:50) to give 27 mg of pure product as a pale yellow solid (20% overall yield). $^1$H NMR (500 MHz, $CDCl_3$): δ2.98 (s, 3H), 3.00 (dd, 1H, J=9.0, 14.5 Hz), 3.46 (dd, 1H, J=3.5, 14.5 Hz), 4.29 (ddd, 1H, J=1.0, 3.5, 9.0 Hz), 5.30 (d, 1H, J=2.5 Hz), 7.09 (t, 1H, J=7.5 Hz), 7.15 (d, 1H, J=2.5 Hz), 7.23 (d, 1H, J=7.5 Hz), 7.51 (d, 1H, J=7.5 Hz), 8.35 (s, 1H). The optical purity (>98% ee) was determined by $^1$H NMR using a 0.02 M solution of the product in CDCl₃ in the presence of a chiral shift reagent (Europium tris[3-(trifluoromethylhydroxymethylene)-(+)-camphorate], 0.02 M).

(S)-5-(7'-Chloro-1H-indol-3ylmethyl)-3-methyl-imidazolidine-2,4-dione. Triphosgene (45 mg, 0.15 mmol) was added at 0° C. under argon to a mixture of (S)-7'-chlorotryptophan methylamide hydrochloride (0.28 mmol), pyridine (0.12 mL, 1.5 mmol), and dichloromethane (4 mL). The mixture was stirred at 0° C. for 2 h, then diluted with ethyl acetate (100 mL), washed with 1N HCl (2×30 mL) and brine (30 mL). The organic layer was dried by MgSO₄, filtered and concentrated. The residue was purified by chromatography on silica gel using dichloromethane/ethyl acetate (85:15) to give 20 mg of pure product as a pale yellow solid (26%). ¹H NMR (500 MHz, CDCl₃): δ 2.98 (s, 3H), 3.00 (dd, 1H, J=9.0, 14.5 Hz), 3.46 (dd, 1H, J=3.5, 14.5 Hz), 4.29 (ddd, 1H, J=1.0, 3.5, 9.0 Hz), 5.30 (d, 1H, J=2.5 Hz), 7.09 (t, 1H, J=7.5 Hz), 7.15 (d, 1H, J=2.5 Hz), 7.23 (d, 1H, J=7.5 Hz), 7.51 (d, 1H, J=7.5 Hz), 8.35 (s, 1H). The optical purity (>98% ee) was determined by ¹H NMR using a 0.02 M solution of the product in CDCl₃ in the presence of a chiral shift reagent (Europium tris[3 (trifluoromethylhydroxymethylene)-(+)-camphorate], 0.02 M).

Example 20

Preparation of 5-Benzo[b]thiophen-3-ylmethyl-3-methyl-2-thioxo-imidazolidin-4-one, 893-21

To a solution of 2-amino-3-benzo[b]thiophen-3-yl-propionic acid (221 mg, 1.0 mmol) in 4 mL pyridine/water (1:1) was added a solution of methylthioisocyanate (80.4 mg, 1.1 mmol). The resulting mixture was stirred at 60° C. for 18 h. The reaction mixture was allowed to cool to room temperature, diluted with 1N HCl (50 mL) and extracted with ethyl acetate (2×40 mL). The extracts were combined, washed with brine, dried over anhydrous magnesium sulfate, filtered, and concentrated to give a yellow solid. The solid was dissolved in a mixture of ethyl acetate/hexane/dichloromethane and then concentrated until precipitation began. The mixture was filtered to give 893-21 as a pale yellow solid. ¹H NMR (500 MHz, CDCl₃): δ 3.08 (dd, 1H, J₁=15 Hz, J₂=10 Hz), 3.26 (s, 3H), 3.62 (dd, 1H, J₁=14.5 Hz, J₂=3.5 Hz), 4.42 (ddd, 1H, J=10 Hz, J₂=3 Hz, J₃=1.0 Hz), 6.90 (bs, 1H), 7.30 (s, 1H), 7.40-7.46 (m, 2H), 7.77 (d, 1H, J=8.0 Hz), 7.90 (d, 1H, J=8.0 Hz).

Example 21

Synthesis of Hydantoins

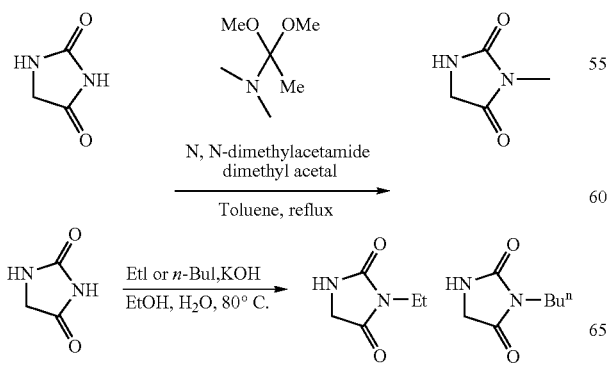

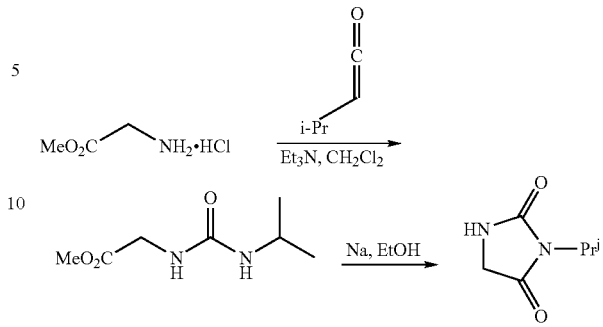

Methylhydantoin was prepared according to the method of Janin, Y. L., et al (Eur. J. Org. Chem., 2002, 1763). Ethyl and n-butylhydantoin were prepared utilizing a literature procedure (Justus Liebigs Ann. Chem., 1903, 327 and 383). i-Propylhydantoin was prepared according to the method of Park and Kurth (J. Org. Chem., 2000, 3520).

Example 22

Hydantoinindoles

The following hydantoinindoles were prepared utilizing the methodology described in Example 16.

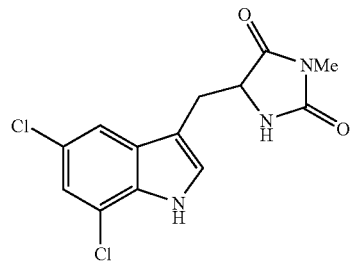

(893-33) ¹H NMR (500 MHz, CDCl₃): δ 8.35 (1H, brs), 7.49 (1H, s), 7.23 (1H, s), 7.17 (1H, s), 5.43 (1H brs), 4.29 (1H, dd, J=3.5, 8.0 Hz), 3.38 (1H, dd, J=4.0, 15.0 Hz), 3.01 (1H, dd, J=9.0, 15.0 Hz), 2.97 (3H, s).

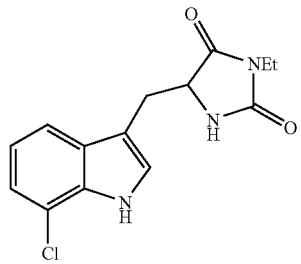

(893-34) ¹H NMR (500 MHz, CDCl₃): δ 8.33 (1H, brs), 7.52 (1H, d J=8.0 Hz), 7.23 (1H, d J=7.5 Hz), 7.15 (1H, d, J=2.5 Hz), 7.09 (1H, t, J=7.5 Hz), 5.25 (1H brs), 4.28 (1H, ddd, J=1.0, 3.0, 8.0 Hz), 3.49 (2H, m), 3.42 (1H, dd, J=3.0, 14.5 Hz), 3.04 (1H, dd, J=9.0, 14.5 Hz), 1.06 (3H, t, J=7.0 Hz).

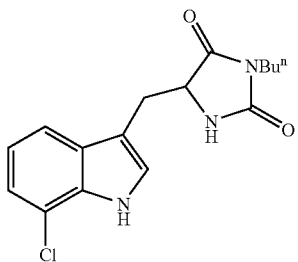

(893-35) ¹H NMR (500 MHz, CDCl₃): δ 8.33 (1H, brs), 7.52 (1H, d J=7.5 Hz), 7.22 (1H, d J=7.5 Hz), 7.15 (1H, d, J=2.5 Hz), 7.09 (1H, t, J=7.5 Hz), 5.23 (1H brs), 4.28 (1H, ddd, J=1.5, 4.0, 8.0 Hz), 3.48-3.36 (3H, m), 3.07 (1H, dd, J=8.0, 14.5 Hz), 1.38 (2H, quintet, J=7.5 Hz), 1.20-1.09 (2H, m), 0.84 (3H, t, J=7.0 Hz).

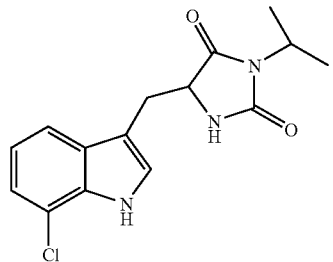

(893-44) ¹H NMR (500 MHz, CDCl₃): δ 8.33 (1H, brs), 7.51 (1H, d, J=8.0 Hz), 7.22 (1H, d, J=7.0 Hz), 7.14 (1H, d, J=2.5 Hz), 7.08 (1H, t, J=8.0 Hz), 5.32 (1H, brs), 4.24-4.15 (2H, m), 4.36 (1H, dd, J=9.0, 14.5 Hz), 3.06 (1H, dd, J=8.5, 15.5 Hz), 1.26 (3H, d, J=7.0 Hz), 1.24 (3H, d, J=7.5 Hz).

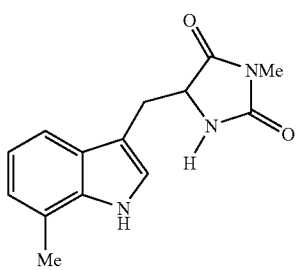

(893-38) ¹H NMR (500 MHz, CDCl₃): δ 8.08 (1H, brs), 7.46 (1H, d, J=8.0 Hz), 7.11-7.02 (3H, m), 5.34 (1H, brs), 4.30 (1H, ddd, J=1.0, 4.0, 10.0 Hz), 3.49 (1H, ddd, J=1.0, 4.0, 15.0 Hz), 3.00 (3H, s), 2.95 (1H, dd, J=9.5, 15.0 Hz), 2.49 (3H, s).

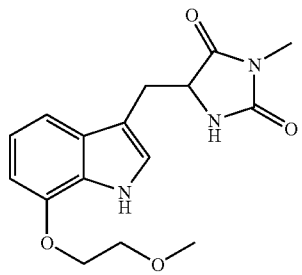

(893-41) ¹H NMR (500 MHz, CDCl₃): δ 8.66 (1H, brs), 7.23 (1H, d, J=8.0 Hz), 7.07-7.03 (2H, m), 6.70 (1H, d, J=7.5 Hz), 5.20 (1H, brs), 4.32-4.26 (3H, m), 3.84-3.80 (2H, m), 3.48 (3H, s), 3.49 (1H, dd, J=3.0, 15.0 Hz), 3.00 (3H, s), 2.93 (1H, dd, J=10.0, 15.0 Hz).

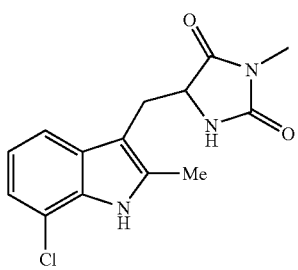

(893-43) ¹H NMR (500 MHz, CDCl₃): δ 8.13 (1H, brs), 7.39 (1H, d, J=10.0 Hz), 7.15 (1H, d, J=9.0 Hz), 7.04 (1H, t, J=10.0 Hz), 5.20 (1H brs), 4.25 (1H, ddd, J=1.0, 4.0, 9.0 Hz), 3.40 (1H, dd, J=4.5, 18.5 Hz), 3.00 (s, 3H), 2.92 (1H, dd, J=12.5, 18.5 Hz), 2.45 (3H, s).

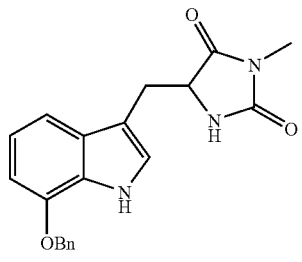

(893-0142) ¹H NMR (500 MHz, CDCl₃): δ 8.38 (1H, brs), 7.50-7.34 (5H, m), 7.22 (1H, d, J=7.5 Hz), 7.06 (1H, d, J=8.0 Hz), 7.04 (1H, d, J=3.0 Hz), 6.75 (1H, dd, J=7.0 Hz), 5.25 (1H, brs), 5.21 (2H, s), 4.29 (1H, ddd, J=1.0, 3.5, 9.5 Hz), 3.48 (1H, d, J=3.0, 14.5 Hz), 3.00 (3H, s), 2.93 (1H, dd, J=10.5, 15.5 Hz).

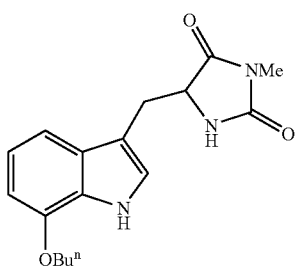

(893-47) ¹H NMR (500 MHz, CDCl₃): δ 8.32 (1H, brs), 7.18 (1H, d, J=8.0 Hz), 7.08-7.03 (2H, m), 6.66 (1H, d, J=8.0 Hz), 5.22 (1H, brs), 4.29 (1H, ddd, J=1.0, 4.0, 9.5 Hz), 4.14 (2H, t, J=6.5 Hz), 3.48 (1H, dd, J=3.0, 14.0 Hz), 3.00 (3H, s), 2.93 (1H, dd, J=10.0, 14.5 Hz), 1.88-1.80 (2H, m), 1.60-1.50 (2H, m), 1.00 (3H, t, J=7.5 Hz).

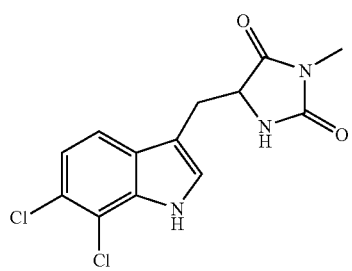

(893-50) ¹H NMR (500 MHz, CDCl₃): δ 8.33 (1H, brs), 7.43 (1H, d, J=8.0 Hz), 7.22 (1H, d, J=8.0 Hz), 7.14 (1H, d, J=2.5 Hz), 5.19 (1H, brs), 4.28 (1H, ddd, J=1.5, 4.0, 8.5 Hz), 3.40 (1H, dd, J=3.0, 14.5 Hz), 3.01 (1H, dd, J=9.0, 15.0 Hz), 2.96 (3H, s).

Example 23

Synthesis of 4-(7-Chloro-1H-indol-3-ylmethyl)-1-methyl-imidazolidin-2-one and 5-(7-Chloro-1H-indol-3-ylmethyl)-3-methyl-oxazolidine-2,4-dione The syntheses of 4-(7-chloro-1H-indol-3-ylmethyl)-1-methyl-imidazolidin-2-one and 5-(7-chloro-1H-indol-3-ylmethyl)-3-methyl-oxazolidine-2,4-dione were accomplished following the procedure of Lewis, R. et al. (J. Med. Chem., 1995, 923), except methyl amine was utilized in place of benzyl amines.

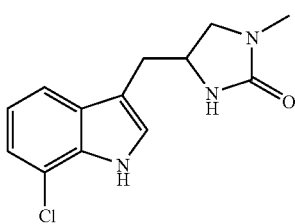

(893-52) ¹H NMR (500 MHz, CDCl₃): δ 8.33 (1H, brs), 7.48 (1H, d, J=9.5 Hz), 7.22 (1H, d, J=9.0 Hz), 7.13 (1H, d, J=2.5 Hz), 7.08 (1H, t, J=10.0 Hz), 4.40 (1H, brs), 3.95 (1H, quintet, J=8.5 Hz), 3.53 (1H, t, J=10.5 Hz), 3.19 (1H, dd, J=6.5, 11.0 Hz), 2.98 (1H, dd, J=5.5, 17.5 Hz), 2.95 (1H, dd, J=9.0, 18.0 Hz), 2.79 (3H, s).

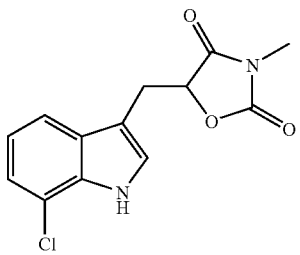

(893-53) ¹H NMR (500 MHz, CDCl₃): δ 8.33 (1H, brs), 7.53 (1H, d, J=8.5 Hz), 7.20 (1H, d, J=8.0 Hz), 7.19 (1H, d, J=2.5 Hz), 7.08 (1H, t, J=8.0 Hz), 5.06 (1H, t, J=5.0 Hz), 3.48 (1H, dd, J=4.5, 15.5 Hz), 3.36 (1H, dd, J=5.5, 16.0 Hz) 2.84 (3H, s).

Example 24

Synthesis of 4-(7-Chloro-1H-indol-3-ylmethyl)-oxazolidin-2-one

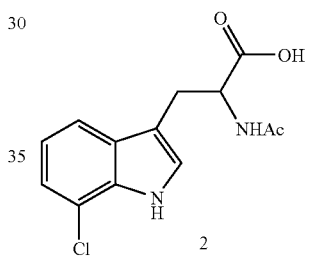

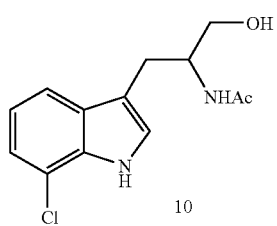

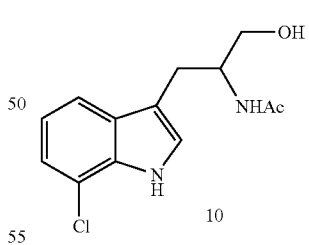

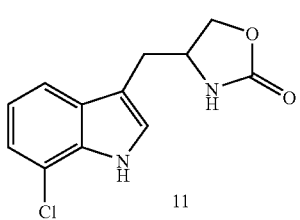

To a solution of 2 (500 mg, 1.78 mmol) in DMF solution (18 mL) was added sodium bicarbonate (299 mg, 3.56 mmol) and iodomethane (0.554 mL, 8.9 mmol). After the mixture was stirred at room temperature for 7 h, water was added. The mixture was extracted (3×) with ethyl acetate and the organic layers were dried (MgSO$_4$) and evaporated to give ester as a yellow oil.

Lithium aluminum hydride (68 mg, 1.78 mmol) was suspended in ether solution (15 mL). The ester in ether (3 mL) was added dropwise at 0° C. After stirred at room temperature for 1 h, the mixture was quenched with water (0.068 mL) at 0° C., followed by addition of 15% NaOH solution (0.068 mL) and water (0.200 mL). The precipitate was filtered, the organic filtrate was concentrated and the residue was purified by chromatography on silica gel to give alcohol 10 (370 mg, 78%).

A solution of the alcohol 10 (60 mg, 0.225 mmol) in 3N HCl solution was heated at 120° C. for 12 h. After cooled to room temperature, the mixture was evaporated to give brown a solid, which was used for the next reaction without purification.

The brown solid obtained above was dissolved in dichloromethane (2.25 mL). Triethylamine (0.063 mL, 0.45 mmol) and 1,1'-carbonyldimidazole (73 mg, 0.45 mmol) were added at room temperature. After stirred for 12 h, the mixture was concentrated and the residue was purified by chromatography on silica gel to give 4-(7-chloro-1H-indol-3-ylmethyl)-oxazolidin-2-one, 11, as a white solid (24 mg, 42%). (893-51) $^1$H NMR (500 MHz, CDCl$_3$): δ 8.35 (1H, brs), 7.47 (1H, d, J=10.0 Hz), 7.24 (1H, d, J=10.0 Hz), 7.15 (1H, d, J=2.5 Hz), 7.10 (1H, t, J=10.0 Hz), 5.14 (1H, brs), 4.56-4.44 (1H, m), 4.24-4.10 (2H, m), 3.08-2.96 (2H, m).

Example 25

Synthesis of 5-benzo[b]thiophen-3-ylmethyl-3-methyl-imidazolidine-2,4-dione

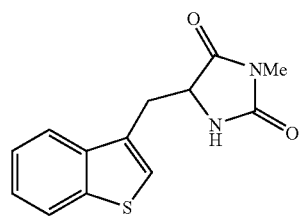

Thionyl chloride (0.36 mL, 4.8 mmol) was dissolved in 10 mL of anhydrous methanol at −5° C. This solution was then added to a flask containing crude (R)-3-benzothienylalanine (200 mg, 0.5 mmol). After stirring at −5° C. for 4 h, the reaction mixture was allowed to warm up overnight and then concentrated. The white solid [(R)-2-Amino-benzo[b]thiophen-2-yl-propionic acid methyl ester hydrochloride] was collected and washed with ethyl acetate. This material was then dried under vacuum and used directly for the next step.

To the crude (R)-2-Amino-benzo[b]thiophen-2-yl-propionic acid methyl ester hydrochloride was added 5 mL of 2.0 M solution of methyl amine in methanol. The mixture was stirred for 2 d at room temperature under argon. Concentration of the mixture gave the crude product [(R)-2-Amino-benzo[b]thiophen-2-yl-N-methyl-propionamide hydrochloride] as a white solid (600 mg), which was used directly for the next reaction without further purification.

To a mixture of the crude (R)-2-Amino-benzo[b]thiophen-2-yl-N-methyl-propionamide hydrochloride (600 mg, ca. 2.0 mmol), triethylamine (0.6 mL, 4.0 mmol), and dichloromethane (20 mL) was added carbonyl diimidazole (2.44 g, 15 mmol). The reaction mixture was stirred overnight at room temperature under argon and then diluted with 200 mL of ethyl acetate. The organic solution was washed with 1N HCl (2×50 mL) and brine (60 mL), dried over anhydrous MgSO$_4$, filtered and concentrated. The residue was purified by column chromatography on silica gel using hexane/ethyl acetate (50:50) to give 370 mg of 5-benzo[b]thiophen-2-ylmethyl-3-methyl-imidazolidine-2,4-dione as a white solid (71% overall yield). It is notable that the product was racemic indicative that racemization had occurred under these reaction conditions. (893-39) $^1$H NMR (500 MHz, CDCl$_3$): δ 7.89 (1H, dd, J=1.5, 7.5 Hz), 7.78 (1H, dd, J=1.0, 7.0 Hz), 7.41 (2H, m), 7.27-7.24 (1H, m), 5.46 (1H, s), 4.33 (1H, ddd, J=1.0, 3.5, 9.5 Hz), 3.60 (1H, ddd, J=1.0, 3.5, 14.5 Hz), 3.03 (1H, dd, J=9.5, 14.5 Hz), 3.02(3H, s).

Example 26

Cytotoxicity of Hydantoin and Thiohydantoin Compound Series

Figure 11:
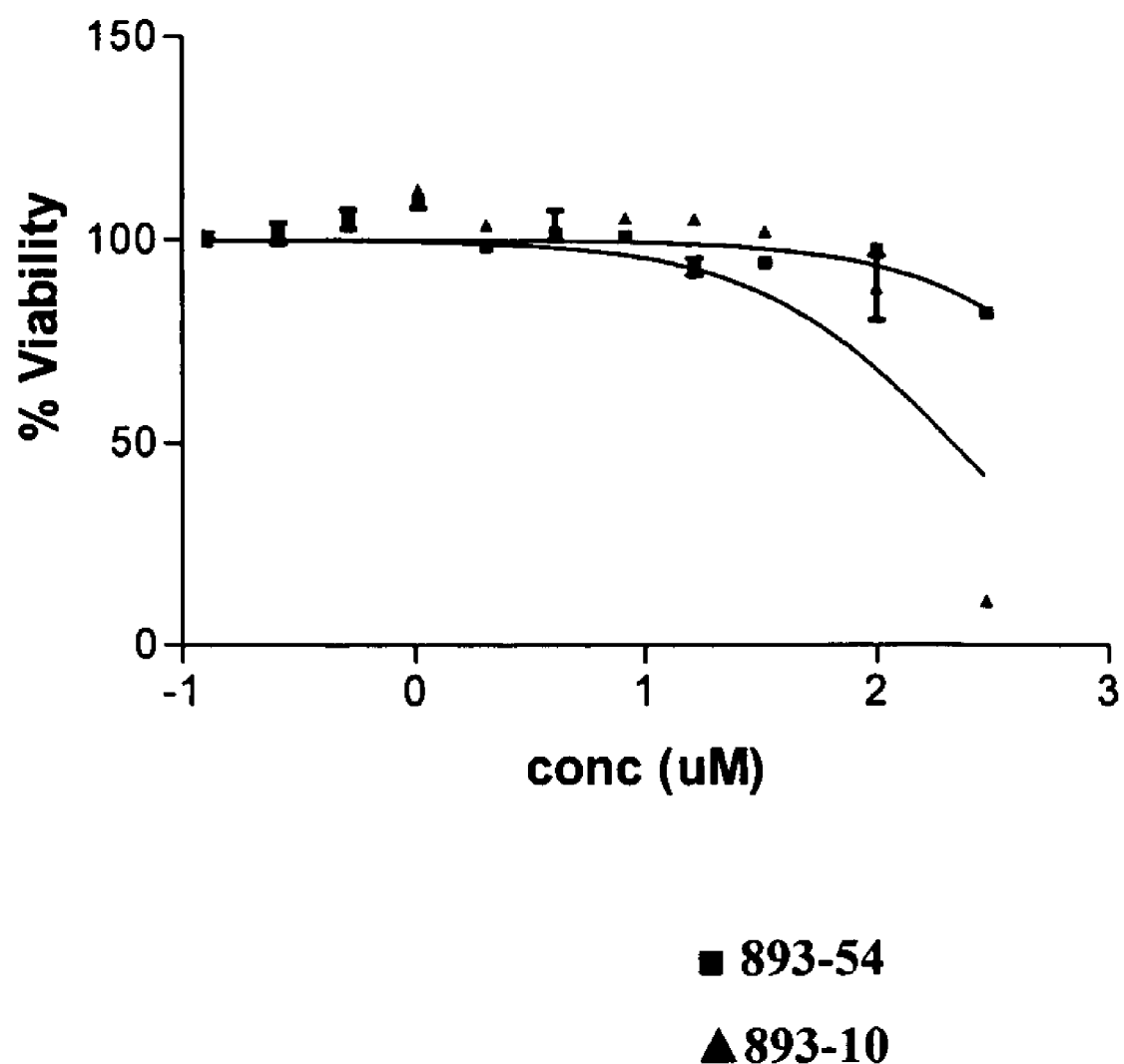
FIG. 11 is a graph that shows the cytotoxicity of hydantoin and thiohydantoin compounds.

FADD−/− Jurkat cells (Juo P, et al. Cell Growth Differ. 1999, 10(12):797-804) were seeded at the density of 5*10$^5$ cells/mL into 96 well white plates (Costar) at 100 μL/well. Cells were treated in duplicate with different concentrations of 893-10 or 893-54. After 30 hours viability of the cells was determined using luminescent ATP-based cell viability assay (CellTiter-Glo, Promega). Toxicity value was calculated as a ratio of viable cells in the wells treated with the compounds to the viable cells in the wells treated with DMSO (FIG. 11).

Example 27

Synthesis of 5-(7-Chloro-1H-indol-3-ylmethyl)-1,3-dimethyl-imidazolidine-2,4-dione

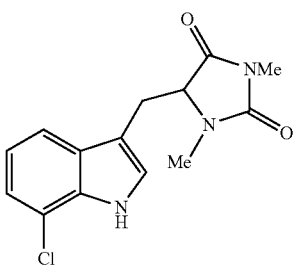

To a solution of 1-methylhydantoin (1.14 g, 10 mmol) in methanol (40 mL) was added 10N NaOH (1 mL) and iodomethane (0.8 ml, 12.9 mmol). The mixture was refluxed for 4 h and then allowed to cool. The reaction mixture was diluted with EtOAc (200 mL), washed sequentially with 1N HCl (50 mL×3), saturated NaHCO$_3$ (50 mL×3), saturated NaCl (50 mL×3), dried over anhydrous MgSO$_4$, filtered and concentrated. The crude product (1,3-Dimethylimidazolidine-2,4-dione) as a slightly yellow oil was used directly for the next step without further purification.

5-(7-Chloro-1H-indol-3-ylmethylene)-1,3-dimethylimidazolidine-2,4-dione was prepared 1,3-Dimethylimidazolidine-2,4-dione using the same procedure as described in Example 16. This material was used without further purification.

5-(7-Chloro-1H-indol-3-ylmethylene)-1,3-dimethylimidazolidine-2,4-dione was converted to 5-(7-Chloro-1H-indol-3-ylmethyl)-1,3-dimethylimidazolidine-2,4-dione using the same procedure as described in Example 16. (893-36) $^1$H NMR (500 MHz, CDCl$_3$): δ 8.32 (1H, brs), 7.49 (1H, d J=8.0 Hz), 7.19 (1H, d J=8.0 Hz), 7.08-7.04 (2H, m), 4.14 (1H, t, J=4.5 Hz), 3.37 (1H, dd, J=3.5, 15.0 Hz), 3.33 (1H, dd, J=5.0, 16.0 Hz), 2.93 (3H, s), 2.84 (3H, s).

Example 28

Synthesis of 5-(7-Chloro-1-methyl-1H-indol-3-ylmethyl)-3-methyl-imidazolidine-2,4-dione

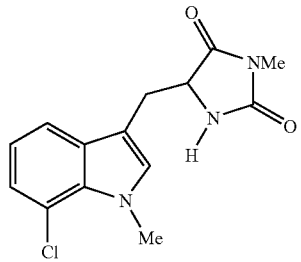

To a solution of 7-chloroindole (610 mg, 4 mmol) in anhydrous DMF (6 mL) was added NaH (170 mg, 60% dispersion in mineral oil, 4.3 mmol) at 0° C. under argon. The mixture was stirred at room temperature for 30 min before adding iodomethane (240 mg, 4 mmol). The resulting mixture was stirred overnight. The reaction mixture was diluted with EtOAc (200 mL), washed with saturated NaCl (10 mL×3), dried over anhydrous MgSO$_4$, filtered, and concentrated to give 7-chloro-1-methylindole. The residue was used directly for the next step without further purification. $^1$H NMR (500 MHz, CDCl$_3$): δ 4.14 (s, 3H), 6.46 (d, 1H, J=2.5), 6.95-6.98 (m, 2H), 7.12-7.14 (m, 1H), 7.48 (1H, dd, J=1.5, 7.5).

7-Chloro-1-methyl-1H-indole-3-carboxaldehyde was prepared from 7-chloro-1-methylindole using the same procedure as described in Example 16. $^1$H NMR (500 MHz, CDCl$_3$): δ 4.23 (s, 3H), 7.19 (1H, t, J=7.5), 7.28 (1H, dd, J=1.0, 7.5), 7.62 (s, 1H), 8.22-8.24 (1H, m), 9.98 (s, 1H).

5-(7-Chloro-1H-methyl-1H-indol-3-ylmethylene)-3-methylimidazolidine-2,4-dione was prepared from 7-Chloro-1-methyl-1H-indole-3-carboxaldehyde using the same procedure as described in Example 16. This crude material was used in the next step without further purification.

5-(7-Chloro-1-methyl-1H-indol-3-ylmethyl)-3-methylimidazolidine-2,4-dione was prepared from 5-(7-Chloro-1-methyl-1H-indol-3-ylmethylene)-3-methylimidazolidine-2,4-dione using the same procedure as described in Example 16. (893-37) $^1$H NMR (500 MHz, CDCl$_3$): δ 7.45 (1H, dd, J=1.0, 8.0 Hz), 7.17 (1H, dd, J=1.0, 7.5 Hz), 7.01 (1H, t, J=7.5 Hz), 6.88 (1H, s), 5.25 (1H, brs), 4.24 (1H, ddd, J=1.0, 3.5, 9.0 Hz), 4.11 (3H, s), 3.42 (1H, dd, J=4.5, 15.0 Hz), 2.99 (3H, s), 2.92 (1H, dd,=10.0, 15.0 Hz).

Having thus described several aspects this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:
1. A compound of the formula:

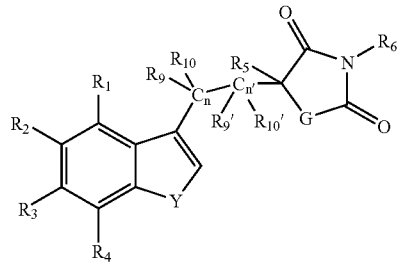

a stereoisomeric form thereof, or a pharmaceutically acceptable acid or base addition salt of the compound or of a stereoisomeric form thereof; wherein Y represents NR$_8$;
G represents NR$_7$;
R$_1$, R$_2$, and R$_3$ represent independently H, OH, OR$_8$, F, Cl, Br, I, N(R$_8$)$_2$, COOH, CO$_2$R$_8$, NO$_2$, NHC(O)R$_8$, lower alkyl, substituted lower alkyl, or aryl;
R$_4$ represents independently OH, OR$_8$, F, Cl, Br, I, N(R$_8$)$_2$, COOH, CO$_2$R$_8$, NO$_2$, NHC(O)R$_8$, methyl, methoxyl, lower alkyl, substituted lower alkyl, aryl, or amine;
R$_5$ and R$_7$ represent independently H or lower alkyl;
R$_6$ represents lower alkyl; each R$_8$ represents independently H, lower alkyl, substituted lower alkyl, aryl, substituted aryl, arylalkyl, alkenyl, or alkynyl;
R$_9$, R$_{10}$, R$_9$', and R$_{10}$' represent independently H, F, Cl, Br, I, lower alkyl, or substituted lower alkyl, or a three to six membered cycloalkyl that includes C$_n$ and/or C$_{n'}$; and
n and n' equals an integer from zero to five.

2. A pharmaceutical composition comprising:
(i) a compound of the formula:

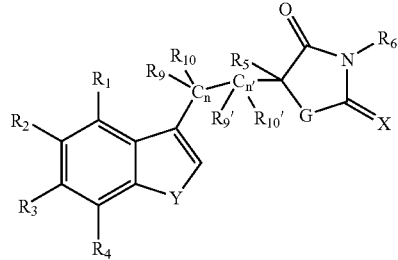

a stereoisomeric form thereof, or a pharmaceutically acceptable acid or base addition salt of the compound or of a stereoisomeric form thereof; wherein Y represents NR$_8$;
G represents NR$_7$;
R$_1$, R$_2$, and R$_3$ represent independently H, OH, OR$_8$, F, Cl, Br, I, N (R$_8$)$_2$, COOH, CO$_2$R$_8$, NO$_2$, NHC(O)R$_8$, lower alkyl, substituted lower alkyl, or aryl;
R$_4$ represents independently OH, OR$_8$, F, Cl, Br, I, N(R$_8$)$_2$, COOH, CO$_2$R$_8$, NO$_2$, NHC(O)R$_8$, methyl, methoxyl, lower alkyl, substituted lower alkyl, aryl, or amine;
R$_5$ and R$_7$ represent independently H or lower alkyl;
R$_6$ represents lower alkyl;
each R8 represents independently H, lower alkyl, substituted lower alkyl, aryl, substituted aryl, arylalkyl. alkenyl, or alkynyl;

$R_9$, $R_{10}$, $R_9'$, and $R_{10}'$ represent independently H, F, Cl, Br, I, lower alkyl, or substituted lower alkyl, or a three to six membered cycloalkyl that includes $C_n$ and/or $C_{n'}$; and n and n" equals an integer from zero to five; and (ii) a pharmaceutically acceptable carrier.

3. The pharmaceutical composition of claim 2, wherein the pharmaceutically acceptable carrier is chosen from a diluent, a solid filler, and a solvent encapsulating material.

4. The pharmaceutical composition of claim 2, wherein the pharmaceutically acceptable carrier is chosen from a sugar, a starch, cellulose, powdered tragacanth, malt, gelatin, talc, an excipient, an oil, a glycol, a polyoi, an ester, an agar, a buffering agent, alginic acid, pyrogen free water, isotonic saline, Ringer's solution, ethyl alcohol, a pH buffered solution, a polyester, a polyanhydride, and a polycarbonate.

5. A compound of the formula:

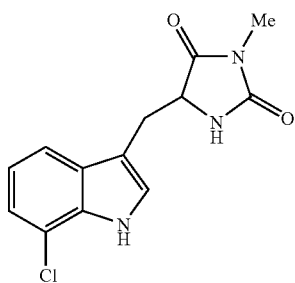

a stereoisomeric form thereof, or a pharmaceutically acceptable acid or base addition salt of the compound or of a stereoisomeric form thereof.

6. The compound of claim 5, wherein said compound is an enantiomer of the formula:

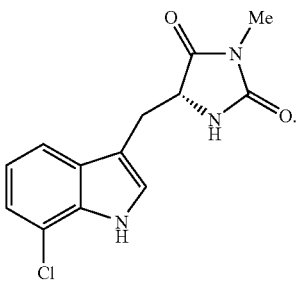

7. The compound of claim 5, wherein said compound is an enantiomer of the formula:

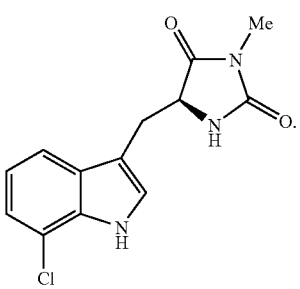

8. A pharmaceutical composition comprising:

(i) a compound of the formula:

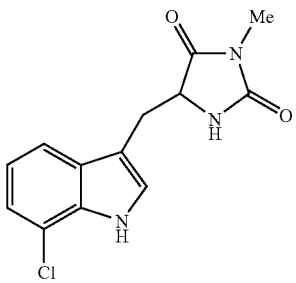

a stereoisomeric form thereof, or a pharmaceutically acceptable acid or base addition salt of the compound or of a stereoisomeric form thereof; and (ii) a pharmaceutically acceptable carrier.

9. The pharmaceutical composition of claim 8, wherein said compound is an enantiomer of the formula:

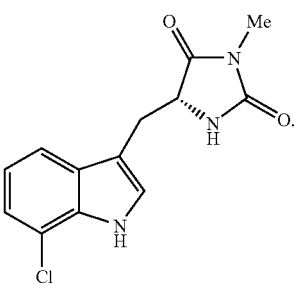

10. The pharmaceutical composition of claim 8, wherein said compound is an enantiomer of the formula:

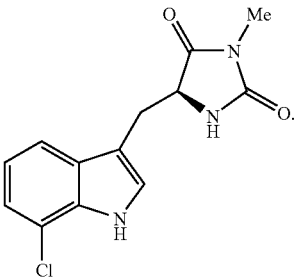

11. The compound of claim 1, wherein $R_9$, $R_{10}$, $R_9'$, and $R_{10}'$ represent independently H, F, Cl, Br, I, lower alkyl, or substituted lower alkyl; and n and n' are independently zero or one.

12. The compound of claim 11, wherein $R_9$, $R_{10}$, $R_9'$, and $R_{10}'$ each represents H.

13. The compound of claim 12, wherein $R_4$ represents Cl, Br, F, or I.

14. The compound of claim 13, wherein $R_6$ represents methyl.

15. A pharmaceutical composition comprising
(i) a compound of the formula:

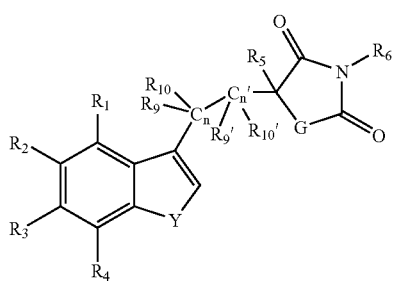

a stereoisomeric form thereof, or a pharmaceutically acceptable acid or base addition salt of the compound or of a stereoisomeric form thereof; wherein
Y represents $NR_8$;
G represents $NR_7$;
$R_1$, $R_2$, and $R_3$ represent independently H, OH, $OR_8$, F, Cl, Br, I, $N(R_8)_2$, COOH, $CO_2R_8$, $NO_2$, $NHC(O)R_8$, lower alkyl, substituted lower alkyl, or aryl;
$R_4$ represents independently OH, $OR_8$, F, Cl, Br, I, $N(R_8)_2$, COOH, $CO_2R_8$, $NO_2$, $NHC(O)R_8$, methyl, methoxyl, lower alkyl, substituted lower alkyl, aryl, or amine; $R_5$ and $R_7$ represent independently H or lower alkyl; $R_6$ represents lower alkyl;

each $R_8$ represents independently H, lower alkyl, substituted lower alkyl, aryl, substituted aryl, arylalkyl, alkenyl, or alkynyl;
$R_9$, $R_{10}$, $R_{9'}$, and $R_{10'}$ represent independently H, F, Cl, Br, I, lower alkyl, or substituted lower alkyl; and
n and n" are independently zero or one; and
(ii) a pharmaceutically acceptable carrier.

16. The pharmaceutical composition of claim 15, wherein $R_9$, $R_{10}$, $R_{9'}$, and $R_{10'}$ each represents H.

17. The pharmaceutical composition of claim 16, wherein $R_4$ represents Cl, Br, F, or I.

18. The pharmaceutical composition of claim 17, wherein $R_6$ represents methyl.

19. The compound of claim 11, wherein n equals 1 and n" equals 0.

20. The compound of claim 19, wherein Y and G each represents NH.

21. The compound of claim 20, wherein $R_4$ represents Cl.

22. The compound of claim 21, wherein $R_9$ and $R_{10}$ each represents H.

23. The compound of claim 22, wherein $R_1$, $R_2$, and $R_3$ each represents H.

24. The compound of claim 23, wherein $R_5$ represents H.

25. The compound of claim 24, wherein $R_6$ represents methyl.

* * * * *

UNITED STATES PATENT AND TRADEMARK OFFICE
CERTIFICATE OF CORRECTION

PATENT NO. : 7,491,743 B2  Page 1 of 1
APPLICATION NO. : 10/930690
DATED : February 17, 2009
INVENTOR(S) : Gregory D. Cuny et al.

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 276 days.

should read (*) Notice: Subject to any disclaimer, the term of this patent is extended or adjusted under 35 U.S.C. 154(b) by 472 days.

Signed and Sealed this

Seventeenth Day of August, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,491,743 B2 |
| APPLICATION NO. | : 10/930690 |
| DATED | : February 17, 2009 |
| INVENTOR(S) | : Gregory D. Cuny et al. |

It is certified that error appears in the above-identified patent and that said Letters Patent is hereby corrected as shown below:

In the Specification

Column 1, Lines 12-14, please replace the text:
"This invention was made with Government support under National Institutes of Health Grant No. GM-64703. The Government may have certain rights to this invention."

With:
--This invention was made with government support under GM064703 awarded by National Institutes of Health (NIH). The government has certain rights in this invention.--

Signed and Sealed this
Eighth Day of November, 2022

Katherine Kelly Vidal
*Director of the United States Patent and Trademark Office*